(12) United States Patent
Socolovsky et al.

(10) Patent No.: US 11,202,818 B2
(45) Date of Patent: Dec. 21, 2021

(54) METHODS AND COMPOSITIONS FOR MODULATING ERYTHROPOIESIS

(71) Applicants: President and Fellows of Harvard College, Cambridge, MA (US); University of Massachusetts, Boston, MA (US)

(72) Inventors: Merav Socolovsky, Brookline, MA (US); Allon M. Klein, Brookline, MA (US); Samuel Wolock, Cambridge, MA (US); Betsabeh K. Tusi, Shrewsbury, MA (US); Yung Hwang, Worcester, MA (US); Caleb Weinreb, Newton, MA (US)

(73) Assignees: President and Fellows of Harvard College, Cambridge, MA (US); University of Massachusetts, Boston, MA (US)

( * ) Notice: Subject to any disclaimer, the term of this patent is extended or adjusted under 35 U.S.C. 154(b) by 0 days.

(21) Appl. No.: 16/332,879

(22) PCT Filed: Sep. 14, 2017

(86) PCT No.: PCT/US2017/051581
§ 371 (c)(1),
(2) Date: Mar. 13, 2019

(87) PCT Pub. No.: WO2018/053142
PCT Pub. Date: Mar. 22, 2018

(65) Prior Publication Data
US 2019/0358295 A1    Nov. 28, 2019

Related U.S. Application Data

(60) Provisional application No. 62/394,570, filed on Sep. 14, 2016.

(51) Int. Cl.
| | | |
|---|---|---|
| *A61K 38/18* | (2006.01) | |
| *A61K 31/407* | (2006.01) | |
| *A61K 31/437* | (2006.01) | |
| *A61K 31/497* | (2006.01) | |
| *A61K 31/506* | (2006.01) | |
| *A61K 31/519* | (2006.01) | |
| *A61K 31/5377* | (2006.01) | |
| *A61K 31/541* | (2006.01) | |
| *A61K 38/20* | (2006.01) | |

(52) U.S. Cl.
CPC ........ *A61K 38/1816* (2013.01); *A61K 31/407* (2013.01); *A61K 31/437* (2013.01); *A61K 31/497* (2013.01); *A61K 31/506* (2013.01); *A61K 31/519* (2013.01); *A61K 31/5377* (2013.01); *A61K 31/541* (2013.01); *A61K 38/20* (2013.01)

(58) Field of Classification Search
None
See application file for complete search history.

(56) References Cited

U.S. PATENT DOCUMENTS

2013/0345158 A1    12/2013   Ahn et al.

FOREIGN PATENT DOCUMENTS

| EP | 1123313 A2 | 8/2001 |
|---|---|---|
| WO | WO-2018/053142 A2 | 3/2018 |

OTHER PUBLICATIONS

Clinical Trial: NCT00697632 (< https://clinicaltrials.gov/ct2/show/study/NCT00697632?term=mgcd265> Jun. 16, 2008.*
Locatelli et al. (Erythropoiesis stimulating agents in renal medicine; Oncologist 2011; 16 (suppl 3): 19-24).*
Hwang et al. ("The IL-17 Receptor IL-17RA is expressed by early erythroid progenitors and stimulates erythropoiesis" Dec. 2017; Blood: 130, Supplement 1, 3467).*
Coleman, "Science review: Recombinant human erythropoietin in critical illness: a role beyond anemia?," Crit Care, 8:337 (2004).
International Search Report and Written Opinion for International Application No. PCT/US2017/051581 dated Apr. 19, 2018.
Juul et al. "Epo and other hematopoietic factors," Semin Fetal Neonat M, 12(4):250-258 (2007).
Susumu et al., "Hippo signaling components, Mst1 and Mst2, act as a switch between self-renewal and differentiation in Xenopus hematopoietic and endothelial progenitors," Int J Dev Biol, 57:407-414 (2013).
Tusi et al. "Reconstructing Early Erythroid Development In Vivo Using Single-Cell Transcriptomics" Blood 128:1195 (2016).

* cited by examiner

*Primary Examiner* — James H Alstrum-Acevedo
*Assistant Examiner* — Tara L Martinez
(74) *Attorney, Agent, or Firm* — Foley Hoag LLP

(57) ABSTRACT

In certain aspects, disclosed herein are novel compositions and methods related to either the enhancement or inhibition of erythropoiesis that are useful, for example, in the treatment of anemia or erythrocytosis.

7 Claims, 35 Drawing Sheets

Figure 1(cont.)
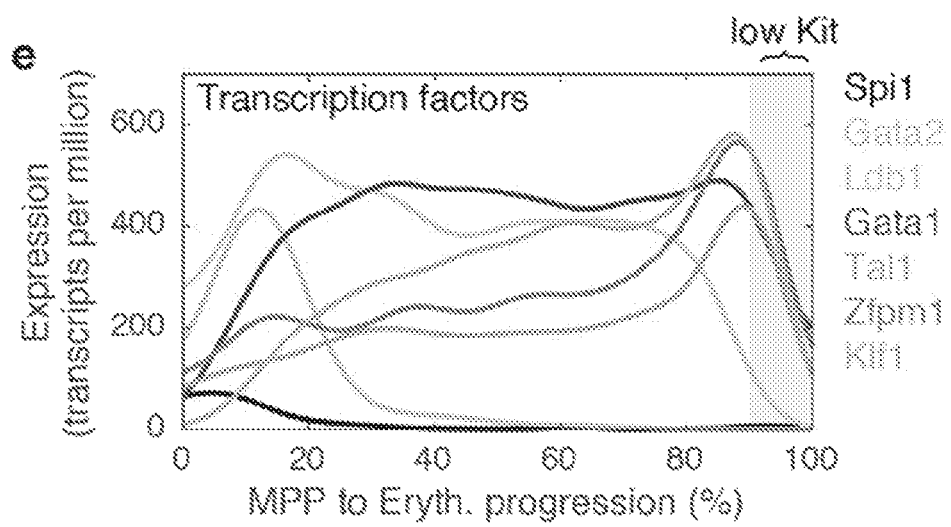
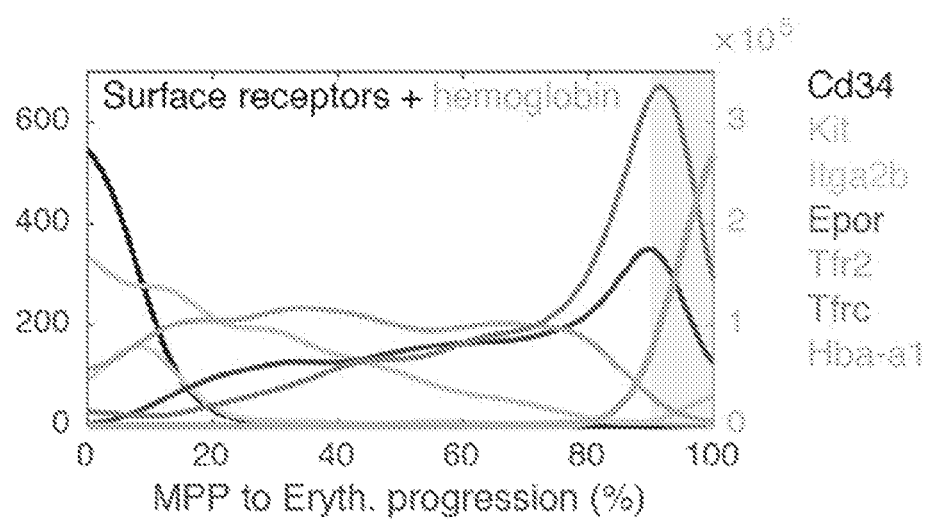

Figure 8

| SEQ ID NO. | Accession ID | Protein name | Sequence |
|---|---|---|---|
| 1 | NM_001244937.2 | MST1r | ```
   1 ggatcctcta gggtccctag tcgcctcgat ggagctcctc cggccgctgc ctcagtcctt
  61 cctgttgctg ctgtgttgc gggccctac ctgccaagcc ctgccggggc gaggactggc agtcccgcg
 121 cacccctac gcgccctctc gcgactttga cgtgaagtac gtggtcccca gcttctccgc
 181 cggaggcctg gtacaggcca tgtgtacta cgaggcgac agaaatgaga gtgctgttt
 241 tgtagccata cgcaatccgc tgcatgtgct acctgctgac ctgaagtctg tccagcct
 301 ggccacgggc ccacgggcct cccggtgaca cagacacaaa ggtgctgttg cgccggacc
 361 ccacgggcct cccggtgctca cagacacaaa ggtgctgttg ctggatccg cgctgctgc
 421 gctggtcagt tgtgctcagg gcctgcaggg cgctgttc ctgctcttc tagagcccg
 481 agggacagcc gtgcatctgg cagcgccagc tgggcacc atttgggacc ataacggca
 541 cgatgactgc cccgactgtg tgccaagccc actggcat ctcactggac cgtgtaactg tggttgagca
 601 aggccaggcc tcctattct actgtgtcta tcaggcgtct caaggctgac gcctcggat ctgcagctt
 661 cagcccagcc tcagtgtcta tgccaagca tcttgtctc tacagtattg aatacgtgca
 721 ctttgtgcg ttgtcagtgc tgccaagca cctgactgta cagccgggca gcgtacaga
 781 cagcttccac acgggaggct tcgtatactt ctgactgta cagccgggca gcgtacaga
 841 tgatcctagt gccctgcaca cacgcctgc acggcttagc gccactgagc cagagttggg
 901 tgactatcgg gagctggtcc tcgactgcag atttgctcca aaacgcaggc gccggggcg
 961 cccagaaggc gaccagccct accctgtgct gggcgttgcc cactccgctc cagtggctgc
1021 ccaactctga actccgcga gcatccgcga gggccaggaa gtactatttg ccttcccat
1081 gactggcaag gatgggtctg ctggcgtgg cccccaactct gtggtgaat cccagtcca
1141 tgacctgctg gacacactaa ttgatgaggg tgtggagcgc tgttgtgaat ccaaccgcc
1201 tccaggctgc cgggagccc tcgacttctt ccagtcgccc agttttgcc ccaaccgcc
1261 tggcctggaa gccttctca ccaaccacca g ctgccccac ttccctctgc tggtcagtag
1321 cagcttctca cgtgtgacc tattcaatgg gctgttggga ccagtacagg tcactgcatt
1381 gtatgtgaca cgcttgaca agtcacagt gcacacatg gcacacatgg atggcgtat
1441 ctgcaggtg gagctggtca gtcactaaa ctacttgctg tatgtgtcca acttctcact
1501 gggtgacagt gggcagcccg tgcagtcga cttcagtcgt cttgggacc acctactct
1561 tgcctctggg gaccaggttt tccaagtacc cctgctgcc cctgcaggc cccattcct
1621 gacctgtggg cgttgcctaa gggcatggca tttcatgggc tgtgctgtt gtggaacat
1681 gtgcggccag cagaaggagt gtcctggctc ctgcaactct aagggctgga cacctgtgg
1741 tactgagttc caccccccaca ccctttcacc gttgacctct aagggctgga acaccagct
1801 ctccaaactc taccctccacc cttctgtcc cactgcccaa gacagctca aaactcagca aggtactgt
1861 gggccaaagt cctgtgggg gtagaggagt ttgagtgaa actgagcc catgccacc aggcagcc
1921 gaaagactt gtagaggagt cgttgactaa catgccacc aggcacact tcgggtaga
1981 gcctaccctcc gtgctgagag gcttctctt catggagcca gtgctgatag cagtcctga
2041 cggcacctcc ccacggtgtg gctttctctt tctcactctt ctgcagcca cagccacg gggtcgtga
2101 cctctttggc ccacggtgtg gctgcacc cccctggcgac cccacggtgc gacccgctga
2161 aggcaccagc ctgacctgc ggcaaggt gtcaatgg ggccacggt ccctagcct
2221 gggcagctt ttatgtgcca caccccggg gctcagcag ctgctagcac gtcagagag
2281 gcaggtgggg ggtgccagg gatgcccagg tacctgttc ctgaccttc cagtacagag aagaccctgt
``` |

Figure 8 (cont.)

| | | |
|---|---|---|
| | | 2341 cgtgctaagc atcagcccca actgtgctta catcaactcc cacatcacca tctgtgcca<br>2401 gcatcttaact tcagcatggc acttagtgct gtcattccat gacggctta gggcagtgga<br>2461 aagcaggtgt gagaggcagc ttccagagca gcagctgtgc cgccttcctg aatatgtggt<br>2521 ccgagacccc caggatgg tgcaggaa tctgctgcc gagctgctgg gagctgctgg<br>2581 ctttacactg ccggcttc gcttcctaca ccaccccat ccaaccagtg ccaacctagt<br>2641 tccactgaag cctgaggagc atgccattaa gtttgaggtc tgggtagatg gtgaatgtca<br>2701 tatcctgggt agagtgtgc ccttgctgc ggccaggcc agatgggtc ccaagagca cgctccttgg<br>2761 tatcctgctg cctttgctg tgcttgtgc tgcactgcg actgactgg tctttcagcta<br>2821 ctgtggcgg aggaagcagc tagttcttcc tcccaacctg aatgacctgg catccctgga<br>2881 ccagactgct ggagccacac ccctgcctat tctgtactcg ggtcctgact acagaagtgg<br>2941 ccttgcactc cctgccattg atggtctgtc ttccaccact tgtgtccatg gagcatcctt<br>3001 ctccgatagt gaagatgaat cctgtcgcgg actgctgcgg caagagtgg ctgattcccc agtgagcggt<br>3061 ggacctggaa tctcgctct tggcctgagt caagatgtg cgccacttt ggagtgtct accacgaga<br>3121 ggtcacccac agtaccccag tcattggcaa agccacctt ggagtgtct accacgaga<br>3181 atacatagac caggcccaga atcgaatcca cctctccg agagggctg ctcatgcgtg gcctgaacca<br>3241 agagatgcag cagtggagg ctgctctca ttggtatcat gttgccacct gaggcctgc ccatgtgct<br>3301 ccgaatgtg ctgctctca ttggtatcat gttgccacct gaggcctgc ccatgtgct<br>3361 gctgccctat atgtgccacg gacctcatca gctttgccct gcagttcatc cgtccaccct agcggaaccc<br>3421 caccgtgaag gacctcatca gctttgccct gcagttcatc cgtccaccct agcggaaccc<br>3481 agagcagaag tttgtgcaca gggacctggc tgcgcggaac cgggcatgg agtacctggc<br>3541 cacagtcaag gtgctgact ttggtttggc ctgttggc ctgacaggg atgcgctgg agagcctgca<br>3601 tgttcaacag catcgcacg ctcgccacca tgtgaagtg gtgctgcat gtggctgcc tttgacctta cccacttcct<br>3661 gacctataga tttaccacca agtctgatgt cattgaccct tttgacctta cccacttcct<br>3721 gctgacacgg ggtccccac cataccgcca gtattctctg gatcctcgt accaagtgat<br>3781 ggcccaggt cggcgctgc cccgcctgc gtatccctg gatcctcgt accaagtgat<br>3841 gcagcaatgc tgggaggcag accaagcagt gcgacccacc ttcagagtac tagtgggga<br>3901 ggtgagcag atagtgtctg cactgcttg ggaccattat gtccagctgc cagcaaccta<br>3961 catgaactg ggccaagca cctgcatga gatgaatgtg cgtccagaac agccgcagtt<br>4021 ctcaccatg ccaggaatg tacgccggcc ccggccactc tcagagcctc ctcggcccac<br>4081 ttgacttagt tctggggctg gacctgctta gcctgctta gctaaccca agctgcctct<br>4141 gggccatgcc agccaggagc gcagctgc tccaccttgt tcctgccctt taacttcag<br>4201 aggcaatagg taaatgggc ccattaggc cctcactcca cagagtgagc cagtgaggc<br>4261 agtcctgcaa catgtattta tggagtgcct gctgtgacc ctgtcttctg ggcacagtgg<br>4321 actcagcagt gaccacaca acactgaccc ttgaaccaat aaaggaacaa atgactatta<br>4381 aagcacaaa aaaaaaaaa aa | MST1r |
| 2 | NP_001231866.1 | 1 mellpplpqs flllllpak paagedwqcp rtpyaasrdf dvkyvvpsfs agglvqamvt<br>61 yegdrnesav fvairnrlhv lgpdlksvqs latgpagdpg cgtcaacgpg phgppgdtdt<br>121 kvlvidpalp alvscgssig grcflhdlep ggtavhlaap aclfsahhnr pddcpdcvas<br>181 plgtrvtvve cggasyfyva ssldaavaas fsprvsirr lkadasgfap gfvalsvlpk<br>241 hlvsyieyv hsfhtgafvy fltvqpasvt ddpsalhtrl arlsatepel gdyrelvldc<br>301 rfapkrrrrg apegggppypv lrvahsapvg aqlatelsia eggevlfgvf vtgkdggpgv<br>361 gpnsvvcafp idldtlide gverccespv hpglirrgldf fgspsfcpnp pglealspnt |

Figure 8 (cont.)

```
 421 scrhfpilvs ssfsrvdlfn gligpvqvta lyvtrldnvt vahmgtmdgr ilqvelvrsl
 481 nyllyvsnfs lgdsgqpvqr dvsrlgdhll fasgdqvfqv piqgpgcrhf ltcgrclraw
 541 hfmgcgwcgn mcgqkecpg swqqdhcppk ltefhphsgp lrgstritlc gsnfylhpsg
 601 lvpegthqvt vgqspcrpip kdssklrpvp rkdfveefec eleplgtqav gptnvsltvt
 661 nmppgkhfrv dgtsvlrgfs fmepvliavq plfgpraggt cltieggsls vgtsravivn
 721 gtecilarvs egqlicatpp gatvasvpls lqvggaqvpg swtfqyredp vvlsispncg
 781 yinshiticg qhltsawhlv lsfhdglrav esrcerqlpe gqlcrlpeyv vrdpggwvag
 841 nlsargdgaa gftlpgfrfl ppphppsanl vplkpeehai kfevcvdgec hilgrvvrpg
 901 pdgvpqstll gillpliliv aalatalvfs ywwrrkqlvl ppnindlasl dqtagatplp
 961 llysgsdyrs glalpaidgl dsttcvhgas fsdsedescv pllrkesiql rdldsaliae
1021 vkdvlipher vvthsdrvig kghfgvvyhg eyidqaqnri qcaiksisri temqveafl
1081 regilmrgln hpnvlaligi mlppeglphv llpymchgdl lqflrspqrn ptvkdllsfg
1141 lqvargmeyl aeqkfvhrdl aarncmldes ftvkvadfgl ardiidreyy svqqhrharl
1201 pvkwmalesl qtyrlttksd vwsfgvllwe lltrgappyr hldpfldlthf laggrrlpqp
1261 eycpdslyqv mqgcweadpa vrptfrvlvg eveqivsall gdhyvqlpat ymnlgpstsh
1321 emnvrpeqpq fspmpgnvrr prplsepprp t
```

Figure 9

| SEQ ID NO. | Accession ID | Protein name | Sequence |
|---|---|---|---|
| 3 | NM_020998.3 | Msp | 1 cagcaggccc tgagctgacg tgtggagcca gagccaccca atcccgtagg gacaggtttc<br>61 acaacttccc ggatgggct gtgtggttc acagtgcagc ctccagccag aaggatgggg<br>121 tggctcccac tcctgctgct tctgactcaa tgcttagggg tccctgggca gcgctcgcca<br>181 ttgaatgact tccaagtgct ccgggcaca gagctacagc acctgctaca tcggtggtg<br>241 cccggcctt ggcaggaga tgtgcagat gctgaagagt gtgctggtcg ctgtgggccc<br>301 ttaatgact gccggccctt ccactacaac gtgagcagcc atggttgcca actgctgcca<br>361 tggactcaaa actcgcccca cacgaggctg cggcgttctg ccctcttccag<br>421 aagaaagact acgtacggac ctgcatcatg aacaatgggg ttgggtaccg gggcaccatg<br>481 gccacgaccg tgggtggct gccctgccag gcttggagcc acaagttccc aaatgatcac<br>541 aagtacacgc ccactctccg gaatggcctg gaagagaact tctgccgtaa ccctgatggc<br>601 gacccggag gtccttggtt ctacacaaca gaccctgctg tgccttcca gagctgcggc<br>661 atcaaatcct gccggagc cggtgtgtc tggtgcaatg gcgaggaata ccggcgcg<br>721 gtagaccgca cggagtcagg gcgagtgc gtcctcgac caaggtctgg atcttcagca acgacaacta ttgccggaat<br>781 caccccttcg agccggcaa gttcctcgac actacgatc cgcacggga gcgagagttc<br>841 cctgacggct ccgagcgggc ccgcgtgcg gtccgaggca cagccccgcc aagaggccac aactgtcagc<br>901 tgtgacctcc ggaagggtga gggctaccgg gcacagcca ataccaccac tgcggggta<br>961 tgcttccgcg gttgggacgc gcaaatcccg cattacgcc gattacgcc agaaaatac<br>1021 ccttgccagc acccttcgga gaacttctgc cggaacccg acggctcaga gtcgccctgg<br>1081 gcgtgcaaag tgccgcccgg catgcgcgcg gcctttgct accagatccg gcgttgtaca<br>1141 tgcttcacac ctgctaccac ggccaggg cgtgtccg agcagtaccg cggcacggtc<br>1201 gacgacgtgc gcaaggtgt ccagtgcagt ccgctgtccg ctgagcgcc gcacaagccg<br>1261 agcaagaccc ttacctccga accgcatgca caactggagg agaacttctg cggaaccca<br>1321 cagttcacgt gccatggcc ctgtcctac acgatgacc caagaccc attcgactac<br>1381 gatgggata gccatgggc tgatgaccag cgccatcaa tcctgacc cccagaccc<br>1441 tgtgcctgc gacgcttcgc agaagtgtgt caagagggtg gatcggctgg atcagcggcg ttccaagctg<br>1501 gtgtcagttg ggccatcc gggcaactca cctggacag tcagcttgcg gaatcggcag<br>1561 cgcggtgttg tctgcgggg gtcctcagtg aaggagcagt ggatactgac tgcccggcag<br>1621 ggccagcatt cctgccatt gcctccacg ggctacgagg tatgtttggg cacctgttc<br>1681 tgcttctcct agcatggaga gccaagccta cagggtcc cagtagccaa gatggtgt<br>1741 cagaacccac agcatggaga gccaagccta gccaagccta cagtagccaa gatggtgtgt<br>1801 gggccctcag gctccacgtc tgtcctgctc aagctggaga gatctgtgac cctgaaccag |

Figure 9 (cont.)

| | | |
|---|---|---|
| 4 | NP_066278.3 | Msp |

```
1861 cgtgtggccc tgatctgcct gcccctgaa tggtatgtgg tgcctccagg gaccaagtgt
1921 gagattgcag gctgggtga gaccaaaggt acgggtaatg acacagtcct aaatgtggcc
1981 ttgctgaatg tcatctccaa ccaggagtgt aacatcaagc accgaggacg tgtgcggag
2041 agtgagatgt gcactgaggg actgttggcc cctgtggggg cctgtgaggg tgactacggg
2101 ggcccacttg cctgcttac ccacaactgc tggtcctgg aaggaattat aatcccaac
2161 cgagtatgcg caaggtcccg ctggccagct gtcttcacgc gtgtctctgt gtttgtggac
2221 tggattcaca agtcatgag actgggttag gccagcctt gatgccatat gccttgggga
2281 ggacaaaaact tcttgtcaga cataaagcca tgtttcctct ttatgcctgt aaaaaaaaaa
2341 aaaaaaaa 1 mglwwvtvqp parrmgwlpl lllltqclgv pggrsplndf qvlrgteigh llhavvpgpw
 61 qedvadaeec agrcgplmdc rafhynvssh gcqilpwtqh sphtrirrsg rcdlfqkkdy
121 vrtcimnngv gyrgtmattv rfqscgiksc reaacvwcng eeyrgavdrt esgrecqrwd lqhphqhpfe
181 pwcyttdpav rfqscgiksc erpwcyttdp qierefcdlp rcgseaqprq eattvscfrg
241 pgkfldqgld dnycrnpdgs erpwcyttdp ftpekyackd lrenfcrnpd gseapwcfti
301 kgegyrgtan tttagvpcqr wdaqiphqhr pqdcyhgage qyrgtvsktr kgvqcqrwsa etphkpqftf
361 rpqmraaficy qirrctddvr pqdcyhgage hgpwcytmop rtpfdycalr rcaddqppsi ldppdqvqfe
421 tsephaqlee nfcrnpdgds hgpwcytmop ghpgnspwtv slnrqgghf cggslvkeqw iltarqcfss
481 kcgkrvdrld qrrsklrvvg ghpgnspwtv hgepslqrvp vakmvcgpsg sqlvlikier svtlnqrval
541 chmpitgyev wlgtlfqnpq hgepslqrvp wgetkgtgnd tvlnvalinv isnqecnikh rgrvresemc
601 iclppewyvv ppgtkceiag wgetkgtgnd glilpnrvca rsrwpavftr vsvfvdwihk
661 tegliapvga cegdyggpla cfthncwvle
721 vmrlg
```

Figure 10

| SEQ ID NO. | Accession ID | Protein name | Sequence |
|---|---|---|---|
| 5 | NM_001005861.2 | RYK | 1 cggctcgggg ctgtgagcgg ctcgggccg gggtgggcc gcggtgcggc ggcggccga<br>61 cgctcctctt cggcggcgc ggcggcggct atgcgtgggg cggcgcggct gggcggccg<br>121 ggccggagtt gcctcccggc ggctccggc ctgagggcc cgccgcccgc gccgctgctg<br>181 cttctgcttg gctgttgcc gctgtgcc ggcctgcgcg ctgcgccgcg cccgcccg<br>241 cggcccccgg agctgcagtc ggcttccgcg gggccagcgc tgagtctcta cctgagcgag<br>301 gacgaggtgc gccggctgat cggtcttgat gcagaactt attatgtgag aaatgacctt<br>361 attagtcact acgctctatc ctttagtctg ttagtaccca gtgacaaaa tttcctgcac<br>421 ttcacctggc atgcgaagtc caaggttgaa tataagctgg gattccaagt ggacaatgtt<br>481 ttggcaatgg atatgcccca ggtcaacatt tctgttcagg gggaagttcc acgcactta<br>541 tcagtgttc gggtagagct ttcctgtact ggcaaagtag attctgaagt tatgatacta<br>601 atgcagctca acttgacagt aaattcttca aaaatttta ccgtcttaaa tttaaacga<br>661 aggaaaatgt gctacaaaa acttgaagaa gtaaaaactt cagccttgga caaaaacact<br>721 agcagaacta tttatgatcc tgtacatgca gctccaacca cttctacgcg tgtgttttat<br>781 attagtgtag gggttttgttg tgcagtaata tttctcgtag caataatatt agctgttttg<br>841 caccttcata gtatgaaaag gattgaactg gatgacagca ttagtgccag cagtagttcc<br>901 caagggctgt ctcaccatc caccagacg actccagtac tgagagcaga cacgcccaac<br>961 aatgcaactc ctatcaccag ctccttaggt tatcctacct tgcggataga gaagaacgac<br>1021 ttgagaagtg tcactctttt ggaggccaaa ggcaaggtga aggatatagc aatatccaga<br>1081 gagaggataa ctctaaaaga tgtactccaa gaaggtactt ttgggcgtat tttccatggg<br>1141 attttaatag atgaaaaaga tccaaataaa gaaaaacaag catttgtcaa aacagttaaa<br>1201 gatcaagctt ctgaaattca ggtgacaatg atgctcactg aaagttgtaa gctgcgaggt<br>1261 cttcatcaca gaaatctct tcctattact catgtgtta tagaagaagg agaaaagccc<br>1321 atgtgatat tgccttacat gaattggggg aatcttaaat tgttttacg acagtgcaag<br>1381 ttagtagagg ccaataatcc acaggcaatt tctcagcaag acctgtaca catgctatt<br>1441 cagattgcct gtggaatgag ctacctgcc agaagggaag tcatccacaa agacctgcct<br>1501 gccaggaact gtgtcacttt caagttaaga tgacacactt caagttactt tgccctctcc<br>1561 agagacttgt tcccatgga ctatcactga gagttctcta atgaaaacag gccagttcgt<br>1621 tggatgctc ttgaaagtct ggttaataac gagttctcta gcgctagtga tgtgtgggcc<br>1681 ttttgagtga cgctgtggga actcatgact ctggccaga ctccctacgt ggacattgac<br>1741 ccctttcgaga tgcccgcata cctgaagatt ggttaccgaa gagcctagcc aatcaactgt<br>1801 cctgatgaat tatttgctgt gatgcctgt tgctggcct tagatccaga ggagaggccc |

Figure 10 (cont.)

| | | |
|---|---|---|
| | 1861 aagtttcagc agctggtaca gtgcctaaca gagtttcatg cagccctggg ggcctacgtc<br>1921 tgactcctct cccatcccac accatcagga agaaggtgcc tgtcggggct cacttgaagc<br>1981 ctgtcaggga tgctttgtat ctaacacaac gccaacagaa gcacattgt cttccagaac<br>2041 accgtgcctt agaaatgctt tagaatctga acttttaag acagacttaa taatgtggca<br>2101 tattctag atatcacttt tattaggttg aactgaaagg gtttttgtaa attttttggc<br>2161 caaaatttt taaaacatac ttacttgga ctagggtac attcttacaa aataaataaa<br>2221 cagttttta aattgtttag acacagatat ttgaattag ctatcttagt gccaactgct<br>2281 tttattttt ttacttcatc aaggtgatgt aagtgactca cctttaaagt ttttttagtg<br>2341 ttatttta tcactactct gggaaatggt ttgtcttcaa gatgcaatac ttttcttagt<br>2401 aaaggaaaaa cagcataaaa agatacctgg tctgccttgt acaagaaaag gcaatattag<br>2461 aggaagaaaa tttaaagaaa agctagagga aaaaaaaatt tttttttaaaa tacttattag<br>2521 aagcaaactg cccttgcatg gaaaactgtt tattttttc agtgaaaagg aattctgctt<br>2581 tcgtgttttt gggaaagcag gaactgagtt cattacatct ttaatttggc agaaattagc<br>2641 ctttctgtga accagatgtg gtttgggca gatctgtagt aaacaatggt gattttattt<br>2701 attttttactc tctggaaaag gagataatac aattccagaa agtgaactca tatttctaag<br>2761 gttaagattc cctttattg cacctagaat agtgctatgc acagagcggg tgcttgagtt<br>2821 gttgtcgttt ttgtttgtt ttttaaatgt aaactgtaa atttgtgct tatcttcaag<br>2881 gctgcttaa gtataaaatt gttttttaaa cacttgaaaa attaaaggat ttgttttata<br>2941 tt | |
| 6 NP_001005861.1 | 1 mrgaarlgrp grsclpgarg lrappppll lilallpilp apgaaaapap rppelqsasa<br>61 gpsvslylse devrrligid aelyyvrndl ishyalsfsl lvpsetnflh ftwhaksve<br>121 ykigfgvdnv lamdmpqvni svggevprtl svfrvelsct gkvdsevmil mqlnltvnss<br>181 knftvlnfkr rkmcykklee vktsalcknt srtiydpvha apttstrvfy isvgvccavi<br>241 flvailiavl hlhsmkriel ddsisassss gglsqpstqt tqyiradtpn natpitsslg<br>301 yptlriekd lrsvtlieak gkvkdiaisr eritlkdvlq egtfgrifhg ilidekdpnk<br>361 ekqafvktvk dqaseigvtm mltesckirg lhhrnlipit hvcieegekp mvilpymnwg<br>421 nlkiflrgck lveanrpqai sqqdlvhmai qiacgmsyla rrevihkdla arncviddti<br>481 qvkitdnals rdlfpmdyhc lgdnenrpvr wmaleslvnn eifssasdvwa fgvtlwelmt<br>541 lggtpyvdid pfemaaylkd gyriagpinc pdeifavmac cwaidpeerp kfqqlvqclt<br>601 efhaalgayv | RYK |

Figure 11

| SEQ ID NO. | Accession ID | Protein name | Sequence |
|---|---|---|---|
| 7 | NM_001256105.1 | WNT5a | ```
   1 gctccactcg cctccgtgct ctctcgccc atggaattaa ttctggctcc acttgttgct
  61 cggcccagaa gtccattgga atattaagcc caggagttgc tttggggatg gctggaagtg
 121 caatgtcttc caagtcttc ctagtgctt tgccatatt tttctccttc gcccaggttg
 181 taattgaagc caattcttgg tgtcgctag gtatgaataa ccctgttcag atgtcagaag
 241 tatatattat aggagcacag cctcctgca gccaactggc aggactttct caaggacaga
 301 agaaactgtg ccactgtat caggaccaca tgcagtacat cggagaaggc gcgaagacag
 361 gcatcaaaga atgccagtat caattccgac atcgaaggtg gaactgcagc actgtggata
 421 acacctctgt ttttggcagg gtgatcgaga taggcagccc cgagacggcc ttcacatacg
 481 cggtgagcgc agcaggggtg gtgaacgcca tgagccggc gtgccgcgag gcgagctgt
 541 ccacctgcgg ctgcagccgc gccgcgcc ccaaggacct gcgcgggac tggctctggg
 601 gcggtcgg cgacaacatc gactatgct accgctttgc caaggagttc gtggacgccc
 661 gcgagcggga gcgcatccac gccaaggct gctacgagag tgctcgcatc ctcatgaacc
 721 tgcacaacaa cgaggccggc cgaggacgg tgtacaacct gcctgatgtg gcctgcaagt
 781 gccatgggt gtccggctca tgtagcctga agacatgctg gctgcagctg gcagacttcc
 841 gcaaggtggg tgatgccctg aaggagaagt acgacagcgc ggccgccatg cggctcaaca
 901 gccgggcaa gttggtacag gtcaacagcc gcttcaactc gccaccaca caagacctgg
 961 tctacatcga cccagccct gactactgcg tgcaatga gagcacggc tcgctgggca
1021 cgcagggccg cctgtgcaac aagacgtcgg aggcatgga tggctgccag ctcatgtgct
1081 gcggccgtgg ctacgaccag ttcaagaccg tgcagacgga gcgctgccac tgcaagttcc
1141 actgtgtgct ctacgtcaag tgcaaggaagt gcacggagat cgtggaccag tttgtgtgca
1201 agtagtgggt gccaccagc actcagccc gctccagga gctccagga tattttttat
1261 acagttgatt ccttttttg tggttttg ttttagaaa tattttttat agaactctgt
1321 cggaaccatt tttttcctg ttaccatcta ggtttattat taatattata
1381 attattattt ggcaataatg ggtgggaa ccaagaaaaa tattatttt gtggatcttt
1441 gaaaggtaa tacaagactt ctttgatag tataagatga agggaaata acacataccc
1501 taacttagct gtgtgacat gtacacatc cagaaggtaa ttccagttga agaggtgg tagaaatcta
1561 tcaaatatgc catcatatgg gatgggtagg gttgtaaatt ctctgtgca agataaaagg
1621 ttcacaattc agctttctag gccaaaatga acaaaacaaa gttgtaaatt ctctgtgca agataaaagg
1681 tctttgggaaa acaaaacaaa ataatattaca atggaaggac tgctagcttg
1741 ctttctgcat tttcaaatt ataattaca atggaaggac tgctagcttg
1801 gaaaaaggt atatcacatg tctcattctc ctcaaatatt ccatttgcag acagaccgtc
``` |

| NP_001243034.1 | WNT5a |
|---|---|

```
4021 tgctgttgta acatcccaga gaagaatgaa aaggcacatg ctttatccg tgaccagatt
4081 tttagtccaa aaaatgtat tttttgtgt gttaccact gcaactattg cacctctcta
4141 tttgaattta ctgtgacca tgtgtggtgt ctctatgcc tttgaaagca gttttataa
4201 aaagaaagcc cgggtctgca gagaatgaaa actggttga aactaaaggt tcattgtgtt
4261 aagtgcaatt aatacaagtt attgtgcttt tcaaaaatgt acacggaaat ctggacagtg
4321 ctccacagat tgatacatta gccttttgct tttcctttc cggataacct tgtaacatat
4381 tgaaaacttt taagatgcc aagaatgcat tattccaca aaaacagca gaccaacata
4441 tagagtgttt aaaatagcat ttctgggcaa attcaaactc ttgtggttct aggactcaca
4501 tctgtttcag tttttcctca gttgtatatt gaccagtgtt ctttattgca aaaacatata
4561 cccgatttag cagtgtcagc gtatttttc ttctcatcct ggagcgtatt caagatcttc
4621 ccaatacaag aaaaattaata aaaaatttat atataggcag cagcaaaaga gccatgttca
4681 aaatagtcat tatggctca aatagaaaga agactttaa gtttaatcc agtttatctg
4741 ttgagttctg tgagctactg accctcctgag actggcactg tgtaagtttt agttgcctac
4801 cctagctctt ttctcgtaca attttgccaa taccaagttt caatttgttt ttacaaaaca
4861 ttattcaagc cactagaatt atcaaatatg acgctatagc agagtaaata ctctgaataa
4921 gagaccggta ctagctaact ccaagagatc gttagcagca tcagtccaca aacacttagt
4981 ggcccacaat atatagagag ataagaaagg tagttataac ttgaagcatg tatttaatgc
5041 aaataggcac gaagccacag gtctaaaata ctacatgtc actgtaagct atacttttaa
5101 aatatttatt tttttaaag tattctag tctttttct ctctgtggaa tggtgaaaga
5161 gagatgccgt gttgaaag taagatgatg aaatgaatt ttaattcaag aaacattcag
5221 aaacatagga attaaact agagaaatga tctaatttcc ctgttcacac aaactttaca
5281 cttaatctg atgattgat atttattt agtgaaacat catcttgtta gctaactta
5341 aaaaatgat gtagaatgat taaaggttgg tatgatttt tttaatgta tcagtttgaa
5401 cctagtcatc ttagaccatt tctgtctca gtatttaaa agcaaaaag gaatggaga
5461 aaattgcatc ttagaccatt tttatatgca gtgtacaatt tgctgggcta gaaatgagat
5521 aagattatt tattttgtt catatcttgt acttttctat taaaatcat ttatgaatc
5581 caaaaaaaaa aaaaaaaa
```

```
  1 magsamsskf flvalaiffs faqvvieans wwslgmnnpv qmsevyiiga qplcsqlagl
 61 sqqqkkichl yqdhmqyige gaktgikecq yqfrhrrwnc stvdntsvfg rvmqigsret
121 aftyavsaag vvnamsracr egelstcgcs raarpkdlpr dwlwggcgdn idygyrfake
181 fvdarereri hakgsyesar ilmnlhnnea grrtvynlad vackchgvsg scslktcwlq
241 ladfirkvgda lkekydsaaa mrlnsrgklv qvnsrfnspt tqdlvyldps pdycvrnest
301 gslgtggrlc nktsegmdgc elmccgrgyd qfktvgterc hckfhwccyv kckkcteivd
361 qfvck
```

Figure 12

| SEQ ID NO. | Accession ID | Protein name | Sequence |
|---|---|---|---|
| 9 | NM_014339.6 | IL-17ra | 1 ctgggcccgg gctggaagcc ggaagcgagc aaagtggagc cgactcgaac tccaccgcgg
61 aaaagaaagc ctcagaacgt tcgttcgctg cgtccccagc cggggccgag ccctccgcga
121 cgccagccgg gccatggggc cgcacgcag cccgccgtcc ctgtccccgg gctgtccccg
181 gggcgtgctc ctgctgctcc tgggcgtgct gggcctcctc tgcgcctccc tgcgactcct
241 ggaccaccgg agcctgtctg gctccagcc gggctaaac tgcacggtca agaatagtac
301 ctgcctggat gacagctgga tccacctgcg aaactgacc cctcctccc caaaggacct
361 gcagatccag ctgcactttg cccacacca acaaggagac ctgttcccg tggctcacat
421 cgaatggaca ctgcagacag ctgcagcat cctgtaccctc gaggtgcag agttatctgt
481 cctgcagctg aacaccaatg acgtttgtg cgtcaggttt gagttctgt ccaaactgag
541 gcatcaccac aggcggtggc gttaccctt cagccacttt gtggttgacc ctgaccagga
601 atatgaggtg accgttcacc actgccaa gcccatccct gatgggacc caaaccacca
661 gtccaagaat ttcctgtgc ctgactgtga gcacgccagg atgaaggtaa ccacgccatg
721 catgagctca ggcagcctgt gggacccaa catcaccgtg gagacccgg aggcccacca
781 gctgcgtgtg agcttcacc tgtggaacga acagtgctt gggaccctgg agtcccgg
841 tttccgcac atggagaacc acagtgctt cacacactga cacactct ctgccccag
901 accagagagag ttccaccagc gatcaaccgt cacactcact ctacccaacc ttaaagggtg
961 ctgtcgccac caagtgcaga tccagccctt cttcagcagc tgcctcaatg actgcctcag
1021 acactccgcg actgttcct gcccagaaat gcagacact ccagaaccaa ttccggacta
1081 catgccccctg tgggtgtact ggttcatcac gggcatctcc atcctgctgg tgggctccgt
1141 catctgcctc atcgtctgca aatacacacg ctctcgga gctagctggg cctgaagtg aaaaatacag
1201 tgatgacacc aaatacaccg atggcgtgc tgcgctgac ctgatccc cacccgctga
1261 gccaggaag gtctggatca tctactacgc cgaccaccc ctctacgtgg acgtggtcct
1321 gaaattcgcc cagttcctgc tcaaccgcctg cggcacgggg gtggccctgg acgtgctgga
1381 agagcaggcc atctcggagg caggagtcat gacctgggtg ggccgtcaga agcaggagat
1441 ggtggagagc aactctaaga tcatcgtcct gtgctccg gcacgcgcg ccaagtggca
1501 ggcgtcctg ggccgggg cgctcgtgc gctgctgtgc cctccgcgc gaccacggaa agcccgtggg
1561 ggacctgttc actgcagcca tgaacatgat cttcaggag ctccccggac ttcaagaggc cagcctgctt
1621 cggcacctac gtagtctgct acttcagcga ggtcagctgt gacggcgacg tcccccgacct
1681 gttcggccg gcgcccggt accggcccg catgcacccg gaggagttgt acttccgcat
1741 ccaaggccctg gagatgttcc agcccggcca gctcaccgg gcccggggca gtagggggca tgtcgggga
1801 caactacctg cggaccccga gctcaggca gctccggcgcc gccctggaca gttccggga |

Figure 12 (cont.)

```
1861 ctggcaggtc cgtgtcccg actggttcga atgtgaaac ctctactcag cagatgacca
1921 ggatgcccg tcctgacg aagaggtgtt tgaggagcca ctgctgcctc cggaaccgg
1981 catcgtgaag cgggcccc tggtgcgga gctgctcc caggcctgcc tggccataga
2041 cccgctggtc ggggaggaag gaggagcagc agtgcaaag ctggaactc acctgcagcc
2101 ccggggtcag ccaggcccgc agccctcca cacctggtg ctcgccag aggaggggc
2161 cctgtgggcc gcggtggagc ctggccct gctgacggt gccgcagtcc ggctggcact
2221 ggcgggggag ggcgaggcct gcccgctgct gggcagccg ggcgctggc gaaatagcgt
2281 cctcttcctc ccgtggacc ccgaggact gccccttggc agcagcaccc ccatgcgtc
2341 tcctgacctc cttccagagg acgtgaggga gcacctcgaa ggcttgatgc tctcgtctt
2401 cgagcagagt ctgagctgcc agcccaggg ggctgcagt agacccgcca tggtcctcac
2461 agaccacac acgcctacg aggaggagca gcgcagtca gtgcagtctg accaggcta
2521 catctccagg agtcccccgc agccccccga gggactcacg gaaatggagg aagaggagga
2581 agaggagcag gaccaggga agccccggcc agccggccct gccactctct cccgagacc tggagagcct
2641 gaggagcctc cagcggcagc tgcttttccg ccagctgcag aagaactcgg gctgggacac
2701 gatgggtca gagtcagagg ggccagtgc atgagggcgg ctccccagg accgcccaga
2761 tcccagcttt gagagaggag cgtgtgtgca cgtattcatc tgtgtgtaca tgtctgcatg
2821 tgtatatgtt cgtagttgctt atgtaggctt taaaatgtaa atgtctggat tttaatccca
2881 ggcatccctc ctacttttc tttgtgcagc gtctggtta agctctgttc ccagggaat
2941 ccacacagcc cgctccagg agctaatgt agagcgtcct tgaggtcca ttattcgttc
3001 attcagcatt tattgtgcac ctactatgtg gcggcattt gggataccaa gataaattgc
3061 atgcggcatg gcccagcca gccccaggg taacgctag tgccgaggac acgttaaacg
3121 aacaggatgg gccggcacg gtggtcacg cctgtaatcc cagcacactg ggaggccgag
3181 gcaggtggat cactctgagg tcaggagttt gagccagcct ggccaacatg gtgaaaccc
3241 atctccacta aaatagaaaa aattagccgg gcatgtggac acatgctgt agtcctagct
3301 acttgggagg ctgagcagg agaattgctt cagcctggat gacagacgca gactctatct caaaaaaaaa
3361 gagattgtgc cattgcactg cagcctggat gacagagcga gactctatct caaaaaaaaa
3421 aaaaaaaaaa gatgtcacg cgggatgtaa acgctgaatg gcccaggtgc agtggctcat
3481 gcttgtaatc ccagcactt gggaaggcga ggcaggtgga ttgcttgagc tcaggagttc
3541 aagaccagcc tggcgacat agtgagacct catcctacc taaattttt tttagtcagt
3601 catgtggca catgcctgta gtcccagcta ctcgggaggc tgatgccaga tgatcactg
3661 agcccaggag gtagagctg acccgtctc taatgtgacc attgcaatcc agcctggcca
3721 gcagagttgt gacatgcac aaaaaaaata aaaaagtaga aagatggagt gaagcctgc
3781 ccagggttgt aggattgtgg ttgggaaag cccaggtcag gggatccca cgaggagatg
3841 cctgagctga aggattgtgg gagtgagctt gcaaggaagc gcaagtccca agtttgtggg
3901 taagtgctgg gagtgagtg gagtgagctt gtcagggagc tgtggtgga gcctggaggg
3961 gaaggaggga ggcagtgaga gagatccggg tgggggtgg gggatgtcg ccagagctca
```

Figure 12 (cont.)

```
4021 gggtggga cagccttgtg cgcatcagtc ctgaggcctg gggcacctt cgtctgatga
4081 gcctctgcat ggagagaggc tgagggctaa acacagctgg atgtcacctg agttcattta
4141 taggaagaga gaaatgtcga ggtgaaacgt aaaagcatct gcaggaagg tgagtctgaa
4201 gccctgcacc cgcgttccga ctatcagtgg ggagctgtta gcacgtagga ttcttcagag
4261 cagctgggct ggagctcccc tgagctcagg aagcccagg gtgcaaggc aaggaaatga
4321 gggtggtgg gtcagtgaag atctgggcag accttgtgtg ggggaaggt gctgctgtga
4381 cttcagggtc tgagtccaa agacagcatt tgaaaagagg ctctgaagcc agtgttgaa
4441 gaatttgttc ctgagtgccg tcctggggt agctagagg ctttcgtgctt cagggtcctg
4501 aagaacacat tgaagtgccg tctgacactg gaatagggtg cccttcattc ctatgcctga
4561 gtccttaact atattccaa cctccagtga ggagagaag attcgaaat gtgacaggag
4621 agcaaacagg acagtttgca tgtgtgtgtg cgcacacata catgtcgtg aaagattatc
4681 aataaaagtg cataaatttg ttgatctggt aagagtttct agcaggaag tcgagccact
4741 tactgtaggt caagaagttg ctagttgcgg agttttttct tgcagttaga ctttacctag
4801 tggtagcagg gccaccaaag gccaccaaag cagatgtgt atggcccata atccaccaa
4861 cagcagcaaa ggagagaaca aaggcagaag ggagcagaag ctcccagcc actagcctt
4921 tgggctcagt ctcccaata atcctggaga gggcttcgt tgggtctgga cacctaccat
4981 gcattctgtg acctttccct agcttccaat aaataactgt ttgacgccca gagtacagga
5041 taccacaatg cactctcct ggtagagca catgttccca tctgtccca ttcctcagga
5101 accttgaatt ctagtctgc tggcctttga gccatgcca gtaaatgtcc tgatgggcat
5161 tgcctactat ctccagggca gctgcctttg tcctcctaac agcttattg gagtacagtt
5221 cacttaccat acaatccaca attgaccctg cacaatttga tgccggtta gtatagtcac
5281 agttcagcag ccatcagcag agtcagtctt agagttact accccaaaa gaaatccagc
5341 cccccttagt caccacccca acctcccat cctagccac cctagccta ctttgatctc
5401 tgtagacttg cctcttctgg acatgacata gagaaaggag tcataaattc tccaaggtgt
5461 ctgttcttc tttaatgtca ttccctgttt ctcctcacat tccctcccca tttcctgggc
5521 ccagtctcac actgtcctt gcttaccta aatgctatta attccatcac tctgagtatg
5581 gtgtttgctg tcggtgaat gccaagagct tcaagagtgt gtgtaaataa agccacacct
5641 ttatttttgt attattctga accatgccta ataaattgtt tcaccaagaa atgtctctct
5701 aagaacaggt gccctggg ctgtgccct cccacctctt cagctgtct cctgagtgtg
5761 cagaggtggt tccgtttggg aaagaagcag cggagcatct aaccatgcct gtgtccaggc
5821 cgattatgca cgcgccacc aacaagtcc aacctcccgc gtagagtttc atgacttttt
5881 cctgcctact atctgatcc tagttttttt ctcttttttct ttgttttt ggaataatta
5941 ctttgattca aaaccagttt tgtgttcgg cataggaagg tccttgaag tgtttaggt
6001 ctaaaaaggg tgtgatgaa atccattcag cagttgagc tgggatctct
6061 gaatgcaagg gtatgatga tatactttct tcttgcttt gttgtgttt ggtttttgt
6121 ttgtttttaa gtcaggtct ctctgtcacc agctgtatt acagtggtgc aatcatgct
```

Figure 12 (cont.)

```
6181 cactgcagcc tcgactccc aggctcaagc catctttcca cctcagcctg ccagtggcta
6241 gaactacagg cgtgccacac tgtgccggc taatttgtgt gtatatattt tgtagaaatg
6301 gggtttcacc atgtgtcca ggctggtcac gaactcctgg gctcagcca tctgcccgcc
6361 tcatcctccc aaagtgctgg gattatagcc ctgagccac cgtgctgc ctttcctgtt
6421 tatctttgaa aataaatag ggcataagag agaagaagat agaagaaga gtactacaa tgcagtgggt
6481 gttttaact ctatagcctt tgggctctgt ggttggtgct cccttccta aataaatgag
6541 gtgtatgcag ggccctcttc tgccttagcg ccctgccagc tgggactcca gcaaggcccg
6601 gggcacctga ggacagagtg agatggaggg agaggatcct cgctgctcc agcagcccgg cctgcatccc
6661 acaagtcaac tgtgtcggac agaggatcct tacaaagaag aggcagcagg gttggggct
6721 ggccagctgc tcgtccgccc tggtagctt gtcatctgt aaagtgggtg gggcaggagt
6781 tccacctca tgggtcctg gcaagcctgc agtatcccg agtggcacca gctgcttct
6841 gggcagagc agttgtgcc ccctgagta ccactgatcc tcttccctg ctattaggta
6901 ttgctctctt cctcggttgt ttgccttttc aggaagtaca agattataga agttaatatgt gttcccatat
6961 ttggcgtctc tcaggagctc aggaagtact tggctgagtg aacatgtcca ttgtggaaaa
7021 atggcaacaa tatggattcc atgggtatat tttatagaag aatatgaaga aaagcagcta
7081 cccctaaacc cattgcacaa gctgttcatg ttaattctgt acccgacgct ttcccacgg
7141 ggcctccct cactctgaaa tggcatccag gtccatcttg ccctcacct ctgcatgcct
7201 ctccatgccc catccctct cccagatcct agcactggt ccaactctc gccctgtcca
7261 tttaggttga tgaaagcagg cagtcaccg gtgggccag tcttcctgt gggaggaaca
7321 tgcagtctcc tgtccatgg tttgaagtgt gcaggaagc ctggccagc ccactcccc
7381 ctggagtcct tcccaggagg aataaccct tgagacagca taggtcattg actataagat gagttcgctc
7441 actgatcct tcctcctga agaaggagt adaaggtaca agaagtaca cagtgaccag gtaggaggag
7501 gagagggagt agaaaggagg catgcgggtg gctgtgtccc gcattgcct gcttccctgc
7561 acgggtgtcc cactggccgc ctctgctcac cagtgtcatg ggatctctc agaagatgaa
7621 aacagcccct gcttttttgc tagaatggct gagcttcat ggaaggaag ctgaccca
7681 gcaacagccg actaccgaag gttgcctgaa gcagtgcaga tgtggagga agaagggct
7741 tggtgcacac tgctttct tcctgactgc aatgtggcat tgtgcagct acctcctctt
7801 tctcggcctc aggaaatgg agagaaagca gccctgaagg tggctgtgac gagggaaggg
7861 gcagaggggcc tgacagtcaa ccacgcgcta tattttcctg ttcttcctta gggcaagaac
7921 tgcatggcca gactcaggca aggcctaggt gtgggctggg cattgcctt acgtgaagag
7981 atcactccgc gtccctactg caccctgtcac aaagtgctt ctgatatgcc tgcaaacca
8041 aaatcggtga gccagcgtt gcttccctag aagacattc taaatattca taacatgtt
8101 gctcaaatca atcaccttat tttacatccg ctccaggag aaatgaagac atggtcctac
8161 gttgttctgt aattatttc tatgtaaatt ttgttcctg ttacattat atatgtctta
8221 gggaaagga ccattcaca tgtgtcacct catgcattc tcaccacage cctgtgattg
8281 ctcctgttt ataaataatg acatagttcc agttgatggc caaaccaca gctaaacgaga
```

Figure 12 (cont.)

| 10 | NP_001276834.1 | IL-17ra | |
|---|---|---|---|

```
8341 ggcagagaga gctcaggctc ccaggagctt ccactctcag acttgcctc ccgggctgcc
8401 ctgagtgaaa cgcctgctta gcatttggca gcaagctggca cagccagaag cagcaagcta gggtcacaac
8461 acagagaggg gctgtgtaat actgctgcc tctgtgctaa gaaaaaaaa aaatcactgt
8521 gtgtttgttt atttggtgc agcccagtg ttcttgctta gacttaatac taccttcat
8581 gttaaaataa aaccaaacaa aaacccat 1 mgaarsppsa vpgpilglil lllgvlapgg aslrlldhra lvcsqpginc tvknstcidd
 61 swihprnltp sspkdlqigl hfahtgcgdl fpvahiewtl qtdasilyle gaelsvlqln
121 tnerlcvrfe flskirhhhr rwrftfshfv vdpdqeyevt vhhipkpipd gqpnhqsknf
181 lvpdceharm kvttpcmssg slwdpnitve tleahqlrvs ftlwnesthy qilltsfphm
241 enhscfehmh hipaprpeef hqrsnvtltl rnlkgccrhq vqigpffssc lndclrhsat
301 vscpempdtp epipgpgsek ysddtkytdg lpaadlippp lkprkvwily sadhplyvdv
361 vlkfagfllt acgtevaldl leegaiseag vmtwvgrqkq emvesnskii vlcsrgtrak
421 wqaligrgap vrlrcdhgkp vgdlftaamn milpdfkrpa cfgtyvvcyf sevscdgdvp
481 dlfgaapryp lmdrfeevyf riqdlemfqp grmhrvgels gqnylrspgg rqlraaldrf
541 rdwqvrcpdw fecenlysad dqdapsldee vfeeplippg tglvkraplv reppgsqacla
601 idplvqeegg aavaklephl qprgqpapcp lhtlvlaaee galvaavepg pladgaavri
661 alageqeacp llgspqagrn svlflpvdpe dsplqsstpm aspdlipedv rehleglmls
721 ifeqslscqa qggcsrpamv ltdphtpyee eqrgsvqsdq gyisrsspqp pegitemeee
781 eeeeqdpgkp alplspedie slrslqrqll frqlqknsgw dtmgsesegp sa
```

Figure 13

| SEQ ID NO. | Accession ID | Protein name | Sequence |
|---|---|---|---|
| 11 | NM_002190.2 | IL-17a | 1 gcaggcacaa actcatccat cccagttga ttgaagaaa caacgatgac tcctgggaag<br>61 acctcattgg tgtcactgct actgctgctg agcctggagg ccatagtgaa ggcaggaatc<br>121 acaatcccac gaaatccagg atgcccaaat tctgaggaca agaacttccc ccggactgtg<br>181 atggtcaacc tgaacatcca taaccggaat accaatacca atcccaaaag gtcctcagat<br>241 tactacaacc gatccaactc acctggaat ctccaccgca atgaggacc tgagagatat<br>301 ccctctgtga tctgggagc aaagtgcgc cactggct gatcaacgc tgatggaac<br>361 gtggactacc acatgaactc tgtcccatc cagcaagaga tcctggtcct gcgcagggag<br>421 cctccacact gcccaactc ctccgctg gagaagatac tggtgtcgt gggctgcacc<br>481 tgtgtcaccc cgattgtcca ccatgtggcc ccatggtctc taagagctct gggagccca cactcccaa<br>541 agcagttaga ctatgggag ccgaccagc ccctcatcct ttgtccatt aaagcttcag<br>601 cctcatttcg gactaaactc attagagttc ttaaggcagt ttgtccaatt aaagcttcag<br>661 agtaacact tggccaagat atgagatctg aattacttc cctctttcc aagaaggaag<br>721 gtttgactga gtaccaattt gcttctgtt tacttttta agggctttaa gttatttatg<br>781 tatttaatat gccctgagat aacttgggg tataagattc cattttaatg aattacctac<br>841 tttattttgt ttgtctttt aaagaagata agattctggg cttggaatt atttatgttt aagtatttta<br>901 aaagtgaaa cctgtattta tttgagctat ttaagatct atttatgttt aagtatttag<br>961 aaaaggtga aaagcacta ttatcagttc tgcctaggta aatgtaagat agaattaaat<br>1021 ggcagtgcaa aatttctgag tctttacaac atacggatat agtatttct cctctttgtt<br>1081 tttaaaagtt ataacatggc tgaaaagaaa gattaaacct actttcatat gtattaattt<br>1141 aaattttgca atttgttgag gttttacaag agatacagca agtctaactc tctgttccat<br>1201 taaaccctta tataaaatc cttcgtaat aataaagttt caaaagaaaa tgtttatttg<br>1261 ttctcattaa atgtatttta gcaaattcag ctctccccta ttgggaagag ttatgcaaat<br>1321 tctcctataa gcaaaacaaa gcatgtcttt gagtaacaat gacctgaaa taccccaaat<br>1381 tccaagttct cgattcaca tgcctcaag actgaaccacc gactaaggtt ttcatactat<br>1441 tagccaatgc tgtagacaga agcattttga taggaataga gcaaataaga taatgccct<br>1501 gaggaatggc atgtcattat taaagatcat atgggaaaa tgaaccctc cccaaaatac<br>1561 aagaagttct gggagaac attgcttca gacccctca gactacaatg tccagtttct ccctagact<br>1621 caggcttcct ttggagatta aggccctca gagatcaaca gatcaaca tttctcttcc<br>1681 tcaagcaaca ctcctagggc ctggcttctg acttaagta gtcaacaca acccagaaag<br>1741 gagctgatgg ggcagaacga acttaagta tgagaaagt taaaataaa<br>1801 actcaatcac attcaattcc agagtagttc caagtttcac atcgtaacca tttcgccc |

Figure 13 (cont.)

| 12 | NP_002181.1 | IL-17a | 1 mtpgktslvs lllislseai vkagitiprn pgcpnsedkn fprtvmvnln ihnrntntnp<br>61 krssdyynrs tspwnlhrne dperypsviw eakcrhlgci nadgnvdyhm nsvpiqqeil<br>121 vlrrepphcp nsfrlekilv svgctcvtpi vhhva |

METHODS AND COMPOSITIONS FOR MODULATING ERYTHROPOIESIS

RELATED APPLICATIONS

This application is a § 371 national-stage application based on PCT/US17/051581 filed Sep. 14, 2017 which claims the benefit of priority to U.S. Provisional Application No. 62/394570 filed Sep. 14, 2016, each of which is hereby incorporated by reference in its entirety.

GOVERNMENT INTEREST

This invention was made with Government support under National Institutes of Health Grant R01DK100915. The Government has certain rights in the invention.

BACKGROUND

To date, there are only a small number of erythropoiesis stimulating agents available for therapy, limited to derivatives of the hormone erythropoietin (Epo), iron supplements, and corticosteroids, agents to which resistance or contraindication is not uncommon. These agents are used in anemia of various etiologies including kidney disease, myelodysplastic syndrome, and anemia associated with chronic inflammatory disease. For anemia associated with cancer, where Epo was previously used effectively to treat anemia, it is now contraindicated, since it was found to increase mortality. There is also a shortage of erythropoiesis suppressing agents, a class of agents that is not generally used clinically but could be useful in the treatment of the premalignant syndrome Polycythemia Vera or in inherited primary erythrocytosis syndromes.

The shortage of erythropoiesis stimulating and suppressing agents reflects the paucity of tools available today for the study of early erythropoiesis. There have been no strategies that systematically identify the entire cellular and molecular trajectory of the early erythroid lineage.

SUMMARY

In certain aspects, disclosed herein are novel compositions and methods related to either the enhancement or inhibition of erythropoiesis that are useful, for example, in the treatment of anemia or erythrocytosis.

In some aspects, the methods provided herein relate to the stimulation of erythropoiesis in a subject (e.g., a human subject). In some embodiments, provided herein is a method of stimulating erythropoiesis in a subject with anemia comprising administering to the subject an agent that binds to MST1r and/or induces or inhibits MST1r activity (e.g., a MSP ligand protein or a fragment thereof). In some embodiments, provided herein is a method of stimulating erythropoiesis in a subject with anemia comprising administering to the subject an agent that binds to IL-I7ra (e.g., a IL-17a protein or a fragment thereof, a IL-17f protein or a fragment thereof, or a heterodimeric IL-17a/f ligand) In some embodiments, provided herein is a method of stimulating erythropoiesis in a subject with anemia comprising administering to the subject an agent that inhibits the binding of WNT5a to RYK and/or inhibits WNT5a and/or RYK expression or activity.

In certain aspects, the methods provided herein relate to the inhibition of erythropoiesis in a subject (e.g., a human subject). In some embodiments, provided herein is a method of inhibiting erythropoiesis in a subject with erythrocytosis comprising administering to the subject an agent that that inhibits the binding of MSP to MST1r and/or inhibits MST1r and/or MSP expression or activity. In some embodiments, provided herein is a method of inhibiting erythropoiesis in a subject with erythrocytosis comprising administering to the subject an agent that binds RYK and/or induces RYK activity (e.g., a WNT5a protein or a fragment thereof). In some embodiments, provided herein is a method of inhibiting erythropoiesis in a subject with erythrocytosis comprising administering to the subject an agent mat that inhibits the binding IL-17a to IL-17ra and/or IL-17a expression or activity.

In certain aspects, provided herein are agents (e.g., polypeptide agents, small molecule agents, antibody agents and/or inhibitory nucleic acid agents) useful in the methods disclosed herein, as well as pharmaceutical compositions comprising such agents and methods of identifying such agents.

In certain aspects, provided herein are methods of expanding or propagating erythroid progenitor cells in vitro comprising supplementing or adding an agent that activates IL-17ra to a cell medium comprising the progenitor cells. In some embodiments, provided herein are methods of expanding or propagating erythroid progenitor cells in vitro comprising supplementing or adding an agent that inhibits Ryk and/or Mst1r to a cell medium comprising the progenitor cells.

BRIEF DESCRIPTION OF THE DRAWINGS

FIG. 7 shows CFUe and BFU-e (early and late) assay results for ligands—MSP, WNT5a, and IL-17a.

FIG. 8 shows exemplary nucleic acid and amino acid sequences of MST1r.

FIG. 9 shows exemplary nucleic acid and amino acid sequences of MSP.

FIG. 10 shows exemplary nucleic acid and amino acid sequences of RYK.

FIG. 11 shows exemplary nucleic acid and amino acid sequences of WNT5a.

FIG. 12 shows exemplary nucleic acid and amino acid sequences of IL-17ra.

FIG. 13 shows exemplary nucleic acid and amino acid sequences of IL-17a.

Representative of two experiments. Panel g shows a western blot showing IL-17Ra, peak expression in P2/EEP cells and dropping in P1/CEP and in the granulocytic branch (which contributes most of the CD55− cells), consistent with the SPRING plots in (Panel a). Panel h shows a summary of effects of growth factor regulators described herein on erythroid output.

Figure 16:
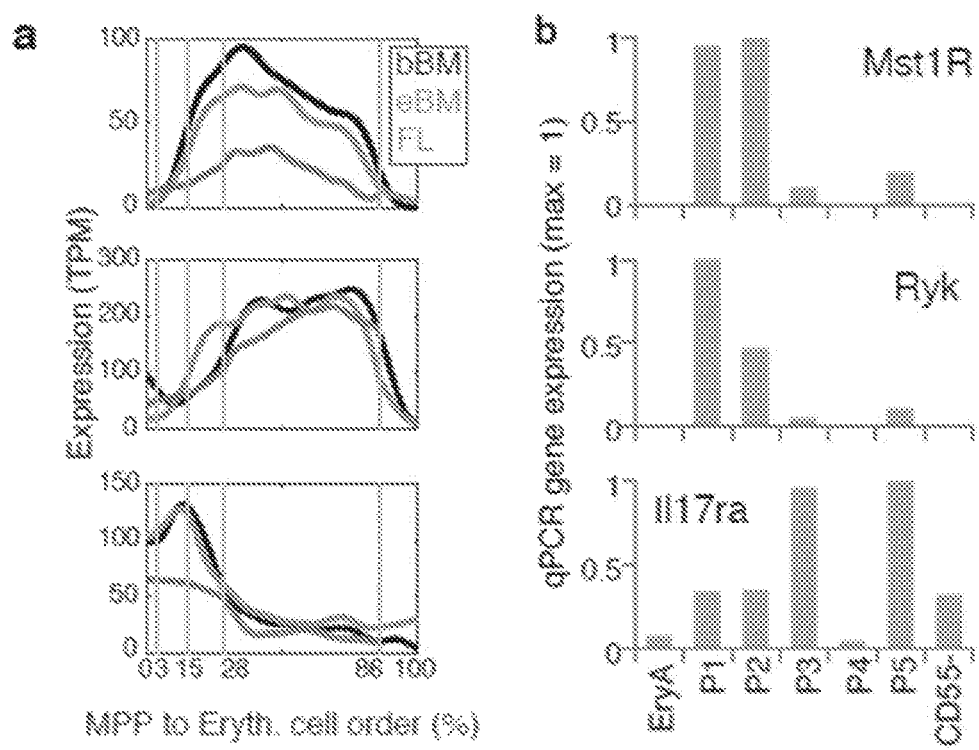

FIG. 16 has two panels (a-b), and shows the localized gene expression and functional response of the erythroid lineage to stimulation of Mst1, Ryk and IL-17Ra. Panel a shows predicted expression of Mst1r, Ryk and Il17ra as assessed by the smoothed scRNA-Seq gene expression on cells arranged along the erythroid trajectory in basal bone marrow (BM), fetal liver (FL) and endosteal bone marrow (eBM). Panel b shows expression of Mst1r, Ryk and Il17ra in basal BM as measured by RT-qPCR.

DETAILED DESCRIPTION

General

In certain aspects, provided herein are novel compositions and methods for the enhancement or inhibition of erythropoiesis and/or for the treatment of anemia or crythrocytosis.

Disclosed herein are three previously unappreciated growth factor receptors found to regulate erythropoiesis, which were identified by searching for receptors expressed in early erythropoiesis through a single cell RNA-Seq reconstruction of the hematopoietic lineage and validated by in vitro erythroid colony-forming-unit and burst-forming unit assays, in mouse fetal liver and in mouse adult bone marrow.

As disclosed herein, three target receptors were identified that are expressed at high levels in early erythroid progenitors: RYK, MST1r and IL-17ra. The ligands of these receptors, WNT5a, MSP and IL-17a (to RYK, MST1r and IL-17ra respectively), interact with erythropoietin (Epo), an essential erythroid cytokine, to either stimulate or inhibit erythropoiesis, as established by colony formation assays and described below. For example, in the fetal liver, MSP interacting with MST1r was determined to enhance erythropoiesis in the context of low erythropoietin concentrations (e.g., 50 mU/ml or less), but inhibit erythropoiesis in the context of high erythropoietin concentrations (e.g., greater than 100 mU/ml). MSP also demonstrated an inhibitory effect in the bone marrow As demonstrated herein. WNT5a ligand (through its interaction with RYK) is a consistent and potent inhibitor of all erythroid colony formation in both fetal liver and bone marrow. What is more, as shown herein, IL-17a, through its interaction with IL-17ra, potentiates bone marrow erythropoiesis.

Accordingly, in certain aspects, disclosed herein are novel compositions and methods for the enhancement or inhibition of erythropoiesis and/or for the treatment of anemia or crythrocytosis through the stimulation or inhibition of RYK. MST1r and IL-17ra and their associated ligands, WNT5a, MSP and IL-17a, respectively. Also disclosed herein are novel compositions and methods for the treatment of anemia through the stimulation of IL-17ra by IL-17a, IL-17f, or by heterodimeric IL-17a/f ligands.

In some aspects, disclosed herein are methods of expanding or propagating erythroid progenitor cells in vitro comprising supplementing or adding an agent that activates IL-17ra and/or an agent that inhibits Ryk or Mst1r to a cell medium comprising the progenitor cells.

Definitions

For convenience, certain terms employed in the specification, examples, and appended claims are collected here.

As used herein, the term "administering" means providing a pharmaceutical agent or composition to a subject, and includes, but is not limited to, administering by a medical professional and self-administering.

The term "agent" is used herein to denote a chemical compound, a small molecule, a mixture of chemical compounds and/or a biological macromolecule (such as a nucleic acid, an antibody, an antibody fragment, a protein or a peptide). Agents may be identified as having a particular activity by screening assays described herein below. The activity of such agents may render them suitable as a "therapeutic agent" which is a biologically, physiologically, or pharmacologically active substance (or substances) that acts locally or systemically in a subject.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of the foregoing.

As used herein, the tem. "antibody" may refer to both an intact antibody and an antigen binding fragment thereof. Intact antibodies are glycoproteins that include at least two heavy (H) chains and two light (L) chains inter-connected by disulfide bonds. Each heavy chain includes a heavy chain variable region (abbreviated herein as $V_H$) and a heavy chain constant region. Each light chain includes a light chain variable region (abbreviated herein as $V_L$) and a light chain constant region. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. The term "antibody" includes, for example, monoclonal antibodies, polyclonal antibodies, chimeric antibodies, humanized antibodies, human antibodies, multispecific antibodies (e.g., bispecific antibodies), single-chain antibodies and antigen-binding antibody fragments. An "isolated antibody," as used herein, refers to an antibody which is substantially free of other antibodies having different antigenic specificities. An isolated antibody may, however, have some cross-reactivity to other, related antigens.

The terms "antigen binding fragment" and "antigen-binding portion" of an antibody, as used herein, refers to one or more fragments of an antibody that retain the ability to bind to an antigen. Examples of binding fragments encompassed within the term "antigen-binding fragment" of an antibody include Fab, Fab', F(ab=)$_2$, Fv, scFv, disulfide linked Fv, Fd, diabodies, single-chain antibodies, NANO-BODIES®, isolated CDRH3, and other antibody fragments that retain at least a portion of the variable region of an intact antibody. These antibody fragments can be obtained using conventional recombinant and/or enzymatic techniques and can be screened for antigen binding in the same manner as intact antibodies.

The terms "CDR", and its plural "CDRs", refer to a complementarity determining region (CDR) of an antibody or antibody fragment, which determine the binding character of an antibody or antibody fragment. In most instances, three CDRs are present in a light chain variable region (CDRL1, CDRL2 and CDRL3) and three CDRs are present in a heavy chain variable region (CDRH1, CDRH2 and CDRH3). CDRs contribute to the functional activity of an antibody molecule and are separated by amino acid sequences that comprise scaffolding or framework regions. Among the various CDRs, the CDR3 sequences, and particularly CDRH3, are the most diverse and therefore have the strongest contribution to antibody specificity. There are at least two techniques for determining CDRs: (1) an approach based on cross-species sequence variability (i.e., Kabat et al., Sequences of Proteins of Immunological Interest (National Institute of Health, Bethesda, Md. (1987), incorporated by reference in its entirety); and (2) an approach based on crystallographic studies of antigen-antibody complexes (Chothia et al., Nature, 342:877 (1989), incorporated by reference in its entirety).

As used herein, the term "humanized antibody" refers to an antibody that has at least one CDR derived from a mammal other than a human, and a FR region and the constant region of a human antibody. A humanized antibody is useful as an effective component in a therapeutic agent since antigenicity of the humanized antibody in human body is lowered, The term "isolated polypeptide" refers to a polypeptide, in certain embodiments prepared from recombinant DNA or RNA, or of synthetic origin, or some combination thereof, which (1) is not associated with proteins that it is normally found with in nature, (2) is isolated from the cell in which it normally occurs, (3) is isolated free of other proteins from the same cellular source, (4) is expressed by a cell from a different species, or (5) does not occur in nature.

The term "isolated nucleic acid" refers to a polynucleotide of genomic, cDNA, or synthetic origin or some combination thereof, which (1) is not associated with the cell in which the "isolated nucleic acid" is found in nature, or (2) is operably linked to a polynucleotide to which it is not linked in nature.

As used herein, the term "monoclonal antibody" refers to an antibody obtained from a population of substantially homogeneous antibodies that specifically bind to the same epitope, i.e., the individual antibodies comprising the population are identical except for possible naturally occurring mutations that may be present in minor amounts. The modifier "monoclonal" indicates the character of the antibody as being obtained from a substantially homogeneous population of antibodies, and is not to be construed as requiring production of the antibody by any particular method.

The terms "polynucleotide", and "nucleic acid" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified, such as by conjugation with a labeling component. The term "recombinant" polynucleotide means a polynucleotide of genomic, cDNA, semisynthetic, or synthetic origin which either does not occur in nature or is linked to another polynucleotide in a non-natural arrangement.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body As used herein, "specific binding" refers to the ability of an antibody to bind to a predetermined antigen or the ability of a polypeptide to bind to its predetermined binding partner. Typically, an antibody or polypeptide specifically binds to its predetermined antigen or binding partner with an affinity corresponding to a Ku of about $10^{-7}$ M or less, and binds to the predetermined antigen/binding partner with an affinity (as expressed by $K_D$) that is at least 10 fold less, at least 100 fold less or at least 1000 fold less than its affinity for binding to a non-specific and unrelated antigen/binding partner (e.g., BSA, casein).

As used herein, the term "subject" means a human or non-human animal selected for treatment or therapy.

The phrases "therapeutically-effective amount" and "effective amount" as used herein means the amount of an agent which is effective for producing the desired therapeutic effect in at least a sub-population of cells in a subject at a reasonable benefit/risk ratio applicable to any medical treatment.

"Treating" a disease in a subject or "treating" a subject having a disease refers to subjecting the subject to a pharmaceutical treatment, e.g., the administration of a drug such that at least one symptom of the disease is decreased or prevented from worsening.

Erythropoiesis Modulating Proteins

In certain embodiments, the compositions and methods provided herein relate to three erythropoiesis-modulating receptors, MST1r, RYK and IL-17ra, as well as their associated ligands, MSP, WNT5a and IL-17a, respectively. Additional ligands for IL-17a include IL-17f and heterodimeric IL-17a/f ligands.

MST1r (macrophage stimulating 1 receptor/RON kinase) is a receptor tyrosine kinase (RTK) expressed in multiple tissues and tumors. As disclosed herein, engagement of MST1r by its ligand MSP inhibits bone marrow erythropoiesis. It also stimulates fetal liver erythropoiesis in the presence of low Epo concentrations (Epo at less than 100 mU/ml). Thus, agents that inhibit MST1r (e.g., an agent that directly disrupts the interaction between MST1r and MSP, such as an MST1r-specific or MSP-specific antibody and/or an agent that inhibits MST1r and/or MSP expression, such as an MST1r-specific and/or MSP-specific inhibitory nucleic acid) can enhance erythropoiesis when administered to anemic adult subjects. Agents that activate MST1r (e.g., such as MSP and/or MST1r binding fragments thereof) can inhibit erythropoiesis when administered to subjects with erythrocytosis (e.g., subjects with polycythemia vera). Exemplary MST1r nucleic acid and amino acid sequences are provided in FIG. 8 (SEQ ID NOs: 1 and 2, respectively). Exemplary MSP nucleic acid and amino acid sequences are provided in FIG. 9 (SEQ ID NOs: 3 and 4, respectively).

Figure 11:
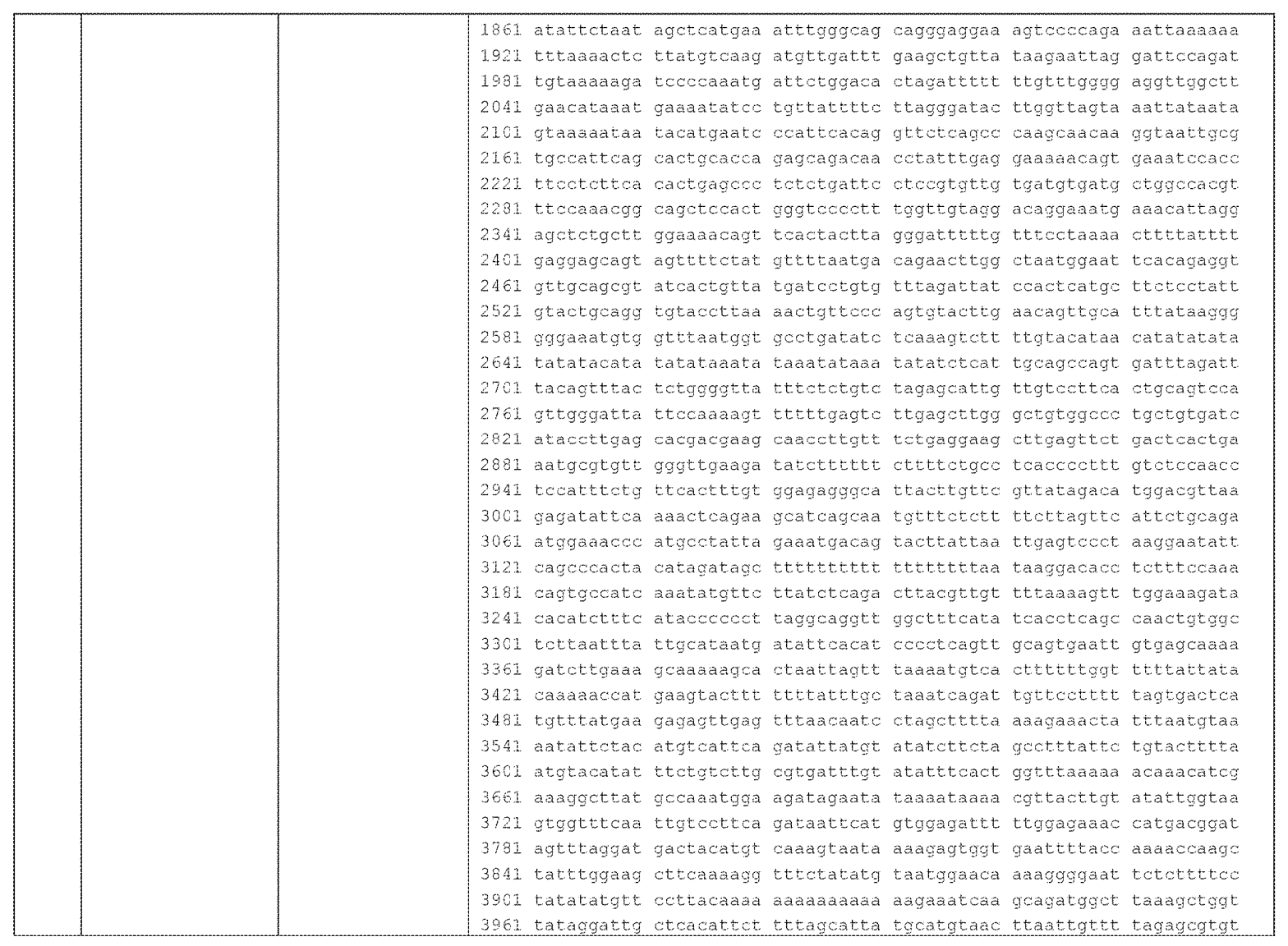

RYK belongs to the receptor tyrosine kinase (RTK) family but has an inactive kinase domain and functions in non-canonical Wnt signal transduction. As disclosed herein, engagement of RYK by its ligand WNT5a inhibits erythropoiesis. Thus, agents that activate RYK (e.g., such as WNT5a and/or RYK binding fragments thereof) can inhibit erythropoiesis when administered to subjects with erythrocytosis (e.g., subjects with polycythemia vera). Agents that inhibit the interaction between RYK and WNT5a (e.g., an agent that directly disrupts the interaction between RYK and WNT5a, such as an RYK-specific or WNT5a-specific antibody and/or an agent that inhibits RYK and/or WNT5a expression, such as a RYK-specific and/or WNT5a-specific inhibitory nucleic acid) can enhance erythropoiesis when administered to anemic subjects. Exemplary RYK nucleic acid and amino acid sequences are provided in FIG. 10 (SEQ ID NOs: 5 and 6, respectively). Exemplary WNT5a nucleic acid and amino acid sequences are provided in FIG. 11 (SEQ ID NOs: 7 and 8, respectively), IL-17ra is one of several receptors for the IL-17 proinflammatory cytokines, which have been reported to be broadly inhibitory on certain bone-marrow progenitors, though the expression of an IL-17 receptor on erythroid progenitors had not been previously documented. As disclosed herein, engagement of IL-17ra by its ligand IL-17a enhances erythropoiesis. Thus, agents that activate IL-17ra (e.g., such as IL-17ra agonists, IL-17a, IL-1.7f, heterodimeric IL-17a/f ligands and/or IL-17ra binding fragments and/or variants thereof) can enhance erythropoiesis when administered to anemic subjects. Agents that inhibit the interaction between IL-17ra and IL-17a (e.g., an agent that directly disrupts the interaction between IL-17ra and IL-17a, such as an IL-17ra-specific or IL-17a-specific antibody and/or an agent that inhibits IL-17ra and/or IL-17a expression, such as a IL-17ra-specific and/or IL-17a-specific inhibitory nucleic acid, or an antagonist of IL-17a) can inhibit erythropoiesis when administered to subjects with erythrocytosis (e.g., subjects with polycythemia vera). Exemplary IL-17ra nucleic acid and amino acid sequences are provided in FIG. 12 (SEQ ID NOs: 9 and 10, respectively). Exemplary IL-17a nucleic acid and amino acid sequences are provided in FIG. 13 (SEQ ID NOs: 11 and 12, respectively).

In certain embodiments, provided herein are ligand-binding polypeptide fragments of a receptor. Such polypeptides can be useful, for example, for inhibiting the interaction between the respective ligand and receptor as well as for identifying agents that bind to the receptor at the same epitope as the ligand. In some embodiments, provided herein are receptor-binding polypeptide fragments of a ligand described herein. Such polypeptides can be useful, for example, for activating the receptor or for inhibiting the interaction between the respective ligand and receptor as well as for identifying agents that bind to the ligand at the same epitope as the receptor.

In some embodiments, the polypeptides and proteins described herein can be isolated from cells or tissue sources by an appropriate purification scheme using standard protein purification techniques. In another embodiment, polypeptides and proteins described herein are produced by recombinant DNA techniques. Alternatively, polypeptides described herein can be chemically synthesized using standard peptide synthesis techniques.

In some embodiments, polypeptides and proteins described herein comprise an amino acid sequence substantially identical SEQ ID NO: 2, 4, 6, 8, 10 or 12. Accordingly, in another embodiment, the polypeptides and proteins described herein comprise an amino acid. sequence at least about 80%, 85%, 90%, 91%, 92%, 93%, 94%, 95%, 96%, 97%, 98% or 99% or more identical to SEQ ID NO: 2, 4, 6, 8, 10 or 12.

In certain embodiments, the polypeptides and proteins described herein comprise an amino acid identical to SEQ ID NO: 2, 4, 6, 8, 10 or 12 except for 1 or more (e.g., 1, 2, 3, 4, 5, 6, 7, 8, 9, 10 or more) conservative sequence modifications. As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues of the polypeptides described herein can be replaced with other amino acid residues from the same side chain family and the altered antibody can be tested for retained function using the functional assays described herein.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

In some embodiments, provided herein are chimeric or fusion proteins. As used herein, a "chimeric protein" or "fusion protein" comprises a polypeptide or protein described herein (e.g., those comprising SEQ ID NO: 2, 4, 6, 8, 10 or 12) linked to a distinct polypeptide to which it is not linked in nature. For example, the distinct polypeptide can be fused to the N-terminus or C-terminus of the polypeptide either directly, through a peptide bond, or indirectly through a chemical linker. In some embodiments, the peptide described herein is linked to an immunoglobulin constant domain (e.g., an IgG constant domain, such as a human IgG constant domain).

A chimeric or fusion polypeptide described herein can be produced by standard recombinant I)NA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, Ausubel et al., eds., John Wiley & Sons: 1992). Moreover, many expression vectors are commercially available that already encode a fusion moiety.

The polypeptides and proteins described herein can be produced in prokaryotic or eukaryotic host cells by expression of polynucleotides encoding a polypeptide(s) described herein. Alternatively, such peptides can be synthesized by chemical methods. Methods for expression of heterologous polypeptides in recombinant hosts, chemical synthesis of polypeptides, and in vitro translation are well known in the art and are described further in Maniatis et al., Molecular Cloning: A Laboratory Manual (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Merrifield, J. (1969) J. Am. Chem. Soc. 91:501; Chaiken I. M. (1981) CRC Crit. Rev. Biochem. 11:255; Kaiser et al. (1989) Science 243:187; Merrifield, B. (1986) Science 232:342; Kent, S. B. H. (1988) Annu. Rev. Biochem. 57:957; and Offord, R. E. (1980) Semisynthetic Proteins, Wiley Publishing, which are incorporated herein by reference.

Polypeptide Agents

In certain embodiments, a polypeptide agent is used in the methods and compositions disclosed herein. In some embodiments, the polypeptide agent is an isolated polypeptide comprising a erythropoiesis modulating protein described herein or fraction thereof required to bind to and stimulate its corresponding receptor. In some embodiments, the polypeptide agent comprises an amino acid sequence substantially identical SEQ ID NO: 4, 8 or 12. Accordingly, in another embodiment, the polypeptides agent comprises an amino acid sequence at least about 80%, 85%, 90%, 91%, 92%, 93%, 94%, 95%, 96%, 97%, 98% or 99% or more identical to SEQ ID NO: 4, 8 or 12. In some embodiments, the polypeptide comprises at least 5, 6, 7, 8, 9, 10, 11, 12, 13, 14, 15, 16, 17. 18, 19, 20, 25, 30, 35, 40, 45, 50, 60, 70, 80, 90 or 100 consecutive amino acids of SEQ ID NO: 4, 8 or 12.

In some embodiments, the polypeptide agent comprises an amino acid sequence at least about 80%, 85%, 90%, 91%, 92%, 93%, 94%, 95%, 96%, 97%, 98% or 99% or more identical to the amino acid sequence of a IL-17ra ligand.

In some embodiments, the polypeptide agents disclosed herein can be isolated from cells or tissue sources by an appropriate purification scheme using standard protein purification techniques. In another embodiment, polypeptide agents are produced by recombinant DNA techniques. Alternatively, polypeptides disclosed herein can be chemically synthesized using standard peptide synthesis techniques.

In certain embodiments, the polypeptide agents described herein comprise an amino acid identical to SEQ ID NO: 4, 8 or 12 except for 1 or more (e.g., 1, 2, 3, 4, 5, 6, 7, 8, 9, 10 or more) conservative sequence modifications. As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody by standard techniques known in the art, such as site-directed mutagenesis and. PCR-mediated mutagenesis, Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, prolific, phenylalanine, methionine), beta-branched side chains (e.g., threonine, valine, isoleucine) and aromatic side chains (e.g., tyrosine, phenylalanine, tryptophan, histidine). Thus, one or more amino acid residues of the polypeptides described herein can be replaced with other amino acid residues from the same side chain family and the altered antibody can be tested for retained function using the functional assays described herein.

In some embodiments, the polypeptide agent is a chimeric or fusion proteins. As used herein, a "chimeric protein" or "fusion protein" comprises a polypeptide or protein described herein (e.g., those comprising SEQ ID NO: 4, 8 or 12 or a fragment thereof) linked to a distinct polypeptide to which it is not linked in nature. For example, the distinct polypeptide can be fused to the N-terminus or C-terminus of the polypeptide either directly, through a peptide bond, or indirectly through a chemical linker. In some embodiments, the peptide described herein is linked to an immunoglobulin constant domain (e.g., an IgG constant domain, such as a human IgG constant domain).

The polypeptide agents provided herein can be generated according to any method available in the art. For example, the polypeptide agents can be produced in prokaryotic or eukaryotic host cells by expression of polynucleotides encoding a polypeptide(s) described herein. Alternatively, such peptides can be synthesized by chemical methods. Methods for expression of heterologous polypeptides in recombinant hosts, chemical synthesis of polypeptides, and in vitro translation are well known in the art and are described further in Maniatis et al., Molecular Cloning: A Laboratory Manual (1989), 2nd Ed., Cold Spring Harbor, N. Y.; Berger and Kimmel, Methods in Enzymology, Volume 152, Guide to Molecular Cloning Techniques (1987), Academic Press, Inc., San Diego, Calif.; Merrifield, J. (1969) J. Am. Chem. Soc. 91:501; Chaiken I. M. (1981) CRC Crit. Rev. Biochem. 11:255; Kaiser et al. (1989) Science 243:187; Merrifield, B. (1986) Science 232:342; Kent, S. B. H. (1988) Annu. Rev. Biochem. 57:957; and Offord, R. E. (1980) Semisynthetic Proteins, Wiley Publishing, which are incorporated herein by reference.

Antibody Agents

In certain embodiments, the methods and compositions provided herein relate to antibodies and antigen binding fragments thereof that bind specifically to an erythropoiesis modulating protein described herein. In some embodiments, the antibodies inhibit the interaction between a receptor provided herein and its corresponding ligand. In some embodiments, the antibodies bind to and activate the receptor provided herein. Such antibodies can be polyclonal or monoclonal and can be, for example, murine, chimeric, humanized or fully human.

Polyclonal antibodies can be prepared by immunizing a suitable subject (e.g. a mouse) with a polypeptide antigen e.g., a polypeptide having a sequence of SEQ ID NOs: 2, 4, 6, 8, 10 or 12 or a fragment thereof). The polypeptide antibody titer in the immunized subject can be monitored over time by standard techniques, such as with an enzyme linked immunosorbent assay (ELISA) using immobilized polypeptide. If desired, the antibody directed against the antigen can be isolated from the mammal (e.g., from the blood) and further purified by well-known techniques, such as protein A chromatography to obtain the IgG fraction.

At an appropriate time after immunization, e.g., when the antibody titers are highest, antibody-producing cells can be obtained from the subject and used to prepare monoclonal antibodies using standard techniques, such as the hybridoma technique originally described by Kohler and Milstein (1975) *Nature* 256:495-497) (see also Brown et al. (1981) *J. Immunol.* 127:539-46; Brown et al. (1980) *J. Biol. Chem.* 255:4980-83; Yeh et al. (1976) *Proc. Natl. Acad. Sci.* 76:2927-31; and Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985) *Monoclonal Antibodies and Cancer Therapy*, Alan R. Liss, Inc., pp. 77-96) or trioma techniques. The technology for producing monoclonal antibody hybridomas is well known. (see generally Kenneth. R. H. in *Monoclonal Antibodies: A New Dimension In Biological Analyses*, Plenum Publishing Corp., New York, N.Y. (1980); Lerner, E. A. (1981) *Yale J. Biol. Med.* 54:387-402; Gefter, M. L. et al. (1977) *Somatic Cell Genet.* 3:231-36). Briefly, an immortal cell line (typically a myeloma) is fused to lymphocytes (typically splenocytes) from a mammal immunized with art immunogen as described above, and the culture supernatants of the resulting hybridoma cells are screened to identify a hybridoma producing a monoclonal antibody that binds to the polypeptide antigen, preferably specifically.

As an alternative to preparing monoclonal antibody-secreting hybridomas, a monoclonal specific for a receptor or ligand provided herein can be identified and isolated by screening a recombinant combinatorial immunoglobulin library (e.g., an antibody phage display library or an antibody yeast display library) with the appropriate polypeptide (e.g. a polypeptide having a sequence of SEQ ID NOs: 2, 4, 6, 8, 10 or 12 or a fragment thereof) to thereby isolate immunoglobulin library members that bind the polypeptide.

Additionally, recombinant antibodies specific for a receptor or ligand provided herein, such as chimeric or humanized monoclonal antibodies, can be made using standard recombinant DNA techniques. Such chimeric and humanized monoclonal antibodies can be produced by recombinant DNA techniques known in the art, for example using methods described in U.S. Pat. No. 4,816,567; U.S. Pat. No. 5,565,332; Better et al. (1988) *Science* 240:1041-1043; Liu et al. (1987) *Proc. Natl. Acad. Set. USA* 84:3439-3443; Liu et al. (1987) *J. Immunol,* 139:3521-3526; Sun et al. (1987) *Proc. Natl. Acad Sci.* 84:214-218; Nishimura et al. (1987) *Cancer Res.* 47:999-1005; Wood et al. (1985) *Nature* 314: 446-449; and Shaw et al. (1988) *J. Natl. Cancer Inst.* 80:1553-1559); Morrison, S. L. (1985) *Science* 229:1202-1207; Oi et at. (1986) *Biotechniques* 4:214; Winter U.S. Pat. No. 5,225,539; Jones et at. (1986) *Nature* 321:552-525; Verhoeyan et al. (1988) *Science* 239:1534; and. Beidler et at. (1988) *J. Immunol.* 141:4053-4060.

Human monoclonal antibodies specific for a receptor or ligand provided herein can be generated using transgenic or transchromosoinal mice carrying parts of the human immune system rather than the mouse system. For example, "HuMAb mice" which contain a human immunoglobulin gene miniloci that encodes unrearranged human heavy (μ and γ) and κ light chain immunoglobulin sequences, together with targeted mutations that inactivate the endogenous μ and κ chain loci (Lonberg, N. et al. (1994) Nature 368(6474):856 859). Accordingly, the mice exhibit reduced expression of mouse IgM or κ, and in response to immunization, the introduced human heavy and light chain transgenes undergo class switching and somatic mutation to generate high affinity human IgGK monoclonal antibodies (Lonberg, N. et al. (1994), supra; reviewed in Lonberg, N. (1994) Handbook of Experimental Pharmacology 113:49 101; Lonberg, N. and Huszar, D. (1995) Intern. Rev. Immunol. Vol. 13: 65 93, and Harding, F. and Lonberg, N. (1995) Ann. N. Y Acad. Sci 764:536 546). The preparation of HuMAb mice is described in Taylor, L. et al. (1992) Nucleic Acids Research 20:6287 6295; Chen, J. et al. (1993) International Immunology 5:647 656; Tuaillon et al. (1993) Proc. Nail. Acad. Sci USA 90:3720 3724; Choi et al. (1993) Nature Genetics 4:117 123; Chen. J. et al. (1993) EMBO J. 12: 821 830; Tuaillon et at. (1994) J. Immunol. 152:2912 2920; Lonberg et al., (1994) Nature 368(6474):856 859; Lonberg, N. (1994) Handbook of Experimental Pharmacology 113:49 101; Taylor, L. et al. (1994) International Immunology 6:579 591; Lonberg, N. and Huszar, D. (1995) Intern. Rev. Immunol. Vol. 13:65 93; Harding, F. and Lonberg, N. (1995) Ann. N.Y. Acad. Sci 764:536 546; Fishwild, D. et al. (1996) Nature Biotechnology 14: 845 851. See further, U.S. Pat. Nos. 5,545,806; 5,569,825; 5,625,126; 5,633,425; 5,789,650; 5,877,397; 5,661,016; 5,814,318; 5,874,299; 5,770,429; and 5,545,807.

In certain embodiments, the antibodies provided herein are able to bind to a receptor or ligand described herein with a dissociation constant of no greater than $10^{-6}$, $10^{-7}$, $10^{-8}$ or $10^{-9}$ M. Standard assays to evaluate the binding ability of the antibodies are known in the art, including for example, ELISAs, Western blots and RIAs. The binding kinetics (e.g., binding affinity) of the antibodies also can be assessed by standard assays known in the art, such as by Biacore analysis. In some embodiments, the binding of the antibody to a receptor described herein substantially inhibits the ability of the corresponding ligand to bind to the receptor. In some embodiments, the binding of the antibody to a ligand described herein substantially inhibits the ability of the ligand to hind to the corresponding receptor. As used herein, an antibody substantially inhibits binding of a receptor and a ligand when an excess of polypeptide reduces the quantity of receptor bound to ligand by at least about 20%, 40%, 60% or 80%, 85% or 90% (as measured in an in vitro competitive binding assay).

Small Molecule Agents

Certain embodiments of the methods and compositions disclosed herein relate to methods of enhancing and/or inhibiting erythropoiesis. These methods include administering an agent that inhibits the interaction between a receptor and ligand described herein and/or that stimulates a receptor described herein. Such agents include those disclosed below, those known in the art and those identified using the screening assays described herein. For example, in some embodiments the agent is a RYK inhibitor. Examples of RYK inhibitors include gefitinib (Iressa®), sunitinib (Sutent®; SU11248), erlotinib (Tarcevak; OSI-1774), lapatinib (GW572016; GW2016), canertinib (CI 1033), semaxinib (SU5416), vatalanib (PTK787/ZK222584), sorafenib (BAY 43-9006), imatinib (Gleevec®; STI571), dasatinib (BMS-354825), leflunomide (SU101), vandetanib (Zactima™; ZD6474), pharmaceutically acceptable salts thereof.

In some embodiments, assays used to identify agents useful in the methods described herein include a reaction between an receptor polypeptide disclosed herein (e.g., having a sequence of SEQ ID NO: 2, 6 or 10) or a fragment thereof and/or a ligand polypeptide disclosed herein (e.g., having a sequence of SEQ ID NO: 4, 8 or 12) or a fragment thereof and a test compound. Agents identified via such assays, may be useful, for example, for enhancing or inhibiting erythropoiesis.

Agents useful in the methods disclosed herein may be obtained from any available source, including systematic libraries of natural and/or synthetic compounds. Agents may also be obtained by any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al., 1994, *J. Med. Chem.* 37:2678-85); spatially addressable parallel solid phase or solution phase libraries, synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, Anticancer Drug Des. 12:145).

Examples of methods for the synthesis of molecular libraries can be found in the art, for example in: DeWitt et al. (1993) *Proc. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of agents may be presented in solution (e.g., Houghten, 1992, *Biotechniques* 13:412-421), or on heads (Lam, 1991, *Nature* 354:82-84), chips (Fodor, 1993, *Nature* 364:555-556), bacteria and/or spores, (Ladner, U.S. Pat. No. 5,223,409), plasmids (Cull et al, 1992, *Proc Natl Acad Sci USA* 89:1865-1869) or on phage (Scott and Smith, 1990, *Science* 249:386-390; Devlin, 1990, *Science* 249:404-406; Cwirla et al, 1990, *Proc. Natl. Acad. Sci.* 87:6378-6382; Felici, 1991, *J. Mol. Biol.* 222:301-310; Ladner, supra.), Agents useful in the methods disclosed herein may be identified, for example, using assays for screening candidate or test compounds which inhibit complex formation between a receptor provided herein and a ligand described herein.

The basic principle of the assay systems used to identify compounds that inhibit complex formation between a receptor provided herein and a ligand described herein involves preparing a reaction mixture containing a receptor provided herein or fragment thereof and a ligand described herein or fragment thereof under conditions and for a time sufficient to allow the receptor provided herein or fragment thereof to form a complex with the ligand described herein or fragment thereof. In order to test an agent for modulatory activity, the reaction mixture is prepared in the presence and absence of the test compound, The test compound can be initially included in the reaction mixture, or can be added at a time subsequent to the addition of the ligand described herein or fragment thereof and the receptor provided herein or fragment thereof. Control reaction mixtures are incubated without the test compound or with a placebo. The formation of any complexes between the ligand described herein or fragment thereof and the receptor provided herein or fragment thereof is then detected. The formation of a complex in the control reaction, but less or no such formation in the reaction mixture containing the test compound, indicates that the compound interferes with the interaction of the ligand described herein or fragment thereof and the receptor provided herein or fragment thereof.

The assay for compounds that modulate the interaction of the ligand described herein or fragment thereof and the receptor provided herein or fragment thereof may be conducted in a heterogeneous or homogeneous format. Heterogeneous assays involve anchoring either the ligand described herein or fragment thereof or the receptor provided herein or fragment thereof onto a solid phase and detecting complexes anchored to the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the ligand described herein or fragment thereof and the receptor provided herein or fragment thereof (e.g., by competition) can be identified by conducting the reaction in the presence of the test substance, i.e., by adding the test substance to the reaction mixture prior to or simultaneously with the ligand described herein or fragment thereof and the receptor provided herein or fragment thereof. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the ligand described herein or fragment thereof or the receptor provided herein or fragment thereof is anchored onto a solid surface or matrix, while the other corresponding non-anchored component may be labeled, either directly or indirectly. In practice, microtitre plates are often utilized for this approach. The anchored species can be immobilized by a number of methods, either non-covalent or covalent, that are typically well known to one who practices the art. Non-covalent attachment can often be accomplished simply by coating the solid surface with a solution of the ligand described herein or fragment thereof or the receptor provided herein or fragment thereof and drying. Alternatively, an immobilized antibody specific for the assay component to be anchored can be used for this purpose.

In related assays, a fusion protein can be provided which adds a domain that allows one or both of the assay components to be anchored to a matrix. For example, glutathione-S-transferase/marker fusion proteins or glutathione-S-transferase/binding partner can be adsorbed onto glutathione sepharose beads (Sigma Chemical. St. Louis, Mo.) or glutathione derivatized microtiter plates, which are then combined with the test compound or the test compound and either the non-adsorbed the ligand described herein or fragment thereof or the receptor provided herein or fragment thereof, and the mixture incubated under conditions conducive to complex formation (e.g., physiological conditions). Following incubation, the beads or microtiter plate wells are washed to remove any unbound assay components, the immobilized complex assessed either directly or indirectly, for example, as described above.

A homogeneous assay may also be used to identify inhibitors of complex formation. This is typically a reaction, analogous to those mentioned above, which is conducted in a liquid phase in the presence or absence of the test compound. The formed complexes are then separated from unreacted components, and the amount of complex formed is determined. As mentioned for heterogeneous assay systems, the order of addition of reactants to the liquid phase can yield information about which test compounds modulate (inhibit or enhance) complex formation and which disrupt preformed complexes.

In such a homogeneous assay, the reaction products may be separated from unreacted assay components by any of a number of standard techniques, including but not limited to: differential centrifugation, chromatography, electrophoresis and immunoprecipitation. In differential centrifugation, complexes of molecules may be separated from uncomplexed molecules through a series of centrifugal steps, due to the different sedimentation equilibria of complexes based on their different sizes and densities (see, for example, Rivas, G., and Minton A. P., *Trends Biochem Sci* 1993 August; 18(8):284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the complex as compared to the uncomplexed molecules may be exploited to differentially separate the complex from the remaining individual reactants, for example through the use of ion-exchange chromatography resins. Such resins and chromatographic techniques are well known to one skilled in the art (see, e.g., Heegaard, 1998, *J Mol. Recognit.* 11:141-148; Hage and Tweed, 1997, *J. Chromatogr. B. Biomed. Set. Appl.,* 699:499-525). Gel electrophoresis may also be employed to separate complexed molecules from unbound species (see, e.g., Ausubel et al (eds.), In: *Current Protocols in Molecular Biology*, J. Wiley & Sons, New York. 1999). In this technique; protein or nucleic acid complexes are separated based on size or charge, for example. In order to maintain the binding interaction during the electrophoretic process, nondenaturing gels in the absence of reducing agent are typically preferred, but conditions appropriate to the particular interactants will be well known to one skilled in the art. Immunoprecipitation is another common technique utilized for the isolation of a protein-protein complex from solution (see, e.g., Ausubel et at (eds.), In: *Current Protocols in Molecular Biology*, J. Wiley & Sons. New York. 1999). In this technique, all proteins binding to an antibody specific to one of the binding molecules are precipitated from solution by conjugating the antibody to a polymer bead that may be readily collected by centrifugation. The bound assay components are released from the beads (through a specific proteolysis event or other technique well known in the art which will not disturb the protein-protein interaction in the complex), and a second immunoprecipitation step is performed, this time utilizing antibodies specific for the correspondingly different interacting assay component. In this manner, only formed complexes should remain attached to the beads. Variations in complex formation in both the presence and the absence of a test compound can be compared, thus offering information about the ability of the compound to modulate interactions between the ligand described herein or fragment thereof and the receptor provided herein or fragment thereof.

Interfering Nucleic Acid Agents

In certain embodiments, interfering nucleic acid molecules that selectively target a receptor provided herein or a ligand described herein are provided herein and/or used in methods described herein. Interfering nucleic acids generally include a sequence of cyclic subunits, each bearing a base-pairing moiety, linked by intersubunit linkages that allow the base-pairing moieties to hybridize to a target sequence in a nucleic acid (typically an RNA) by Watson-Crick base pairing, to thrill a nucleic acid:oligomer heteroduplex within the target sequence. Interfering RNA molecules include, but are not limited to, antisense molecules, siRNA molecules, single-stranded siRNA molecules, miRNA molecules and shRNA molecules.

Typically at least 17, 18, 19, 20, 21, 22 or 23 nucleotides of the complement of the target mRNA sequence are sufficient to mediate inhibition of a target transcript. Perfect complementarity is not necessary. In some embodiments, the interfering nucleic acid molecule is double-stranded RNA. The double-stranded RNA molecule may have a 2 nucleotide 3' overhang. In some embodiments, the two RNA strands are connected via a hairpin structure, forming a shRNA molecule. shRNA molecules can contain hairpins derived from microRNA molecules. For example, an RNAi vector can be constructed by cloning the interfering RNA sequence into a pCAG-miR30 construct containing the hairpin from the miR30 miRNA. RNA interference molecules may include DNA residues, as well as RNA residues.

Interfering nucleic acid molecules provided herein can contain RNA bases, non-RNA bases or a mixture of RNA bases and non-RNA bases. For example, interfering nucleic acid molecules provided herein can be primarily composed of RNA bases but also contain DNA bases or non-naturally occurring nucleotides.

The interfering nucleic acids can employ a variety of oligonucleotide chemistries. Examples of oligonucleotide chemistries include, without limitation, peptide nucleic acid (PNA), linked nucleic acid (LNA), phosphorothioate, 2'O-Me-modified oligonucleotides, and morpholino chemistries, including combinations of any of the foregoing. In general, PNA and LNA chemistries can utilize shorter targeting sequences because of their relatively high target binding strength relative to 2'O-Me oligonucleotides. Phosphorothioate and 2'-O-Me-modified chemistries are often combined to generate 2'O-Me-modified oligonucleotides having a phosphorothioate backbone. See, e.g., PCT Publication Nos. WO/2013/11.2053 and WO/2009/008725, incorporated by reference in their entireties.

Peptide nucleic acids (PNAs) are analogs of DNA in which the backbone is structurally homomorphous with a deoxyribose backbone, consisting of N-(2-aminoethyl) glycine units to which pyrimidine or purine bases are attached. PNAs containing natural pyrimidine and purine bases hybridize to complementary oligonucleotides obeying Watson-Crick base-pairing rules, and mimic DNA in terms of base pair recognition (Egholm, Buchardt et al. 1993). The backbone of PNAs is formed by pep-tide bonds rather than phosphodiester bonds, making them well-suited for anti-sense applications (see structure below). The backbone is uncharged, resulting in PNA/DNA or PNA/RNA duplexes that exhibit greater than normal thermal stability. PNAs are not recognized by nucleases or proteases.

Despite a radical structural change to the natural structure, PNAs are capable of sequence-specific binding in a helix form to DNA or RNA. Characteristics of PNAs include a high binding affinity to complementary DNA or RNA, a destabilizing effect caused by single-base mismatch, resistance to nucleases and proteases, hybridization with DNA or RNA independent of salt concentration and triplex formation with homopurine DNA. PANAGENE™ has developed its proprietary Bts PNA monomers (Bts; benzothiazole-2-sulfonyl group) and proprietary oligomerization process. The PNA oligomerization using Bts PNA monomers is composed of repetitive cycles of deprotection, coupling and capping. PNAs can be produced synthetically using any technique known in the art. See, e.g., U.S. Pat. Nos. 6,969,766, 7,211,668, 7,022,851, 7,125,994, 7,145,006 and 7,179,896. See also U.S. Pat. Nos. 5,539,082; 5,714,331; and 5,719,262 for the preparation of PNAs. Further teaching of PNA compounds can be found in Nielsen et al., Science, 254:1497-1500, 1991. Each of the foregoing is incorporated by reference in its entirety.

Interfering nucleic acids may also contain "locked nucleic acid" subunits (LNAs). "LNAs" are a member of a class of modifications called bridged nucleic acid (BNA). BNA is characterized by a covalent linkage that locks the conformation of the ribose ring in a C30-endo (northern) sugar pucker. For LNA, the bridge is composed of a methylene between the 2'-O and the 4'-C positions. LNA enhances backbone preorganization and base stacking to increase hybridization and thermal stability.

The structures of LNAs can be found, for example, in Wengel, et al., Chemical Communications (1998) 455; Tetrahedron (1998) 54:3607, and Accounts of Chem. Research (1999) 32:301); Obika, et al., Tetrahedron Letters (1997) 38:8735; (1998) 39:5401, and Bioorganic Medicinal Chemistry (2008) 16:9230. Compounds provided herein may incorporate one or more LNAs; in some cases, the compounds may he entirely composed of LNAs. Methods for the synthesis of individual LNA nucleoside subunits and their incorporation into oligonucleotides are described, for example, in U.S. Pat. Nos. 7,572,582, 7,569,575, 7,084,125, 7,060,809, 7,053,207, 7,034,133, 6,794,499, and 6,670,461, each of which is incorporated by reference in its entirety. Typical intersubunit linkers include phosphodiester and phosphorothioate moieties; alternatively, non-phosphorous containing linkers may be employed. One embodiment is an LNA containing compound where each LNA subunit is separated by a DNA subunit. Certain compounds are composed of alternating LNA and DNA subunits where the intersubunit linker is phosphorothioate.

"Phosphorothioates" (or S-oligos) are a variant of normal DNA in which one of the nonbridging oxygens is replaced by a sulfur. The sulfurization of the internucleotide bond reduces the action of endo-and exonucleases including 5' to 3' and 3' to 5' DNA POL exonuclease, nucleases S1 and P1, RNases, serum nucleases and snake venom phosphodiesterase. Phosphorothioates are made by two principal routes: by the action of a solution of elemental sulfur in carbon disulfide on a hydrogen phosphonate, or by the method of sulfurizing phosphite triesters with either tetraethylthiuram disulfide (TETD) or 3H-1,2-bensodithiol-3-one 1, 1-dioxide (BDTD) (see, e.g., Iyer et al., J. Org. Chem. 55, 4693-4699, 1990). The latter methods avoid the problem of elemental sulfur's insolubility in most organic solvents and the toxicity of carbon disulfide. The TETD and BDTD methods also yield higher purity phosphorothioates.

"2'O-Me oligonucleotides" molecules carry a methyl group at the 2'-OH residue of the ribose molecule. 2'-O-Me-RNAs show the same (or similar) behavior as DNA, but are protected against nuclease degradation. 2'-O -Me-RNAs can also be combined with phosphothioate oligonucleotides (PTOs) for further stabilization. 2'O-Me oligonucleotides (phosphodiester or phosphothioate) can be synthesized according to routine techniques in the art (see, e.g., Yoo et al., Nucleic Acids Res. 32:2008-16, 2004).

The interfering nucleic acids described herein may be contacted with a cell or administered to an organism (e.g., a human). Alternatively, constructs and/or vectors encoding the interfering RNA molecules may be contacted with or introduced into a cell or organism. In certain embodiments, a viral, retroviral or lentiviral vector is used. In some embodiments, the vector has a tropism for cardiac tissue. In some embodiments the vector is an adeno-associated virus.

Typically at least 17, 18, 19, 20, 21, 22 or 23 nucleotides of the complement of the target mRNA sequence are sufficient to mediate inhibition of a target transcript. Perfect complementarity is not necessary. In some embodiments, the interfering nucleic acids contains a 1, 2 or 3 nucleotide mismatch with the target sequence. The interfering nucleic acid molecule may have a 2 nucleotide 3' overhang. If the interfering nucleic acid molecule is expressed in a cell from a construct, for example from a hairpin molecule or from an inverted repeat of the desired sequence, then the endogenous cellular machinery will create the overhangs. shRNA molecules can contain hairpins derived from microRNA molecules. For example, an RNAi vector can be constructed by cloning the interfering RNA sequence into a pCAG-miR30 construct containing the hairpin from the miR30 miRNA. RNA interference molecules may include DNA residues, as well as RNA residues.

In some embodiments, the interfering nucleic acid molecule is a siRNA molecule. Such siRNA molecules should include a region of sufficient homology to the target region, and be of sufficient length in terms of nucleotides, such that the siRNA molecule down-regulate target RNA. The term "ribonucleotide" or "nucleotide" can, in the case of a modified RNA or nucleotide surrogate, also refer to a modified nucleotide, or surrogate replacement moiety at one or more positions. It is not necessary that there be perfect complementarity between the siRNA molecule and the target, but the correspondence must he sufficient to enable the siRNA molecule to direct sequence-specific silencing, such as by RNAi cleavage of the target RNA. In some embodiments, the sense strand need only be sufficiently complementary with the antisense strand to maintain the overall double-strand character of the molecule.

In addition, an siRNA molecule may be modified or include nucleoside surrogates. Single stranded regions of an siRNA molecule may be modified or include nucleoside surrogates, the unpaired region or regions of a hairpin structure, e.g., a region which links two complementary regions, can have modifications or nucleoside surrogates. Modification to stabilize one or more 3'- or 5'-terminus of an siRNA molecule, against exonucleases, or to favor the antisense siRNA agent to enter into RISC are also useful. Modifications can include C3 (or C6, C7, C12) amino linkers, thiol linkers, carboxyl linkers, non-nucleotidic spacers (C3, C6, C9, C12, abasic, triethylene glycol, hexaethylene glycol), special biotin or fluorescein reagents that collie as phosphoramidites and that have another DMT-protected hydroxyl group, allowing multiple couplings during RNA synthesis.

Each strand of an siRNA molecule can be equal to or less than 35, 30, 25, 24, 23, 22, 21, or 20 nucleotides in length. In some embodiments, the strand is at least 19 nucleotides in length. For example, each strand can he between 21 and 25 nucleotides in length. In some embodiments, siRNA agents have a duplex region of 17, 18, 19, 29, 21, 22, 23, 24, or 25 nucleotide pairs, and one or more overhangs, such as one or two 3' overhangs, of 2-3 nucleotides.

A "small hairpin RNA" or "short hairpin RNA" or "shRNA" includes a short RNA sequence that makes a tight hairpin turn that can be used to silence gene expression via RNA interference. The shRNAs provided herein may be chemically synthesized or transcribed from a transcriptional cassette in a DNA plasmid. The shRNA hairpin structure is cleaved by the cellular machinery into siRNA, which is then bound to the RNA-induced silencing complex (RISC).

In some embodiments, shRNAs are about 15-60, 15-50, or 15-40 (duplex) nucleotides in length, about 15-30, 15-25, or 19-25 (duplex) nucleotides in length, or are about 20-24, 21-22, or 21-23 (duplex) nucleotides in length (e.g., each complementary sequence of the double-stranded shRNA is 15-60, 15-50, 15-40, 15-30, 15-25, or 19-25 nucleotides in length, or about 20-24, 21-22, or 21-23 nucleotides in length, and the double-stranded shRNA is about 15-60, 15-50, 15-40, 15-30, 15-25, or 19-25 base pairs in length, or about 18-22, 19-20, or 19-21 base pairs in length). shRNA duplexes may comprise 3' overhangs of about 1 to about 4 nucleotides or about 2 to about 3 nucleotides on the antisense strand and/or 5'-phosphate termini on the sense strand. In some embodiments, the shRNA comprises a sense strand and/or antisense strand sequence of from about 15 to about 60 nucleotides in length (e.g., about 15-60, 15-55, 15-50, 15-45, 15-40, 15-35, 15-30, or 15-25 nucleotides in length), or from about 19 to about 40 nucleotides in length (e.g., about 19-40, 19-35, 19-30, or 19-25 nucleotides in length), or from about 19 to about 23 nucleotides in length (e.g., 19, 20, 21, 22, or 23 nucleotides in length).

Non-limiting examples of shRNA include a double-stranded polynucleotide molecule assembled from a single-stranded molecule, where the sense and antisense regions are linked by a nucleic acid-based or non-nucleic acid-based linker; and a double-stranded polynucleotide molecule with a hairpin secondary structure having self-complementary sense and antisense regions. In some embodiments, the sense and antisense strands of the shRNA are linked by a loop structure comprising from about 1 to about 25 nucleotides, from about 2 to about 20 nucleotides, from about 4 to about 1.5 nucleotides, from about 5 to about 12 nucleotides, or 1, 2, 3, 4, 5, 6, 7, 8, 9, 10, 11, 12, 13, 14, 15, 16, 17, 18, 19, 20, 21, 22, 23, 24, 25, or more nucleotides.

Additional embodiments related to the shRNAs, as well as methods of designing and synthesizing such shRNAs, are described in U.S. patent application publication number 2011/0071208, the disclosure of which is herein incorporated by reference in its entirety for all purposes.

In some embodiments, provided herein are micro RNAs (miRNAs). miRNAs represent a large group of small RNAs produced naturally in organisms, some of which regulate the expression of target genes. miRNAs are formed from an approximately 70 nucleotide single-stranded hairpin precursor transcript by Dicer. miRNAs are not translated into proteins, but instead bind to specific messenger RNAs, thereby blocking translation. In some instances, miRNAs base-pair imprecisely with their targets to inhibit translation.

In some embodiments, antisense oligonucleotide compounds are provided herein. In certain embodiments, the degree of complementarity between the target sequence and antisense targeting sequence is sufficient to form a stable duplex. The region of complementarity of the antisense oligonucleotides with the target RNA sequence may be as short as 8-11 bases, but can be 12-15 bases or more, e.g., 10-40 bases, 12-30 bases, 12-25 bases, 15-25 bases, 12-20 bases, or 15-20 bases, including all integers in between these ranges. An antisense oligonucleotide of about 14-15 bases is generally long enough to have a unique complementary sequence.

In certain embodiments, antisense oligonucleotides may be 100% complementary to the target sequence, or may include mismatches, e.g., to improve selective targeting of allele containing the disease-associated mutation, as long as a heteroduplex formed between the oligonucleotide and target sequence is sufficiently stable to withstand the action of cellular nucleases and other modes of degradation which may occur in vivo. Hence, certain oligonucleotides may have about or at least about 70% sequence complementarity, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence complementarily, between the oligonucleotide and the target sequence. Oligonucleotide backbones that are less susceptible to cleavage by nucleases are discussed herein. Mismatches, if present, are typically less destabilizing toward the end regions of the hybrid duplex than in the middle. The number of mismatches allowed will depend on the length of the oligonucleotide, the percentage of G:C base pairs in the duplex, and the position of the mismatch(es) in the duplex, according to well understood principles of duplex stability.

Interfering nucleic acid molecules can be prepared, for example, by chemical synthesis, in vitro transcription, or digestion of long dsRNA by Rnase III or Dicer. These can be introduced into cells by transfection, electroporation, or other methods known in the art, See Hannon, al, 2002, RNA Interference, Nature 418: 244-251; Bernstein E et al 2002, The rest is silence. RNA 7: 1509-1521; Hutvagner G et al., RNAi: Nature abhors a double-strand. Curr. Opin. Genetics & Development 12: 225-232; Brummelkamp, 2002, A system for stable expression of short interfering RNAs in mammalian cells. Science 296; 550-553; Lee N S, Dohjima T, Bauer G, Li H, Li M-J, Ehsani A, Salvaterra P, and Rossi J. (2002). Expression of small interfering RNAs targeted against HIV-1 rev transcripts in human cells. Nature Biotechnol. 20:500-505; Miyagishi M, and Taira. K. (2002). U6-promoter-driven siRNAs with four uridine 3' overhangs efficiently suppress targeted gene expression in mammalian cells. Nature Biotechnol. 20:497-500; Paddison P J, Caudy A A, Bernstein E, Hannon G J, and Conklin D S. (2002). Short hairpin RNAs (shRNAs) induce sequence-specific silencing in mammalian cells. Genes & Dev. 16:948-958; Paul C P, Good P D, Winer I, and Engelke D R. (2002). Effective expression of small interfering RNA in human cells. Nature Biotechnol. 20:505-508; Sui G, Soohoo C, Affar Gav F, Shi Y, Forrester W C, and Shi Y. (2002). A. DNA vector-based RNAi technology to suppress gene expression in mammalian cells. Proc. Natl. Acad. Sci. USA 99(6):5515-5520; Yu J-Y. DeRuiter S L, and Turner D L. (2002). RNA interference by expression of short-interfering RNAs and hairpin RNAs in mammalian cells. Proc. Natl. Acad. Sci. USA 99(9):6047-6052.

In the present methods, an interfering nucleic acid molecule or an interfering nucleic acid encoding polynucleotide can be administered to the subject, for example, as naked nucleic acid, in combination with a delivery reagent, and/or as a nucleic acid comprising sequences that express an interfering nucleic acid molecule. In some embodiments the nucleic acid comprising sequences that express the interfering nucleic acid molecules are delivered within vectors, e.g. plasmid, viral and bacterial vectors. Any nucleic acid delivery method known in the art can be used in the methods described herein. Suitable delivery reagents include, but are not limited to, e.g., the Minis Transit TKO lipophilic reagent; lipofectin; lipofectamine; cellfectin; polycations (e.g., polylysine), atelocollagen, nanoplexes and liposomes. The use of atelocollagen as a delivery vehicle for nucleic acid molecules is described in Minakuchi et al. Nucleic Acids Res., 32(13):e109 (2004); Hanai et al. Ann NY Acad Sci., 1082:9-17 (2006); and Kawata et al. Mol Cancer Ther., 7(9):2904-12 (2008); each of which is incorporated herein in their entirety. Exemplary interfering nucleic acid delivery systems are provided in U.S. Pat. Nos. 8,283,461, 8,313,772, 8,501,930, 8,426,554, 8,268,798 and 8,324,366, each of which is hereby incorporated by reference in its entirety.

In some embodiments of-the methods described herein, liposomes are used to deliver an inhibitory oligonucleotide to a subject. Liposomes suitable for use in the methods described herein can be formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example, as described in Szoka et al. (1980), Ann. Rev. Biophys, Bioeng. 9:467; and U.S. Pat. Nos. 4,235,871, 4,501,728, 4,837,028, and 5,019,369, the entire disclosures of which are herein incorporated by reference.

The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure.

Opsonization-inhibiting moieties for use in preparing the liposomes described herein are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES; e.g., as described in U.S. Pat. No. 4,920,016, the entire disclosure of which is herein incorporated by reference.

In some embodiments, opsonization inhibiting moieties suitable for modifying liposomes are water-soluble polymers with a number-average molecular weight from about 500 to about 40,000 daltons, or from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. In some embodiments, the opsonization-inhibiting moiety is a PEG, PPG, or derivatives thereof. Liposomes modified with PEG or PEG-derivatives are sometimes called "PEGylated liposomes."

Pharmaceutical Compositions

In certain embodiments, provided herein is a composition, e.g., a pharmaceutical composition, containing at least one agent described herein together with a pharmaceutical acceptable carrier. In one embodiment, the composition includes a combination of multiple (e.g., two or more) agents described herein.

As described in detail below, the pharmaceutical compositions disclosed herein may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; or (2) parenteral administration, for example, by subcutaneous, intramuscular, intravenous, intrathecal, intracerebral or epidural injection as, for example, a sterile solution or suspension, or sustained-release formulation.

Methods of preparing these formulations or compositions include the step of bringing into association an agent described herein with the carrier and, optionally, one or more accessory ingredients. In general, the formulations are prepared by uniformly and intimately bringing into association an agent described herein with liquid carriers, or finely divided solid carriers, or both, and then, if necessary, shaping the product.

Pharmaceutical compositions suitable for parenteral administration comprise one or more agents described herein in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions include water, ethanol, dimethyl sulfoxide (DMSO), polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Regardless of the route of administration selected, the agents provided herein, which may be used in a suitable hydrated form, and/or the pharmaceutical compositions disclosed herein, are formulated into pharmaceutically-acceptable dosage forms by conventional methods known to those of skill in the art.

Therapeutic Methods

In certain embodiments, provided herein are methods of stimulating erythropoiesis in a subject (e.g., a subject in need thereof, such as a subject with anemia) or inhibiting erythropoiesis in a subject (e.g., a subject in need thereof, such as a subject with erythrocytosis) by administering to the subject an agent or pharmaceutical composition provided herein.

In some embodiments, the methods provided herein relate to the stimulation of erythropoiesis in a subject (e.g., a human subject). In some embodiments, the subject is an infant. In some embodiments, the subject is a subject in need thereof. In some embodiments, the subject in anemic. In some embodiments, the subject has congenital anemia. The subject may have iron deficiency anemia. In some embodiments, the subject has Diamond Blackfan Anemia. In some embodiments, the subject has refractory anemia. The subject may be refractory to erythropoietin. The subject may have myelodysplastic syndrome. The subject may have anemia as a result of myelosuppressive chemotherapy. The subject may have cancer.

In some embodiments, the subject is being treated with erythropoietin or an erythropoietin derivative. In some embodiments, the erythropoietin or erythropoietin derivative is asialoerythropoietin, N-deglycosylated erythropoietin, O-deglycosylated erythropoietin, erythropoietin with reduced carbohydrate content, erythropoietin with altered glycosylation patterns, erythropoietin with carbohydrates oxidized then reduced, arylglyoxal-modified erythropoietin, alkylglyoxal-modified erythropoietin, 2,3-butanedione-modified erythropoietin, cyclohexanedione-modified erythropoietin, biotinylated erythropoietin, N-alkylated-lysyl-ethropoietin, glucitolyl lysine erythropoietin, alpha-deoxy-alpha-fructosyllysine-erythropoietin, carbamylated erythropoietin, acetylated erythropoietin, succinylated erythropoietin, alpha-carboxyalkyl erythropoietin, nitrated erythropoietin, iodinated erythropoietin.

In some embodiments, the subject has a cancer-associated anemia. In some embodiments the cancer-associated anemia is a cancer is such as, but not limited to, breast, prostate, lung, skin, colorectal, cervical, pancreatic, ovarian, lymphoma, leukemia, liver, testicular, and brain cancer.

In some embodiments, provided herein is a method of stimulating erythropoiesis in a subject with anemia comprising administering to the subject an agent that binds to MST1r. In some embodiments the agent induces MST1r activity. In some embodiments, time agent is a polypeptide agent (e.g., a MSP ligand protein or a fragment thereof). In some embodiments, the agent is an antibody agent. In some embodiments, the agent is a small molecule agent. In some embodiments, the method further comprises administering to time subject erythropoietin or an erythropoietin derivative. In some embodiments, the erythropoietin or erythropoietin derivative is asialoerythropoietin, N-deglycosylated erythropoietin, O-deglycosylated erythropoietin, erythropoietin with reduced carbohydrate content, erythropoietin with altered glycosylation patterns, erythropoietin with carbohydrates oxidized then reduced, arylglyoxal-modified erythropoietin, alkylglyoxal-modified erythropoietin, 2,3-butanedione-modified erythropoietin, cyclohexanedione-modified erythropoietin, biotinylated erythropoietin, N-glucitolyl lysine erythropoietin, alpha-deoxy-alpha-fructosyllysine-erythropoietin, carbamylated erythropoietin, acetylated erythropoietin, succinylated erythropoietin, alpha-carboxyalkyl erythropoietin, nitrated erythropoietin, iodinated erythropoietin.

In some embodiments, provided herein is a method of stimulating erythropoiesis in a subject with anemia comprising administering to the subject an agent that binds to IL-17ra. In some embodiments the agent induces IL-17ra activity. In some embodiments, the agent is a polypeptide agent (e.g., an IL-17a protein or a fragment thereof, an IL-17f protein or a fragment thereof, or a IL-17a/f heterodimeric polypeptide). In some embodiments, the agent is an antibody agent. In some embodiments, the agent is a small molecule agent. In some embodiments, the method further comprises administering to the subject erythropoietin or an erythropoietin derivative. In some embodiments, the erythropoietin or erythropoietin derivative is asialoerythropoietin, N-deglycosylated erythropoietin, O-deglycosylated erythropoietin, erythropoietin with reduced carbohydrate content, erythropoietin with altered glycosylation patterns, erythropoietin with carbohydrates oxidized then reduced, arylglyoxal-modified erythropoietin, alkylglyoxal-modified erythropoietin, 2,3-butanedione-modified erythropoietin, cyclohexanedione-modified erythropoietin, biotinylated erythropoietin, N-alkylated-lysyl-erythropoietin, glucitolyl lysine erythropoietin, alpha-deox,7-alpha-fructosyllysineerythropoietin, carbamylated erythropoietin, acetylated erythropoietin, succinylated erythropoietin, alpha-carboxyalkyl erythropoietin, nitrated erythropoietin, iodinated erythropoietin.

In some embodiments, provided herein is a method of stimulating erythropoiesis in a subject with anemia comprising administering to the subject an agent that inhibits the binding of WNT5a to RYK and/or inhibits WNT5a and/or RYK expression or activity. In some embodiments the agent inhibits RYK activity. In some embodiments, the agent is a polypeptide agent (e.g., non-activating WNT5a or RYK polypeptide or fragment thereof). In some embodiments, the agent is an antibody agent. In some embodiments, the agent is a small molecule agent. In some embodiments, the agent is an inhibitory nucleic acid agent. In some embodiments, the method further comprises administering to the subject erythropoietin or an erythropoietin derivative. In some embodiments, the erythropoietin or erythropoietin derivative is asialoerythropoietin, N-deglycosylated erythropoietin, O-deglycosylated erythropoietin, erythropoietin with reduced carbohydrate content, erythropoietin with altered glycosylation patterns, erythropoietin with carbohydrates oxidized then reduced, arylglyoxal-modified erythropoietin, alkylglyoxal-modified erythropoietin, 2,3-butanedione-modified erythropoietin, cyclohexanedione-modified erythropoietin, biotinylated erythropoietin, N-alkylated-lysyl-erythropoietin, glucitolyl lysine erythropoietin, alpha-deoxy-alpha-fructosyllysine-erythropoietin, carbamylated erythropoietin, acetylated erythropoietin, succinylated erythropoietin, alpha-carboxyalkyl erythropoietin, nitrated erythropoietin, iodinated erythropoietin.

In some embodiments, the methods provided herein relate to the inhibition of erythropoiesis in a subject (e.g., a human subject). In some embodiments; the subject is a subject in need thereof In some embodiments, the subject has erythrocytosis (e.g., primary or secondary erythrocytosis). In some embodiments, the subject has polycythemia vera. In some embodiments; the subject is being treated with a Jak2 inhibitor. In some embodiments, the Jak2 inhibitor is ruxolitinib, fedratinib, tofacitinib, baricitinib (INCB039110), lestaurtinib (CEP701), pacritinib (SB1518), XL019, AZD1480, gandotinib (LY2784544), BMS911543, fedratinib (SAR302503), decemotinib (V-509), INCB39110, GEN1, GEN2, GLPG0634, NS018, and N-(cyanomethyl)-4-[2-(4-morpholinoanilino)pyrimidin-4-yl]benzamide; or pharmaceutically acceptable salts thereof.

In some embodiments, provided herein is a method of inhibiting erythropoiesis in a subject with anemia comprising administering to the subject an agent that that inhibits the binding of MST1r to MSP and/or inhibits MST1r and/or MSP expression or activity. In some embodiments the agent inhibits MST1r activity. In some embodiments, the agent is a polypeptide agent (e.g., non-activating MSP or MST1r polypeptide or fragment thereof). In some embodiments, the agent is an antibody agent. In some embodiments; the agent is a small molecule agent. In some embodiments, the agent is an inhibitory nucleic acid agent. In some embodiments, the method further comprises administering to the subject a Jak2 inhibitor. In some embodiments, the Jak2 inhibitor is ruxolitinib, fedratinib, tofacitinib, baricitinib (INCB039110), lestaurtinib (CEP701), pacritinib (SB1518), XL019, AZD1480, gandotinib (LY2784544), BMS911543, fedratinib (SAR302503), decemotinib (V-509), INCB39110, GEN1, GEN2, GLPG0634, NS018, and N-(cyanomethyl)-4-[2-(4-morpholinoanilino)pyrimidin-4-yl]benzamide; or pharmaceutically acceptable salts thereof.

In some embodiments, provided herein is a method of inhibiting erythropoiesis in a subject with anemia comprising administering to the subject an agent that binds RYK. In some embodiments the agent induces RYK activity. In some embodiments, the agent is a polypeptide agent (e.g., a WNT5a protein or a fragment thereof). In some embodiments, the agent is an antibody agent. In some embodiments, the agent is a small molecule agent. In some embodiments, the agent is an inhibitory nucleic acid agent. In some embodiments, the method further comprises administering to the subject a Jak2 inhibitor. In some embodiments, the Jak2 inhibitor is ruxolitinib, fedratinib, tofacitinib, baricitinib (INCB039110), lestaurtinib (CEP701), pacritinib (SB1518), XL019AZD1480, gandotinib (LY2784544), BM5911543, fedratinib (SAR302503), decemotinib (V-509), INCB39110, GEN1, GEN2, GLPG0634, NS018, and N-(cyanomethyl)-4-[2-(4-morpholinoamino)pyrimidin-4-yl]benzamide; or pharmaceutically acceptable salts thereof.

In some embodiments, provided herein is a method of inhibiting erythropoiesis in a subject with anemia comprising administering to the subject an agent that that inhibits the binding of IL-17ra to IL-17a and/or inhibits IL-17ra and/or IL-17a expression or activity. In some embodiments the agent inhibits IL-17ra activity. In some embodiments, the agent is a polypeptide agent (e.g., non-activating IL-17a or IL-17ra polypeptide or fragment thereof). In some embodiments, the agent is an antibody agent. In some embodiments, the agent is a small molecule agent. In some embodiments, the agent is an inhibitory nucleic acid agent. In some embodiments, the method further comprises administering to the subject a Jak2 inhibitor. In some embodiments, the Jak2 inhibitor is ruxolitinib, fedratinib, tofacitinib, baricitinib (INCB039110), lestaurtinib (CEP701), pacritinib (SB1518), XL019, AZD1480, gandotinib (LY2784544), BMS911543, fedratinib (SAR302503), decemotinib (V-509), INCB39110, GEN1, GEN2, GLPG0634, NS018, and N-(cyanomethyl)-4-[2-(4-morpholinoamino)pyrimidin-4-yl]benzamide; or pharmaceutically acceptable salts thereof.

The pharmaceutical compositions disclosed herein may be delivered by any suitable route of administration, including orally and parenterally. In certain embodiments the pharmaceutical compositions are delivered generally (e.g., via oral or parenteral administration).

In certain aspects, agents and/or compositions disclosed herein may be administered at a dose sufficient to achieve the desired result (e.g., increased or decreased erythropoiesis). In some embodiments, the agent is a ligand of MST1r, RYK, and/or IL-17ra . In some embodiments, the agent is IL-17a or a fragment thereof. In some embodiments, the agent s IL-17f or a fragment thereof. In some embodiments, the agent is heterodimeric IL-17a/f protein or a fragment thereof. In some embodiments, the agent is WNT5 or a fragment thereof. In some embodiments, the agent is MSP or a fragment thereof. The agent may be an agonist of IL-17ra. In some embodiments, the agent is an agent disclosed herein.

In certain embodiments, the method may comprise administering about 1 µg to about 1 gram of agent or composition to the subject, such as about 1 µg to about 1 mg, about 2 µg to about 2 mg, about 3 µg to about 3 mg, about 4 µg to about 4 mg, about 100 µg to about 2 mg, about 200 µg to about 2 mg, about 300 µg to about 3 mg, about 400 µg to about 4 mg, about 250 µg to about 1 mg, or about 250 µg to about 750 µg of the agent or composition. In some embodiments, the method may comprise administering about 25 µg, about 50 µg, about 75 µg, about 100 µg, about 125 µg about 150 µg, about 175 µg about 200 µg, about 225 µg about 250 µg, about 275 µg, about 300 µg, about 325 µg, about 350 µg, about 375 µg, about 400 µg, about 425 µg, about 450 µg, about 475 µg, about 500 µg, about 600 µ, about 650 µg, about 700 µg about 750 µg, about 800 µg, about 850 µg, about 900 µg, about 950 µg, about 1000 µg, about 1200 µg, about 1250 µg, about 1300 µg, about 1333 µg, about 1350 µg, about 1400 µg, about 1500 µg, about 1667 µg, about 1750 µg, about 1800 µg, about 2000 µg, about 2200 µg, about 2250 µg, about 2300 µg, about 2333 µg, about 2350 pa, about 2400 µg, about 2500 µg, about 2667 µg, about 2750 µg, about 2800 µg, about 3 mg, about 3.3 mg, about 3.5 mg, about 3.7 mg, about 4 mg, about 4.5 mg, about 5 mg, about 6 mg, about 7 mg, about 8 mg, about 9 mg, or about 10 mg of the agent or composition.

In some embodiments, administering an agent or composition the subject comprises administering a bolus of the composition. The method may comprise administering the composition to the subject at least once per month, twice per month, three times per month. In certain embodiments, the method may comprise administering the composition at least once per week, at least once every two weeks, or once every three weeks. In some embodiments, the method may comprise administering the composition to the subject 1, 2. 3, 4, 5, 6, or 7 times per week.

In some embodiments, the agents and/or compositions described herein may be administered conjointly with erythropoietin or erythropoietin derivative (e.g., an erythropoietin derivative disclosed herein).

In certain embodiments, the compositions of the invention can be administered in a variety of conventional ways. In some aspects, the compositions of the invention are suitable for parenteral administration. In some embodiments, these compositions may be administered, for example, intraperitoneally, intravenously, intrarenally, or intrathecally. In some aspects, the compositions of the invention are injected intravenously.

In some embodiments, actual dosage levels of the active ingredients in the pharmaceutical compositions may be varied so as to obtain an amount of the active ingredient which is effective to achieve the desired therapeutic response for a particular patient, composition, and mode of administration, without being toxic to the patient.

In general, a suitable daily dose of an agent described herein will be that amount of the agent which is the lowest dose effective to produce a therapeutic effect. Such an effective dose will generally depend upon the factors described above.

In some embodiments, the methods disclosed herein relate to the use of the growth factors disclosed herein (e.g., IL-17a, WNT5, MSP or IL-170, in the amplification of human early erythroid progenitors in vitro. In recent years, several culture systems have been developed that produce and amplify early erythroid progenitors from CD34+ progenitors, for the purpose of generating transfusable red blood cells in vitro (See Migliaccio A R, Whitsett C, Papayannopoulou T, Sadelain M. The potential of stem cells as an in vitro source of red blood cells for transfusion can be found in Cell Stem Cell. 2012;10(2):115-119, hereby incorporated by reference in its entirety). Details regarding transfusion of in vitro-generated red blood cells can be found in *Blood*, 2011; 118(19):5071-5079 (hereby incorporated by reference in its entirety). An in vitro source of red blood cells may be particularly useful for rare blood types, and for the in vitro application of gene therapy for blood genetic diseases (e.g. hemoglobinopathies). Sustaining and amplifying early erythroid progenitors in culture is still a challenge. Most culture systems use some combination of gluococorticoids, erythropoietin, stem cell factor and insulin-like growth factor I (IGF I) for this purpose. Activating IL-17ra with IL-17a or IL-17f, or inhibiting Ryk and Mst1r with Wnt5a and MSP, respectively, may enhance the amplification and propagation of erythroid progenitors in these systems.

In certain aspects, provided herein are methods of generating red blood cells in vitro. In some embodiments, disclosed herein are methods of expanding or propagating progenitor cells in vitro comprising supplementing or adding an agent that activates IL-17ra to a cell medium comprising the progenitor cells. In some aspects, disclosed herein are methods of expanding or propagating progenitor cells in vitro comprising supplementing or adding an agent that inhibits Ryk and/or Mst1r. The agent many be an agent disclosed herein. In some embodiments, the methods disclosed herein include adding or supplementing in vitro medium used for growing or expanding progenitor cells (e.g., CD34+ progenitors or erythroid progenitors) with a composition or agent disclosed herein. In some embodiments, the methods disclosed herein include adding or supplementing cell culture methods used for growing or expanding progenitor cells (e.g., CD34+ progenitors or erythroid progenitors) with a composition or agent disclosed herein. In some embodiments, the methods disclosed herein include adding or supplementing in vitro medium used for growing or expanding progenitor cells (e.g., CD34+ progenitors or erythroid progenitors) with a composition or agent disclosed herein.

EXEMPLIFICATION

Example 1

Single-Cell RNA-seq of Kit+ Hematopoietic Progenitors

Figure 1:
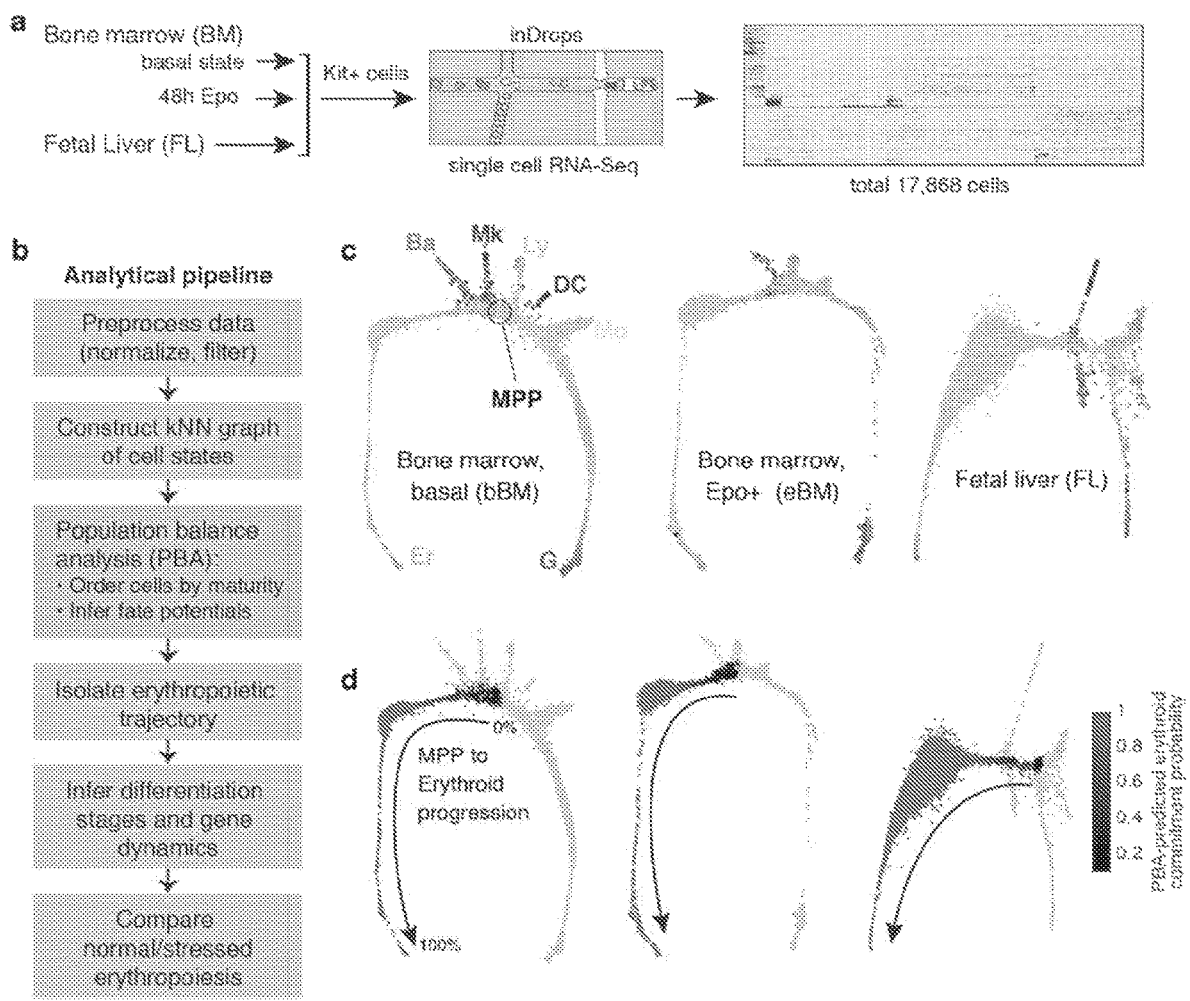
FIG. 1 includes 5 panels (Panels a-e). Panel a is schematic depicting single cell RNA expression analysis of hematopoietic progenitor cells (HPC). Panel b is a schematic of the analytical pipeline as described in Example 1. Panel c shows SPRING plots of single cell trancriptomes. Panel d shows the SPRING plots analyzed for erythroid trajectory. Panel e shows data representing the expression of established erythroid regulators.

To define the principal cellular stages of early erythropoiesis, single cell RNA sequencing (scRNA-Seq) were performed on hematopoietic progenitor cells (HPC) isolated from adult mouse bone marrow (BM) at 8 weeks of age, and from the mouse fetal liver (FL) at mid gestation (embryonic day 13.5). BM was isolated in a basal steady state (bBM) from untreated adult mice, or following stimulation with Epo (eBM) for 48 hours to induce an erythropoietic stress response. FIPCs were isolated conditional on expression of the cell-surface receptor Kit, expressed on all hematopoietic stem and early progenitor cells (FIG. 1, Panel a). This inclusive approach to cell fractionation preserves the relative abundance of the various early progenitor cell states, allowing unbiased reconstruction of early hematopoietic differentiation.

Across three droplet microfluidic runs, a total of 17,868 cells were isolated, barcoded and sequenced. Following filtering, over 14,000 cells were carried forward for analysis (FIG. 1, Panel b).

To visualize the single cell transcriptomes, a graph-based representation of the data, SPRING, was used where each cell is represented by a single node that is connected by unweighted edges to its nearest neighboring cells in gene expression space. Cell positions are then projected into two dimensions using a force-directed graph layout (FIG. 1, Panel c). Because the hierarchy of gene expression states is multi-dimensional, 2D representations necessarily distort their true organization. Therefore, while 2D representations of the SPRING plots were used for visualization throughout the study, all quantitative analyses were carried out on the underlying cell nearest-neighbor graph, which accurately captures the high-dimensional nature of the data.

With cells colored according to the expression of lineage-specific marker genes (FIG. 1, Panel c) (ref to source/list of the marker genes), the broad structure of the SRING plot becomes apparent. The cells organize into an undifferentiated core, from which seven distinct branches emerge corresponding to differentiating progenitors of the granulocytic, monocytic, dendritic, lymphoid, megakaryocytic, basophilic, and erythroid lineages. As expected, in fetal (FL) and Epo-stimulated hematopoiesis (eBM), the erythroid branch was significantly expanded compared with basal hematopoiesis (bBM). All the data reported here is made available through an interactive web-based tool, which allows users to explore gene expression on these graphs.

Example 2

Defining the Erythroid Differentiation Trajectory by Population Balance Analysis (PBA)

Each of the three experiments captures cell transcriptomes representing a continuum of all stages of differentiation, from MPPs to lineage-restricted progenitors. To provide a formal basis for ordering cells along their differentiation trajectories. Population Balance Analysis (PBA) was used. PBA is a novel computational approach. PBA orders cells along their differentiation progression by assigning each cell a predicted probability of committing to each of the seven terminal fates. Although they constitute formal predictions of cell fate, the predicted fate probabilities can also be intuitively understood to quantify the distance of any cell from each of the branch points leading to the seven terminal fates. When applied to the bBM data, the PBA predictions are consistent with previous functional assays on fractionated HPC sub-populations. Although PBA can be used to predict regulators of all seven lineage in this data set, here the focus is predominantly on erythropoiesis.

To isolate the erythroid trajectory for detailed study, an MPP-to-erythroid axis in each of the three experiments was defined by ordering cells based on their graph distance from the MPPs, and keeping only cells for which the probability of erythroid fate increases with distance (FIG. 1, Panel d). These cells were used to create a smoothed time series for every gene along early erythroid differentiation, in a manner akin to previously known pseudotemporal ordering algorithms. To establish confidence in the ordering of cells along the erythroid trajectory, the expression of known erythroid regulators (FIG. 1, Panel e) was examined. It was found that the unbiased ordering of scRNA-Seq data spontaneously recapitulates all of the events examined: transcriptional regulators that function in hematopoietic stem cells/MPP, like GATA2, Tal1, Ldb1, and PU.1, are found expressed at the MPP starting point; GATA 1 is then induced and increases rapidly, concurrent with suppression of PU.1, a reciprocal event in the specification of the megakaryocytic and erythroid lineages. The Epo receptor, EpoR, is rapidly induced early in the progression and maintains a high plateau, rising to a further peak with its target, the transferrin receptor (Tfrc), just prior to ETD (represented at the very end of the plot in FIG. 1. Panel e as a Kit-low phase). Additional established events in early erythropoiesis were also observed, including an early peak in GATA2 that is rapidly suppressed with increasing GATA reflecting the GATA switch, while other key erythropoietic transcription factors (TFs), Klf1, Tal1, FOG1 (Zfpm1) and Lbd1, are induced and/or continue to be expressed at high levels throughout the progression. CD34 and Kit, markers of MPP and early progenitors, are expressed initially, and are repressed with their distinct dynamics. Taken together, the temporal ordering of the single cell transcriptomes accurately reflects known events of early erythropoiesis.

Example 3

Figure 2:
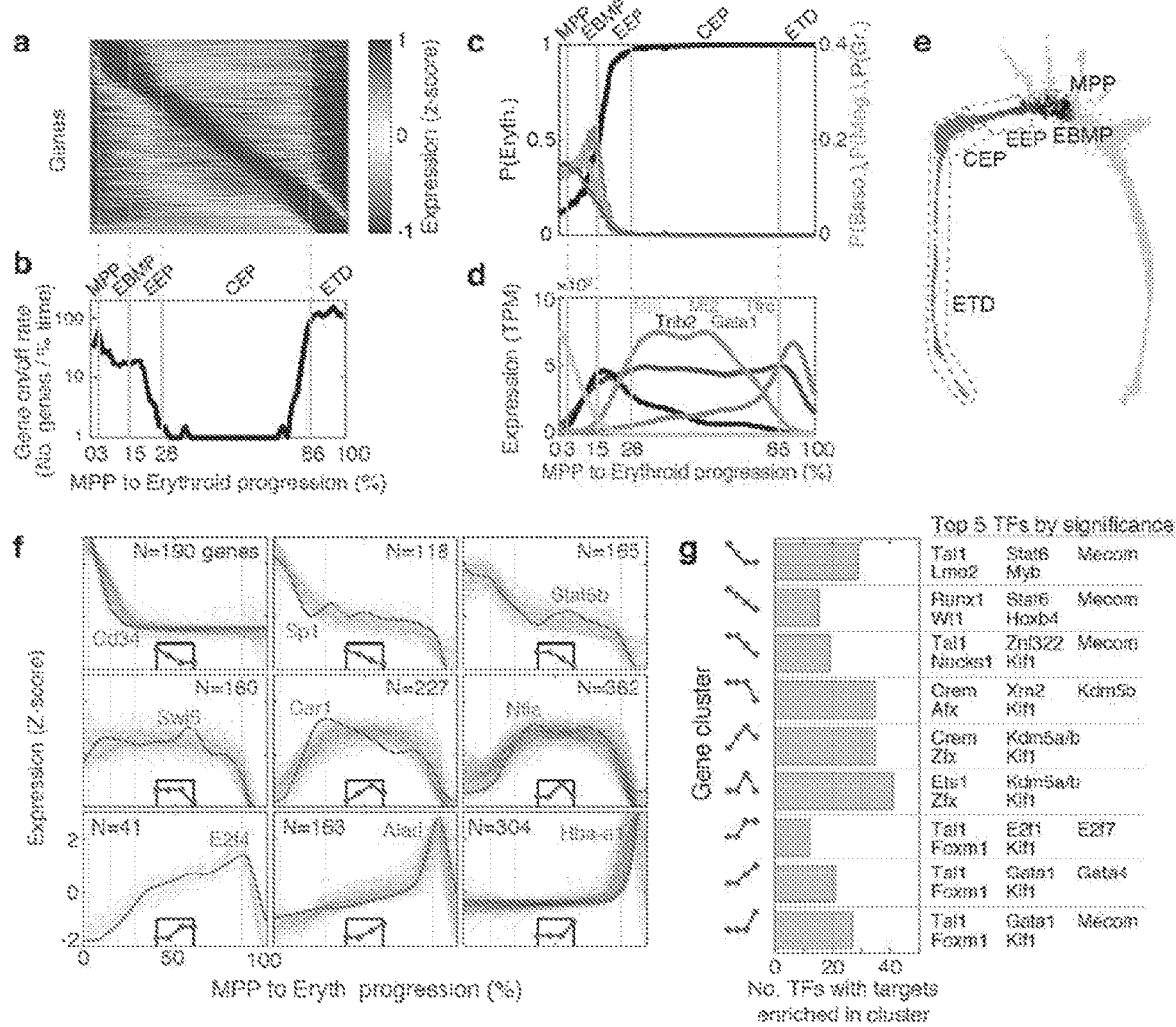
FIG. 2 includes 7 panels (Panels a-h), which show data representing dynamic patterns in gene expression in early erythropoiesis FIG. 3 includes 5 panels (Panels a-e), which show validation of the SPRING plot and PBA predictions provided herein.
Figure 2:
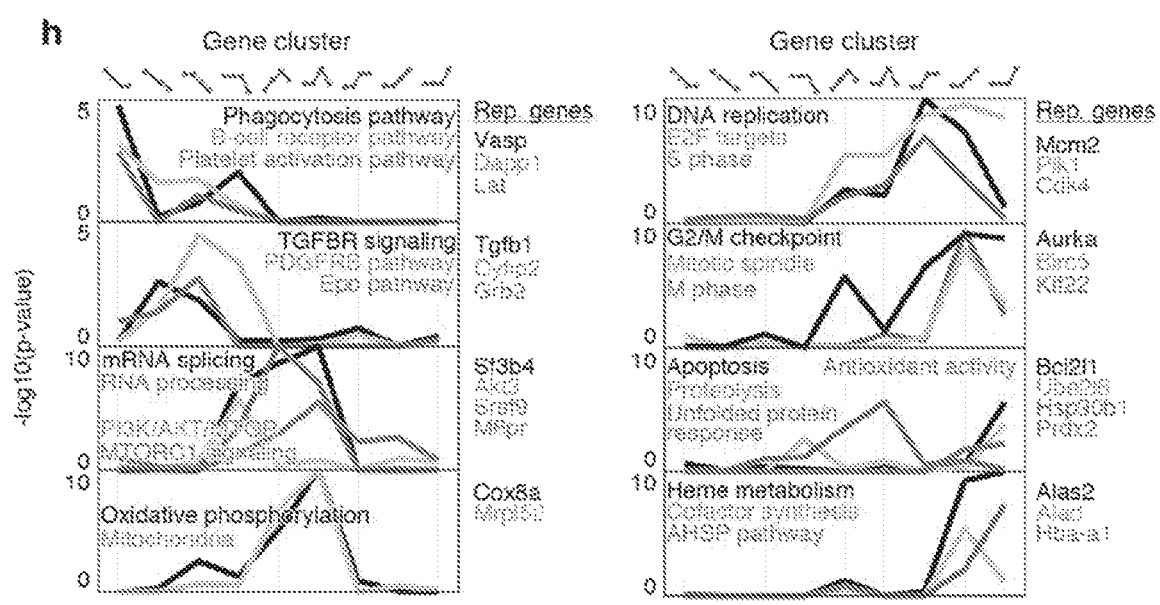

Gene Expression Dynamic Patterns Reveal a Prominent Amplification Module in Early Erythropoiesis Having inferred a putative transcription ordering of early erythropoiesis, over 4,000 genes that vary significantly along the MPP-to-erythroid axis were identified. Focusing initially on the bBM data, the gene expression profiles revealed large groups of genes showing similar, stable expression, punctuated by rapid concurrent changes in gene expression (FIG. 2, Panel a). This suggested that early erythropoiesis might naturally partition into distinct stages.

To define stages of erythropoiesis, regions with low frequency of gene inflexion (on/off) on the MPP-to-erythroid axis (FIG. 2, Panel b) and fate branch points along the differentiation trajectory, (FIG. 1, Panels c and d) were examined. Fate branch points were formally found as regions where PBA-predicted fate probabilities increase for non-erythroid fates (FIG. 2, Panel c). From these metrics, the erythroid trajectory was partitioned into five stages (FIG. 2, Panels a-e), starting with multipotent MPPs and ending with ETD. The existence of three intermediate stages represents the first key prediction of the analysis, for which experimental support is provided in the following sections.

The three intermediate stages were termed: (1) erythroid-basophil-megakaryocytic progenitors (EBMP), (2) early erythroid progenitors (EEP), and (3) committed erythroid progenitors (CEP). EBMPs include cells passing branch points to megakaryocytic and basophil lineages, and were thus predicted to be uncommitted. The EEP stage is a narrow bottleneck just past the final non-erythroid fate branch point, in which gene expression changes rapidly (FIG. 2, Panels b, c, and e). The CEP contains the majority of pre-ETD erythroid progenitors, and it terminates with a sharp transcriptional change leading to ETD with the onset of Tfrc expression (FIG. 2, Panels a-c), Representative erythroid genes that mark each of the specific stages are shown in FIG. 2d.

To assess biological function and transcription factor target enrichment in the EBMP, EEP and CEP stages, the gene expression profiles were temporally clustered. A gene set enrichment analysis (GSEA) of the dynamic gene clusters was carried out (FIG. 2f-h and Extended Data FIG. 2). Strikingly, the most dominant dynamic clusters were of genes specifically upregulated at the CEP stage (represented by Car1, Nfia in FIG. 2, Panel f). Consistent with the population expansion at this stage, these clusters are enriched for cell cycle and growth-related genes, including mTOR signaling, nucleotide metabolism, RNA processing, oxidative phosphorylation, DNA replication, and mitochondrial components. These annotation results suggested that CEPs may act as an early "amplification" module for significant population expansion. Consistent with this hypothesis, CEPs are the most abundant cells in early erythropoiesis.

Genes expressed only in the MPP stage were enriched for non-erythroid lineage terms, while ETD-specific genes were enriched for erythroid pathway components such as heme metabolism, and for targets of the canonical erythroid TFs Gata1, Tal1, and Klf1, although the TFs themselves showed initial upregulation much earlier. This analysis predicts several new epigenetic and transcriptional regulators of erythroid progression: KDM5a/b, ZFX, XRN2, FOXM1, CREM, AFX (FOXO4) (FIG. 2, Panel g). Curiously, although GATA1 itself is expressed essentially throughout the erythroid trajectory (a prediction of the transcriptional ordering that is experimentally validated below), its targets do not rise strongly prior to the ETD. However, some weak GATA1 activity may be present even very early on: within the MPP compartment the genes correlating most strongly with PBA-predicted erythroid fate were enriched as targets of Tal1, GATA1, GATA2, EVI1 (Mecum) and Myb, as well as targets of regulators with fewer known direct links to erythropoiesis, Mtf2, Rela, Ep300 and Hif1a.

Example 4

Validation of the SPRING Plot and PBA Predictions

To test the above predictions, a PU.1-GFP reporter mouse and a cell-surface marker expressed by progenitors with an erythroid differentiation bias, CD55 were examined. The SPRING plot shows that CD55+ cells and PU.1-expressing cells occupy extensive non-overlapping regions that emanate in opposite directions from the MPP. No overlap was found between PU.1-GFP expressing cells and cells positive for CD55+ by flow cytometry, thus confirming the gross morphology of the SPRING plot, and suggesting that the early erythroid trajectory lies within the CD55+ fraction of Kit+ cells (FIG. 3, Panel a).

Figure 3:
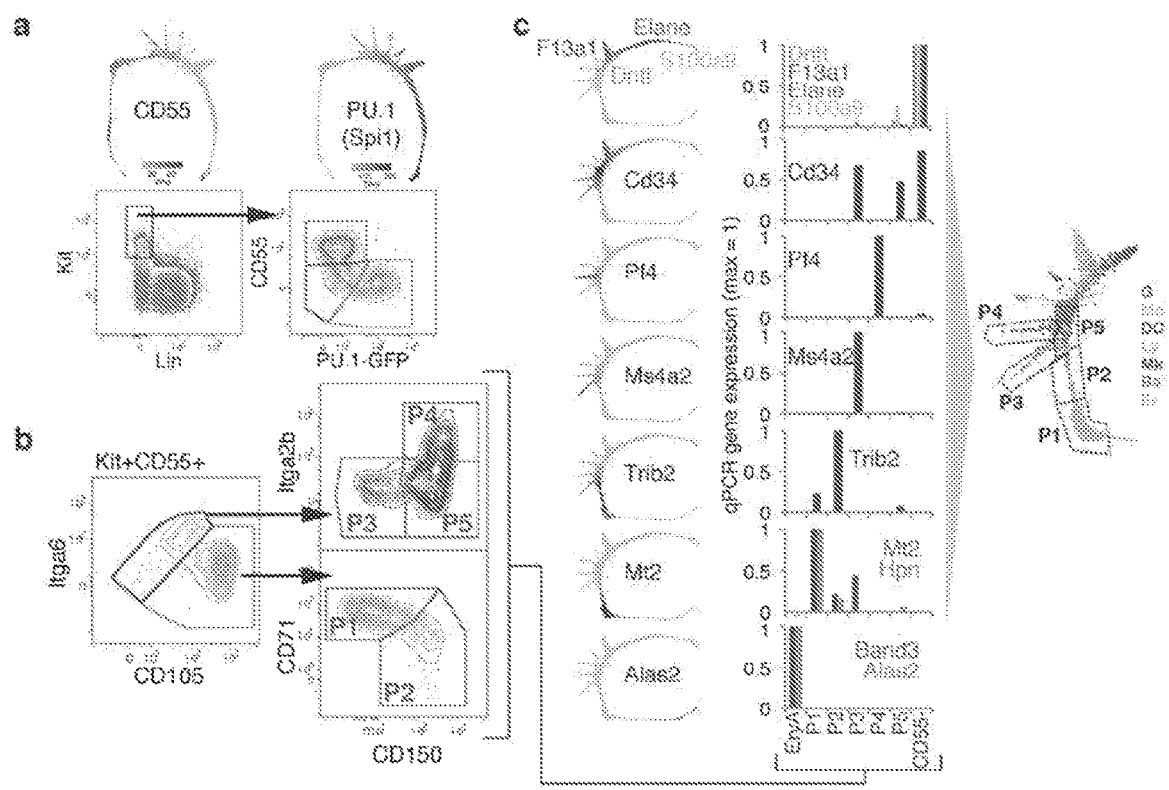
Figure 3:
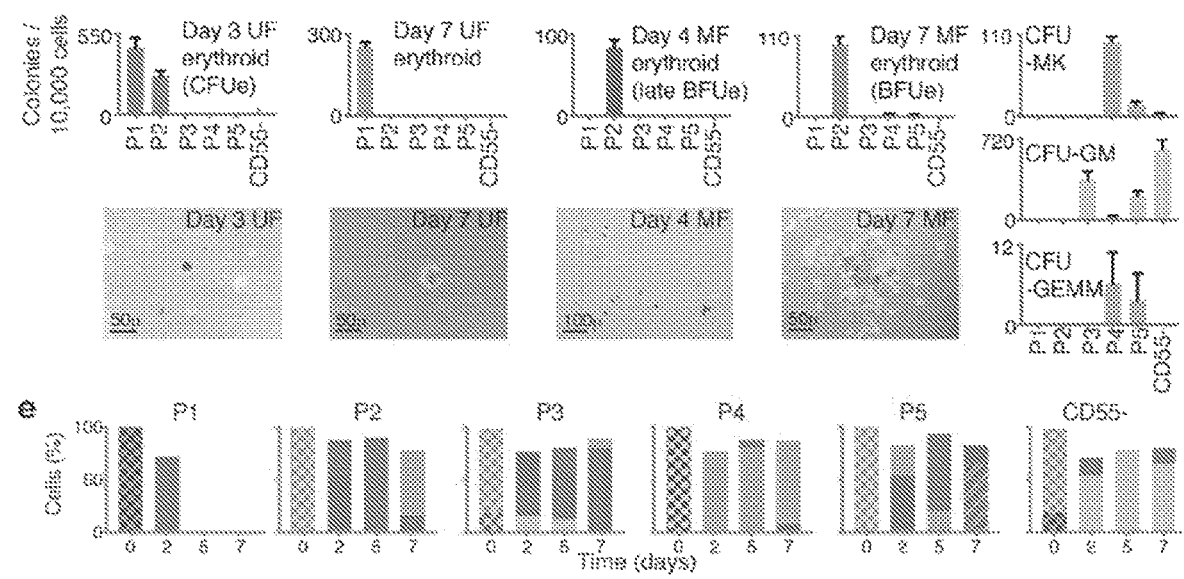

For detailed analysis, a flow cytometric sorting strategy was developed and guided by the SPRING plot expression patterns of alpha integrins Cell surface markers CD150 and CD105, used previously to identify CFUel2, were combined with Itga2b, Itga6 and the transferrin receptor (Tfrc, CD71) to subdivide Kit+CD55+ bone-marrow into five subpopulations, P1 to P5 (FIG. 3, Panel b). Using qRT-PCR for genes that mark specific locations within the SPRING plot, each of P1 to P5 maps onto a distinct region of the plot, with P1, P2 and P5 forming the principal regions of the erythroid trajectory, and P3 and P4 marking the basophilic and megakaryocytic branches, respectively (FIG. 3, Panel c). Other cell fates were within the CD55– zone of the plot (FIG. 3, Panel c).

Next, this strategy was used to examine the differentiation potential of each of the sorted populations, and by, extension, the fate potential of their corresponding regions on the SRPING plot. Colony formation assays ((FIG. 3, Panel d) and liquid culture (FIG. 3, Panel e) in the presence of a cocktail of cytokines that support differentiation of myeloid and erythroid lineages were used. P1 and P2, which correspond to the CEP and EEP regions, respectively, both gave rise to erythroid colonies, confirming their location on the erythroid trajectory. No other subset gave rise to erythroid colonies, suggesting that P1 and P2 contain all unipotential erythroid progenitors in the bone-marrow. Of interest, P1 and P2 differ in their colony morphology: P1 colonies were unifocal, maturing on day 3 (CFUe), but also included larger unifocal colonies that matured later, up to day 7 (FIG. 3d). By contrast, P2 colonies were multifocal, maturing on day 4 (late BFUe), or larger multifocal colonies maturing later (early BFUe). Thus, the molecular stage of progenitors, either EEP or CEP, determines their ability to form either multifocal or unifocal colonies, and is somewhat less rigidly related to the time it takes for the colony to complete erythroid maturation.

The P5 subset gave rise to granulocyticlmonocytic (GM), megakaryocytic and mixed myeloid colonies, in agreement with its location in the EBMP and MPP portions of the SPRING plot, P4 was highly enriched for megakaryocytic colonies. Liquid culture of the sorted populations (FIG. 3, Panel e) largely recapitulated the results of colony formation assays. In addition, it showed that the progeny of P3 cells are positive for FceRI, suggesting a basophilic fate, in agreement the mapping of P3 to the basophilic branch of the SPRING plot. P2 cells cultured for 7 days contained CD41+ and FceRI+ progeny, in agreement with the least mature cells within this subset originating from the early bottleneck region, where cells are predicted to have substantial residual probabilities for the basophilic and megakaryocytic fates. CD55– cells, as expected from their location in the GM region of the SPRING plot, gave rise principally to GM colonies and to cells with GM markers in liquid cultures.

Expression of canonical TFs in each of the sorted populations was consistent with prediction (FIG. 1, Panel e). Taken together, these analyses validate the SPRING plot structure, the extracted erythroid trajectory, and PBA predictions Example 5

Novel Regulators of Early Erythroid Progenitors

Next, EEP and CEP genes that encode cell-surface receptors with known ligands were screened for which could be tested for a potential regulatory effect. Three such receptors were identified: ryk, mst1r and IL-17ra. Ryk belongs to the receptor tyrosine kinase (RTK) family but has an inactive kinase domain and functions in non-canonical Wnt signal transduction. Mst1r (macrophage stimulating 1 receptor/RON kinase) is an RTK expressed in multiple tissues and tumors. It was found to associate with the EpoR in a CFUe culture system, but could not be activated directly by its ligand, Macrophage Stimulating Protein (MSP/mst1), in that context. IL-17ra is one of several receptors for the IL-17 proinflammatory cytokines, which have been reported to be broadly inhibitory on bone-marrow progenitors. However, the expression of an IL-17 receptor by erythroid progenitors had not been documented.

Figure 4:
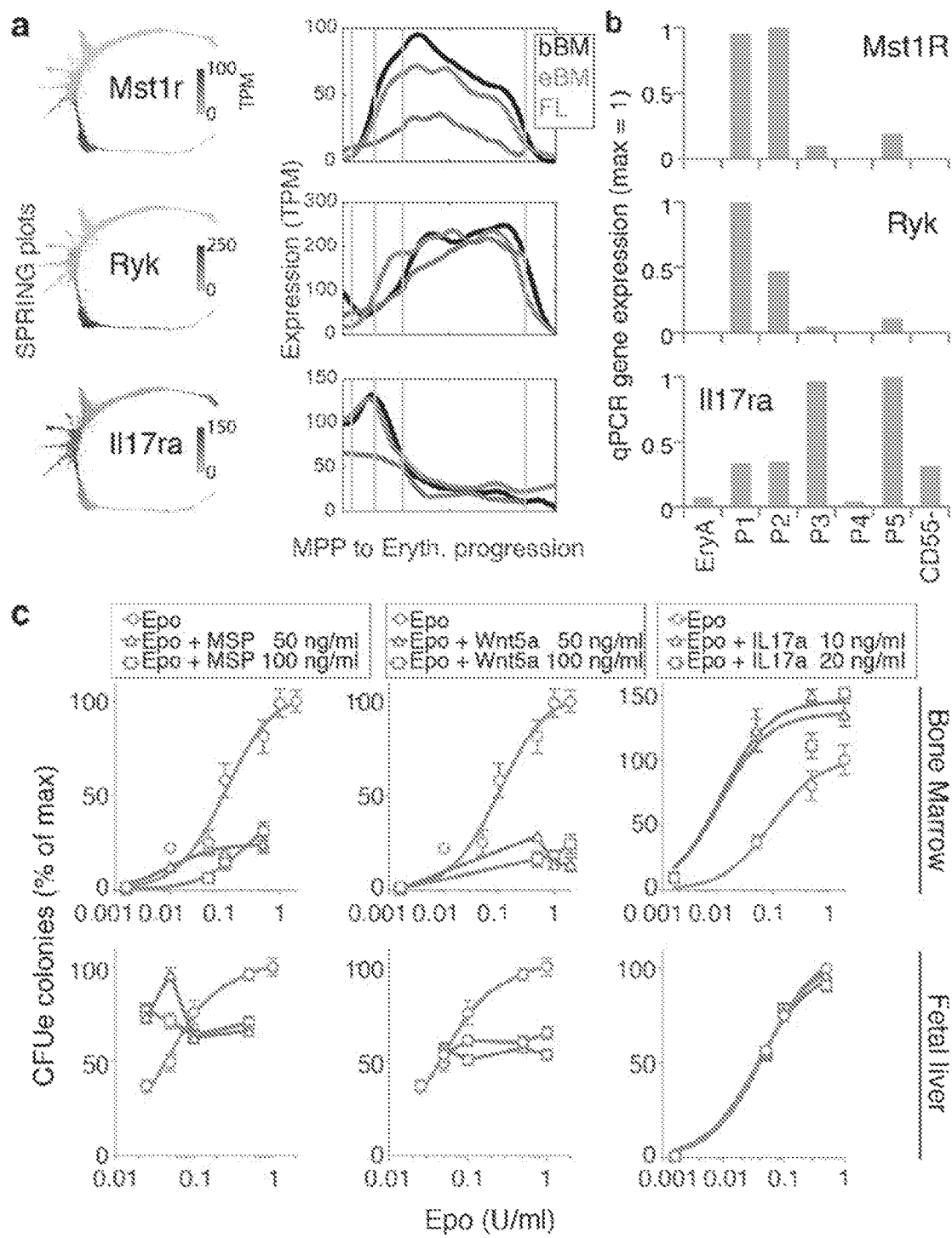
FIG. 4 includes 3 panels (Panels a-c). Panel a shows SPRING plots and temporal ordering of gene expression of receptors during erythropoiesis. Panel b show the qPCR validation on fractionated cell populations. Panel c shows the CFUe assay results for the three ligands.
Figure 7:
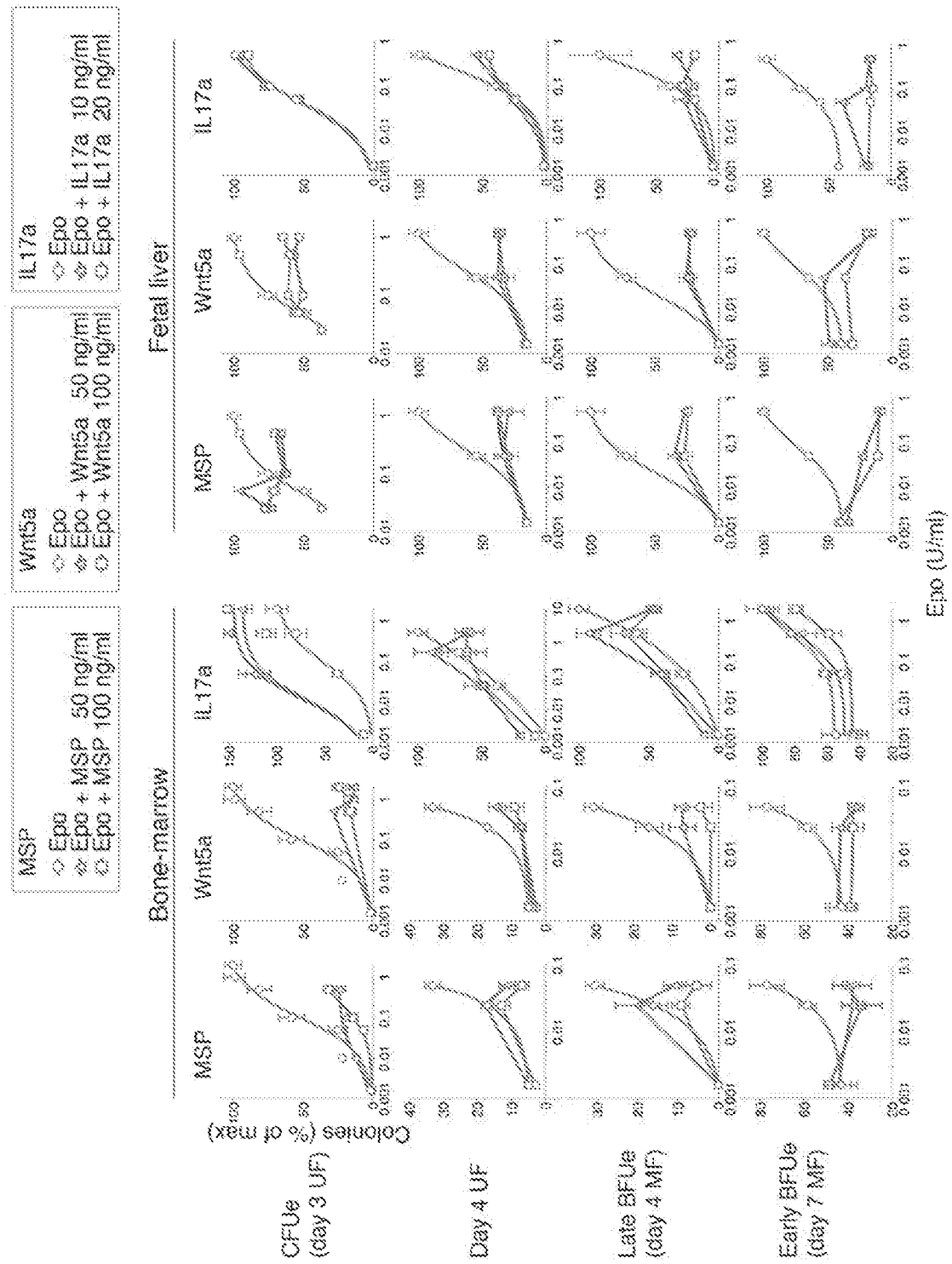

Here, IL-17ra is expressed in the EEP region of the bBM SPRING plot (FIG. 4, Panel a) and its corresponding P2 subset (FIG. 4, Panel n), and to a lesser extent in the CEP/P1 region, in addition to its expression by non-erythroid cells. Both Ryk and mst1r are expressed more selectively, principally within the CEP/P1 region of the erythroid trajectory (FIG. 4, Panels a and n). Wnt5a, MSP and IL-17a were used to stimulate Ryk, mst1r and IL-17ra respectively, and measured their interaction with Epo, an essential erythroid cytokine, using colony formation assays (FIG. 4, Panel c). Epo concentration in blood ranges from 5-10 mU/ml in the basal state, to 10,000 mU/ml in extremely severe anemia The addition of MSP to FL in the presence of mildly elevated Epo concentrations (50 mU/ml, characteristic of mild anemia) was equivalent to a 10-fold increase in Epo concentration, generating over 2 fold the number of CFUe (day 3 unifocal) colonies. However, in the context of high Epo (>100 mU/ml), the addition of MSP was inhibitory. MSP-mediated inhibition was also seen in earlier FL progenitors and in BM progenitors of all stages. Unlike MSP, Wnt5a was a consistent and potent inhibitor of all erythroid colony formation in both FL and BM. Finally, IL-17a had a striking potentiation of BM CFUe colony formation throughout the Epo dose-response curve; giving rise to 4-fold more colonies at lower Epo (50 mU/ml), and increasing the maximal colony formation number at high Epo by 50%. It had a milder stimulatory effect in earlier progenitors that did not persist at the higher Epo doses, and no effect in FL progenitors (FIG. 7). In summary, MSP, Wnt5a and IL-17a may provide powerful modulation of pre-ETD erythroid progenitors, in a manner that is highly dependent on their developmental stage and background state of progenitor stimulation (stress v. basal).

Example 6

Synchronization in S Phase at the Switch from Early Erythropoiesis to ETD

GSEA analysis shown in FIG. 2 indicates that DNA replication and S phase genes are prominent during the CEP stage (FIG. 2, Panels f and h). Broadly, these genes fall into two dynamic patterns: those whose expression within the CEP stage is stable (FIG. 2, Panel f, Nfia cluster;, and genes whose expression is ramped up with progression through the CEP stage, rising to a sharp peak just prior to the transition into ETD (FIG. 2, Panel f, E2F4 cluster). The latter dynamic suggests the possibility that its genes are mechanistically relevant to the activation of the ETD program. To examine this further, an unbiased analysis using the Whitfield database (*Mol Biol Cell* 13, 1977-2000, 2002) of genes with cell cycle-phase-specific expression was pursued. The genes of each cell cycle phase were ordered by the timing of their peak expression along the MPP to Ery progression (FIG. 5, Panel a).This shows a notable group of G1/S and S phase genes peaking simultaneously, just prior to the ETD transition (marked by a dashed yellow line); a large group of G2 and G2/M genes also peaked simultaneously, just following the ETD transition. A line plot of the mean expression of all genes from each cell cycle phase (FIG. 5, Panel b) confirms a peak of G1/S and S phase genes simultaneous with that of the sharp expression peak of the TF Klf1, and just preceding the rapid induction of Tfrc (CD71), a marker of ETD activation. The G1/S and S phase peaks are followed closely by G2 and G2/M peaks. Since the cells are ordered according to their total gene expression state, likely dominated by their differentiation stage, the orderly sequential pattern of G1S, S, G2 and G2/M peaks suggests that transition into the ETD is synchronized with the cell cycle phase, specifically, with G1/S or S phase.

Figure 5:
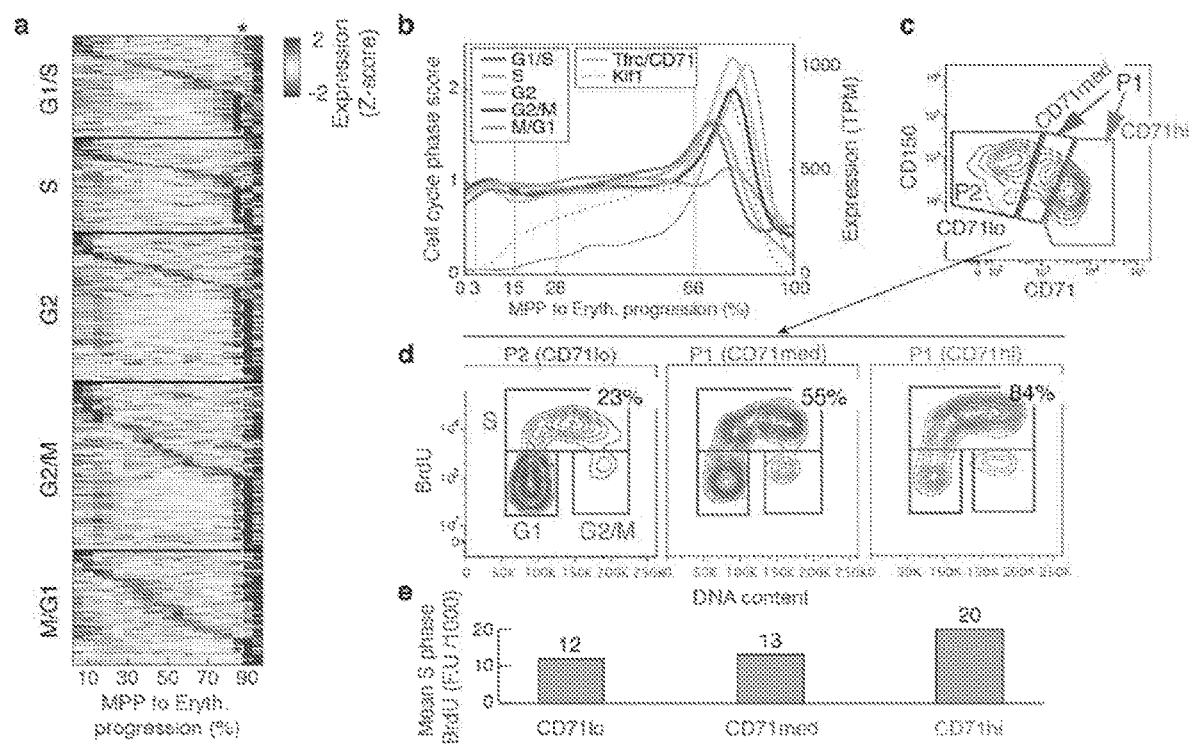
FIG. 5 includes 7 panels (Panels a-h), which show data representing synchronization in S phase at the switch from early erythropoiesis to ETD FIG. 6 includes 7 panels (Panels a-g), which show that certain ligands described herein provide modulation of pre-ETD erythroid progenitors.
Figure 5:
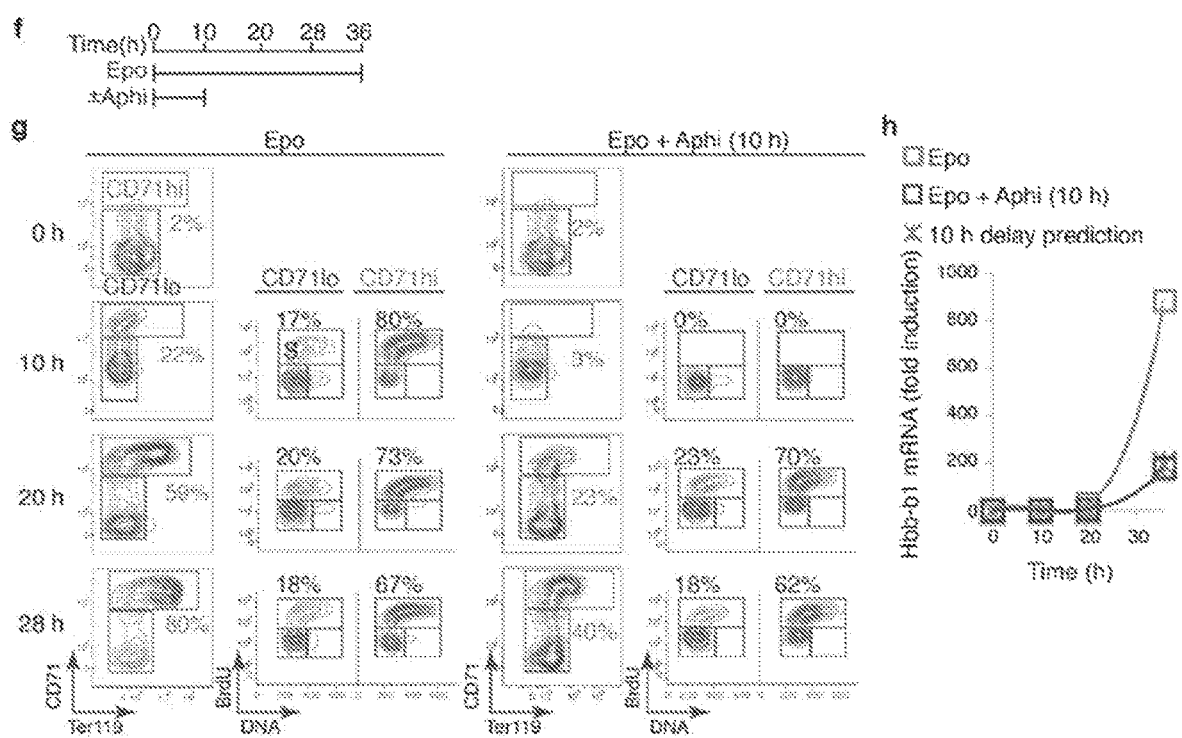
Figure 6:
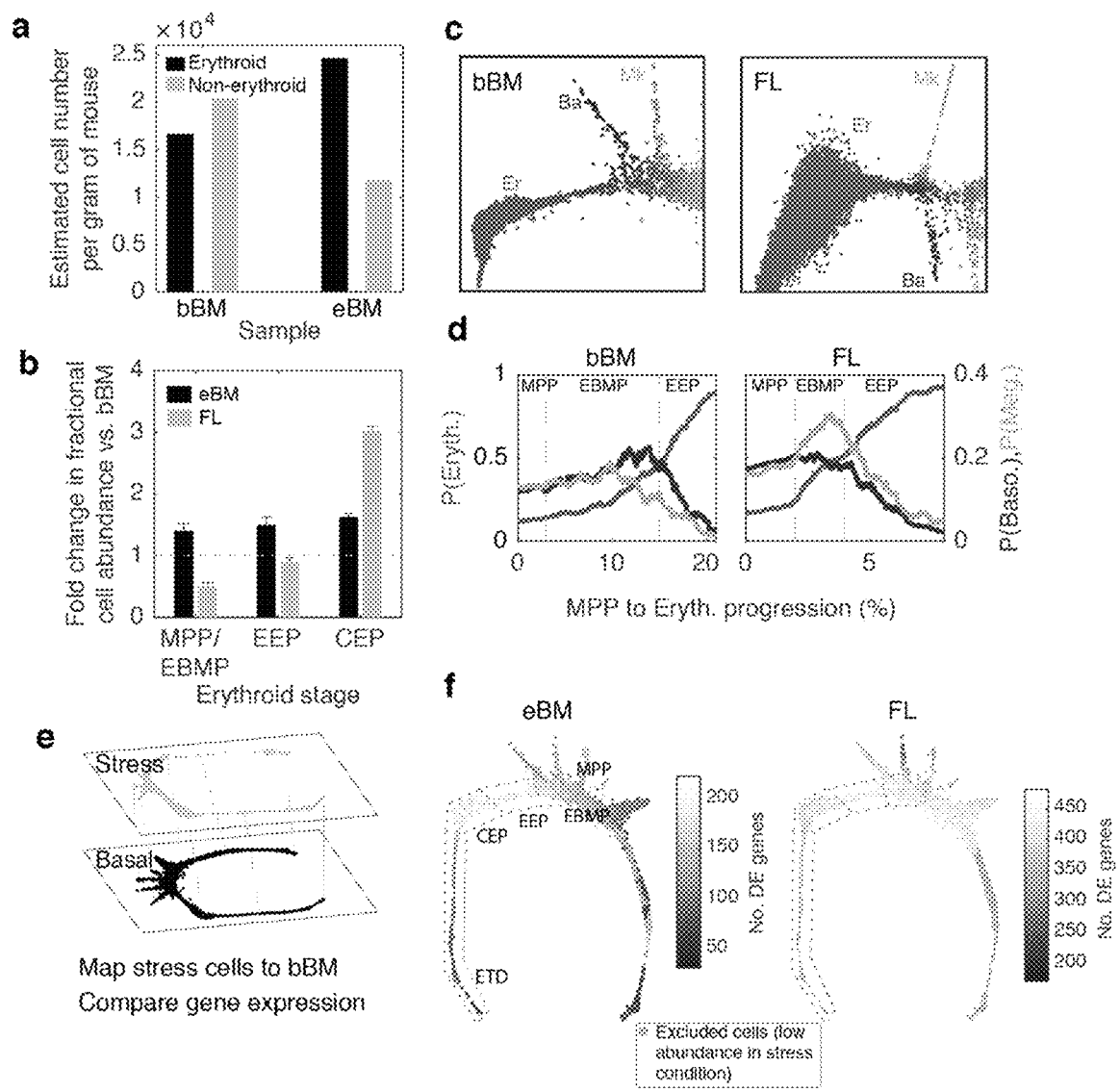
Figure 6:
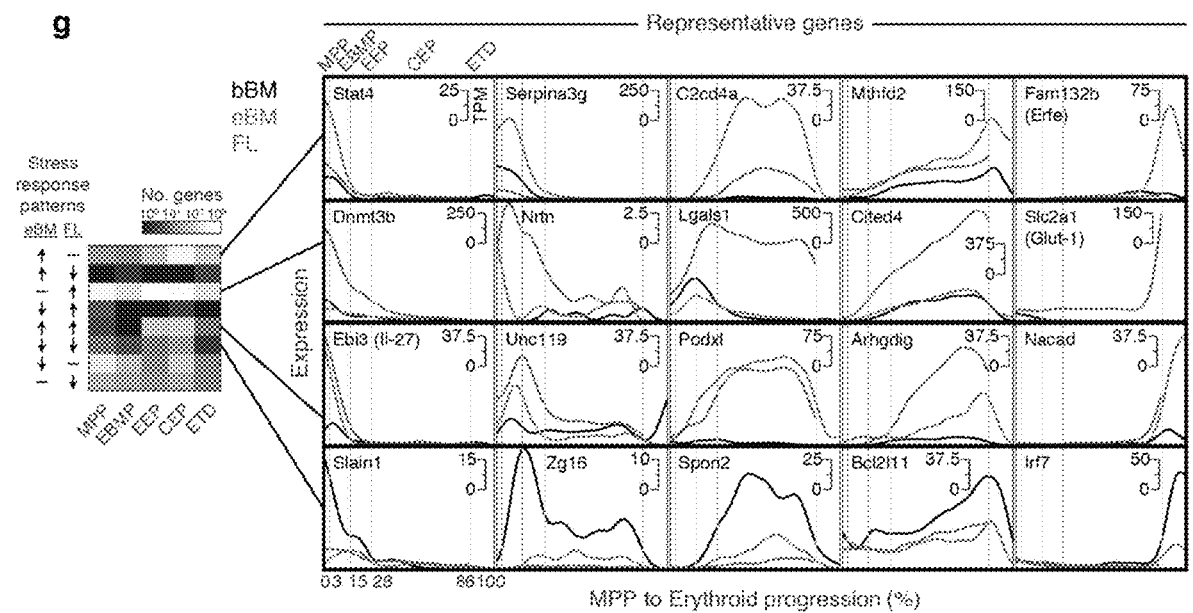

In addition, examination of genes associated with each cell cycle phase shows that different subsets of regulators appear to dominate different segments of the erythroid trajectory (FIG. 5, Panel a). For example, in the case of cyclin D, a G1 cyclin that promotes S phase entry, the ccnd2 isoform dominates the EEP and CEP stages, to be replaced with the ccnd3 isoform at the ETD transition (FIG. 7). For the E2F TFs, which function as key regulators of S phase genes, E2F6 is stably expressed through the CEP stage, E2F4 is ramped up with progression along the CEP stage, E2F1/7/8 peak with the ETD transition, and. E2F2 is induced during the ETD. These patterns raise the possibility that, at each stage of differentiation, a distinct set of regulators drives a differentiation-stage-specific specialized cell cycle program.

In the FL, activation of the ETD coincides with, and is dependent on, a specialized S phase, in which DNA replication rate is faster. The present observations (FIG. 5, Panels a and h) predict a similar interaction between S phase and activation of the ETD in the adult BM. To test this possibility, the cell cycle status of CEP/P1 and EEP/P2 cells were first examined in vivo by pulsing mice with the nucleotide analog bromodeoxyuridine (BrdU) for 30 minutes prior to BM harvesting (FIG. 5, Panel c). BrdU incorporates into DNA of cells that are in S phase during the time of the pulse. The fraction of cells in S phase (BrdU+) increases dramatically in CEP/P1 cells as they begin to upregulate CD71 (Tfrc), in close agreement to the line plots of Tfrc and S phase genes in FIG. 5, Panel b. Of interest, the rate of BrdU incorporation into CEP/P1 cells in S phase was substantially higher following upregulation of Tfrc (CD71hi) (FIG. 5, Panel c, mean S phase BrdU), suggesting that, as in the FL, the S phase that is synchronized with ETD activation is specialized by being faster.

To test whether the synchronization of ETD activation with S phase reflects mechanistic dependence, BM cells were isolated prior to the onset of ETD (Kit+CD55+Lin−CD71lo, FIG. 5, Panels f-h). The cells were cultured in the presence of Epo, which allowed them to activate the ETD, reflected first by the upregulation of CD71, followed by the upregulation of the erythroid cell surface marker Ter119, and induction of the beta-globin gene (Hbb-b1). The addition of the DNA polymerase inhibitor aphidicolin (Aphi) for the first 10 hours of culture, arrested S phase and paused upregulation of CD71, both of which resumed once Aphi was removed. The ensuing ETD activation proceeded with a 10-hour delay in the induction of CD71 and Hbb-b1 (FIG. 5, Panels g and h). These findings show that activation of the ETD is synchronized with, and requires, a specialized, faster S phase.

Example 7

Fetal and Stress Erythropoiesis: Key Genetic Pathways

The absolute number of Kit+ cells does not change following Epo stimulation. Therefore, expansion of the amplification module is at the expense of non-erythroid outcomes. This raises the possibility that Epo stimulation, either directly or indirectly, alters the MPP differentiation bias, or somehow inhibits non-erythroid outcomes.

Example 8

Growth Factor Regulators of Early Erythropoiesis

As described in Example 5, EEP and CEP expressed genes that encode cell-surface receptors with known ligands were screened and then tested for potential regulatory effects. Three such receptors: Ryk, Mst1r and Il17ra were identified.

Figure 15:
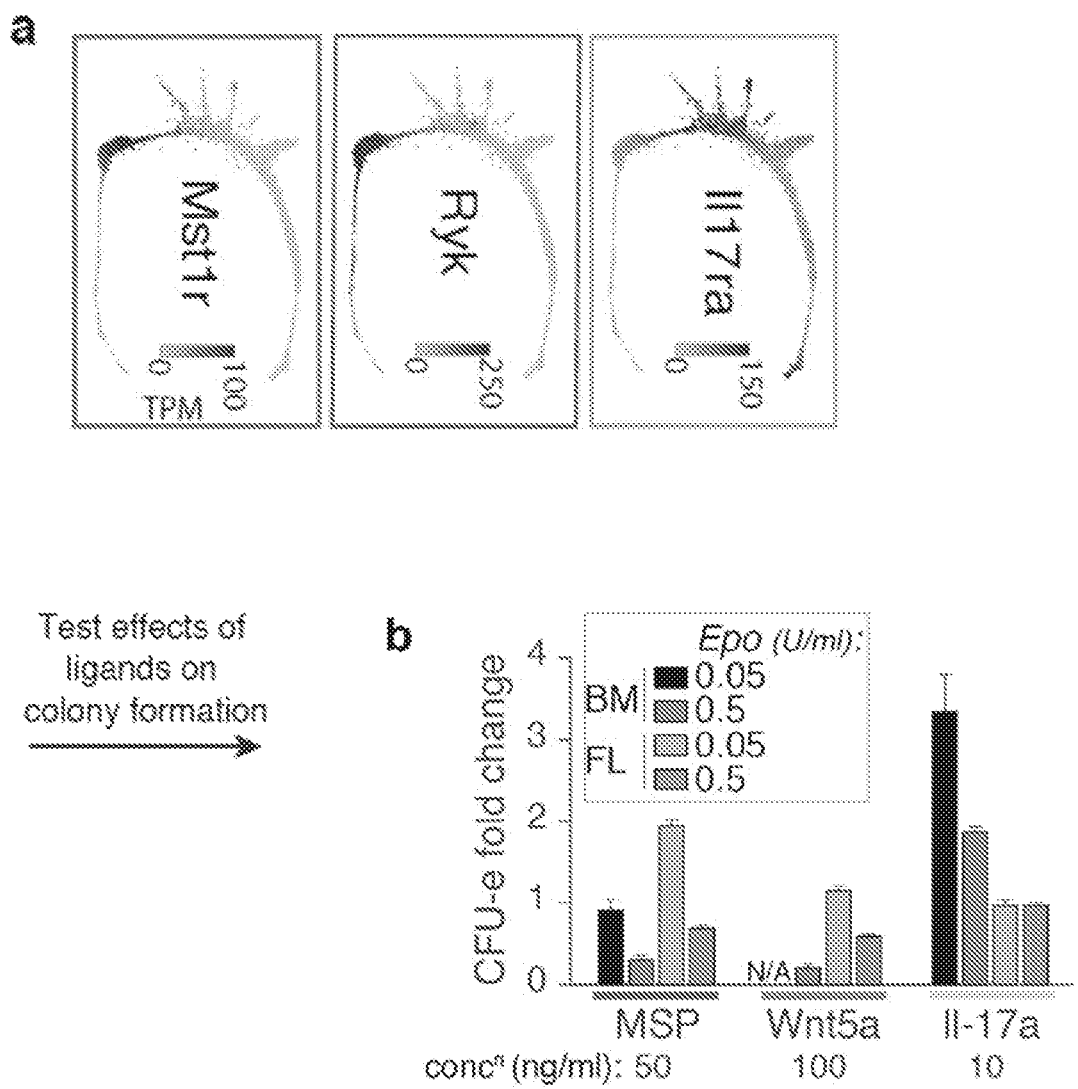
FIG. 15 has 8 panels (panels a-h). Panel a shows that expression of Mst1r, Ryk and Il17ra peaks at CEP or EEP stage. Panel b shows representative changes in the number of CFU-e colonies formed in methylcellulose in the presence of the cognate ligands MSP, Wnt5a or Il17a to culture media. Error bars show SD of two independent experiments, with four replicates per experiment. Panel c shows representative Epo dose response curve for IL-17a, showing a persistent IL-17a response even at saturating doses of Epo. Panel d shows that the IL-17a response is dependent on IL-17Ra expression, as demonstrated by a loss of response in colonies from Il-47Ra-/- mice. Colonies scored per 500,000 plated bone marrow (BM) cells in the presence of Epo at 0.05 U /ml. Data is mean±SD of triplicate samples; representative of two independent experiments. Panel e shows that IL-17a also stimulates CFU-e in freshly isolated human bone marrow mononuclear cells. Colonies scored per 85,000 cells plated. Data is mean±SD of triplicate samples. Panel f shows FACS analysis of fixed and permeabilized cells stained for pStat3 and pStat5 and shows that IL-17a rapidly activates intracellular signaling through these pathways independently of Epo. Freshly isolated mouse BM cells were starved of cytokines for 3 hours, and then stimulated with Epo, IL-17a or both cytokines. FACS profiles on left are for baseline (starved) cells (solid histograms), and 60 minutes—-post stimulation (line histograms). On the right is a time course of the fraction (%) of cells positive for either pStat in the same experiment.
Figure 15:
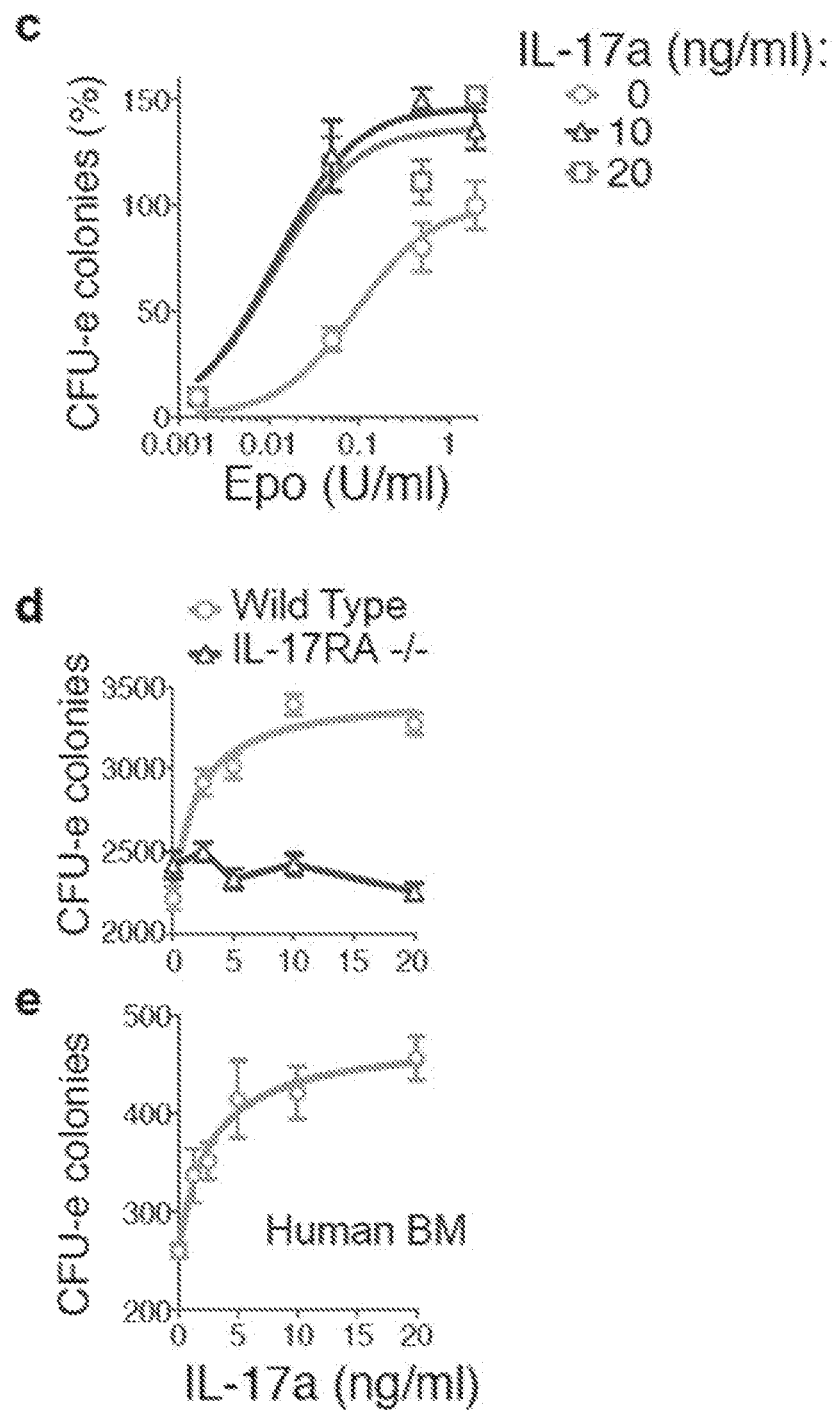
Figure 15:
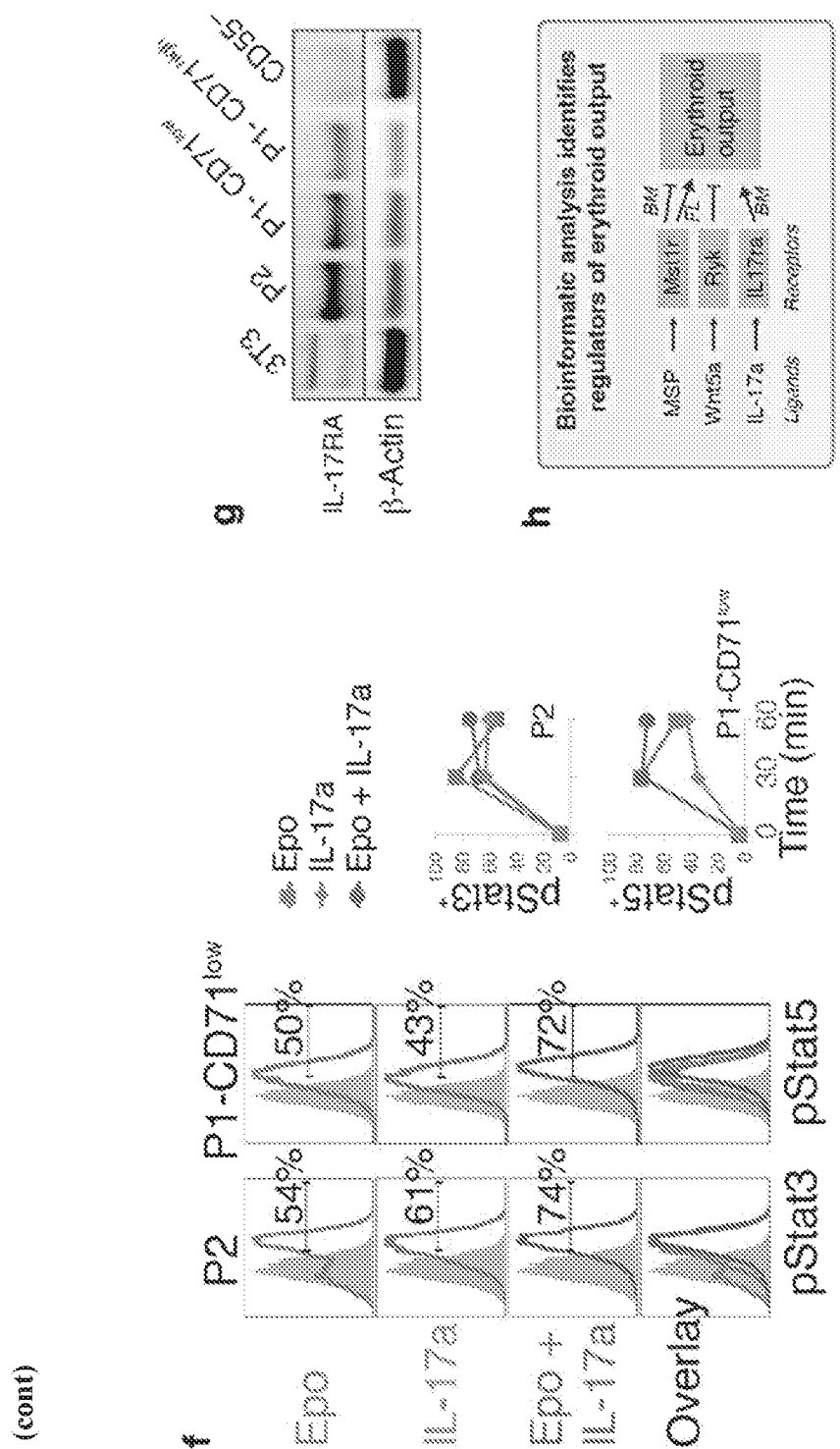

In bone marrow (BM), 1117ra was expressed by EEPs/P2 and to a lesser extent by CEPs/P1, in addition to non-erythroid cells. Both Ryk and Mst1r are expressed more selectively, though not exclusively, by EEP and CEP cells (FIG. 15, Panel a, and FIG. 16, Panels a and b). Ryk, Mst1r and IL-17Ra were stimulated with their respective ligands, Wnt5a, MSP and IL-17a, using Epo-dependent erythroid colony formation as readout (FIG. 15, Panels b and c, FIG. 7). Epo concentration in blood varies from ~10 mU/ml in health, to 10,000 mU/ml in severe anemia. It was found that addition of MSP to FL in the presence of mildly elevated Epo (50 mU/ml) was equivalent to a 10-fold increase in Epo concentration, generating over 2-fold the number of CFU-e colonies. However, MSP was inhibitory in other contexts, and Wnt5a was a consistent and potent inhibitor of all erythroid colony formation in both FL and BM (FIG. 15. Panel b, FIG. 7). By contrast, IL-17a mediated a potentiation of adult BM CFU-e colony formation throughout the Epo dose-response curve, giving rise to 4-fold more colonies at lower Epo (50 mU/ml), and to a ~50% increase in colony formation when added to maximal levels of Epo (FIG. 15, Panels b. and c). It had a milder stimulatory effect in BFU-e progenitors, and no effect in FL (FIG. 16).

The stimulatory effect of IL-17a on CFU-e formation was mediated through expression of IL-17Ra, as shown by its absence in BM of IL-17Ra-deleted mice (FIG. 15, Panel d), and was also evident in human BM (FIG. 15, Panel e). Further, IL-17a stimulation was saturable, with a low EC50 (2.0±1.2 ng/ml (60 pM) in mouse, 2.7±1.6 ng/ml (81 pM) in human BM), consistent with it being the direct consequence of high affinity-binding of IL-17a to IL-17Ra, Stimulation with IL-17a resulted in rapid phosphorylation of the intracellular signaling mediators Stat3 and Stat in CEP and EEP (FIG. 15, Panel f). Further, freshly sorted BM CEP/P1 and EEP/P2 expressed IL-17Ra by western blotting (FIG. 15, Panel g). Taken together, these findings suggest previously unknown complex regulatory modulation of EEP and particularly of CEP through the expression of a number of growth factor receptors new to erythropoiesis.

Methods:

Growth factor perturbations of erythroid colony formation: CFU-e and BFU-e colony formation assays in MethoCult (M3234 STEMCELL Technologies) were carried out on either freshly isolated bone marrow or on embryonic day 13.5 fetal liver cells from Balb/cJ mice. The following growth factors were tested: MSP/MST1 (R&D systems; CAT #6244-MS-025), Recombinant Human/Mouse Wnt-5a (R&D systems; CAT #645-WN-010) and Recombinant Murine IL17 (IL-17A) (PeproTech; CAT 4210-17). In each experiment, a range of Epo concentrations was tested, with or without added additional growth factors (MSP, Wnt5a or IL-17A) as indicated in FIG. 5 and in Extended Data FIG. 12. In addition to Epo, IL-3 (long/mL) and SCF (50ng/ mL) were added to the MethoCult in the case of BFU-e assays. Each condition was tested in quadruplicates, in at least 2 separate experiments. Colonies were scored on day 3 (for CFU-e), day 4 (for late BFU-e) and on day 7 (for early BFU-e) following staining with diaminobenzidine, to highlight hemoglobin expression.

IL17RA-deleted mice: To generate the IL-17RA -deleted line, IL-17RA flox/+mice9 were bred with CMV-Cre mice 0003465, JAX lab). The generation of il17ra del allele in the F1 generation of il17raflox/+×CMV-Cre mating pairs were screened by PCR of tail DNA. To remove the CMV-Cre allele present in the F1 generation, IL-17RA del/+; CMV-Cre+/− mice were outcrossed with B6 mice.

Colony-formation assays with human bone-marrow: Human bone-marrow mononuclear cells (MNCs) (85,000 cells, STEMCELL Technologies 70001.1) were mixed with 1 ml MethoCult (STEMCELL Technologies H4230) supplemented with either EPO (0.05 U/ ml), and in the presence or absence of IL-17a (R&D systems 7955-IL-025). CFUe colonies were scored from triplicate plates on day 7.

Flow cytometric sorting or P1 to P5 subsets: Bone marrow cells from adult BALB/cj male or female mice, ages 8-12 weeks, were lineage-depleted using the Mouse Streptavidin RapidSpheres Isolation Kit (STEMCELL Technologies [Cat# 19860A]), with the following biotinylated antibodies:

anti-CD11b (Clone M1/70 [#557395], BD Biosciences)
anti-Ly-6G and Ly-6C (Clone RB6-8C5 [#553125], BD Biosciences)
anti-CD4 (Clone RM4-5 [4553045], BD Biosciences)
anti-CD8a (Ly-2) (Clone 53-6.7 [#553029], BD Bioscience)
anti-CD19 (Clone ID3 [#553784], BD Biosciences)
anti-TER119 (Clone TER119 [#553672], BD Biosciences), Lineage-depleted cells were then labeled with the following antibodies in the presence of 1% rat serum:

streptavidin Alexa Fluor 488 (Molecular Probes), to mark lineage-positive cells
CD117-APC Cy7 (Clone 2B8 [#105826], Biolegend)
TER119-BUV395 (Clone TER-119 [#563827], BD Biosciences)
CD71-PE Cy7 (Clone 1117217 [##113812], Biolegend)
CD55-AF647 (Clone RIKO-3 [#131806], Biolegend)
CD105-PE (Clone IMJ7/18 [#120408], Biolegend)
CDI50-BV650 (Clone TC15-12F12.2 [#115931], Biolgened)
CD41-BV605 (Clone MWReg30 [#133921], Biolegend)
CD49f (=itga6) BV421 (Clone GoH3 [#313624], Biolegend)

Figure 14:
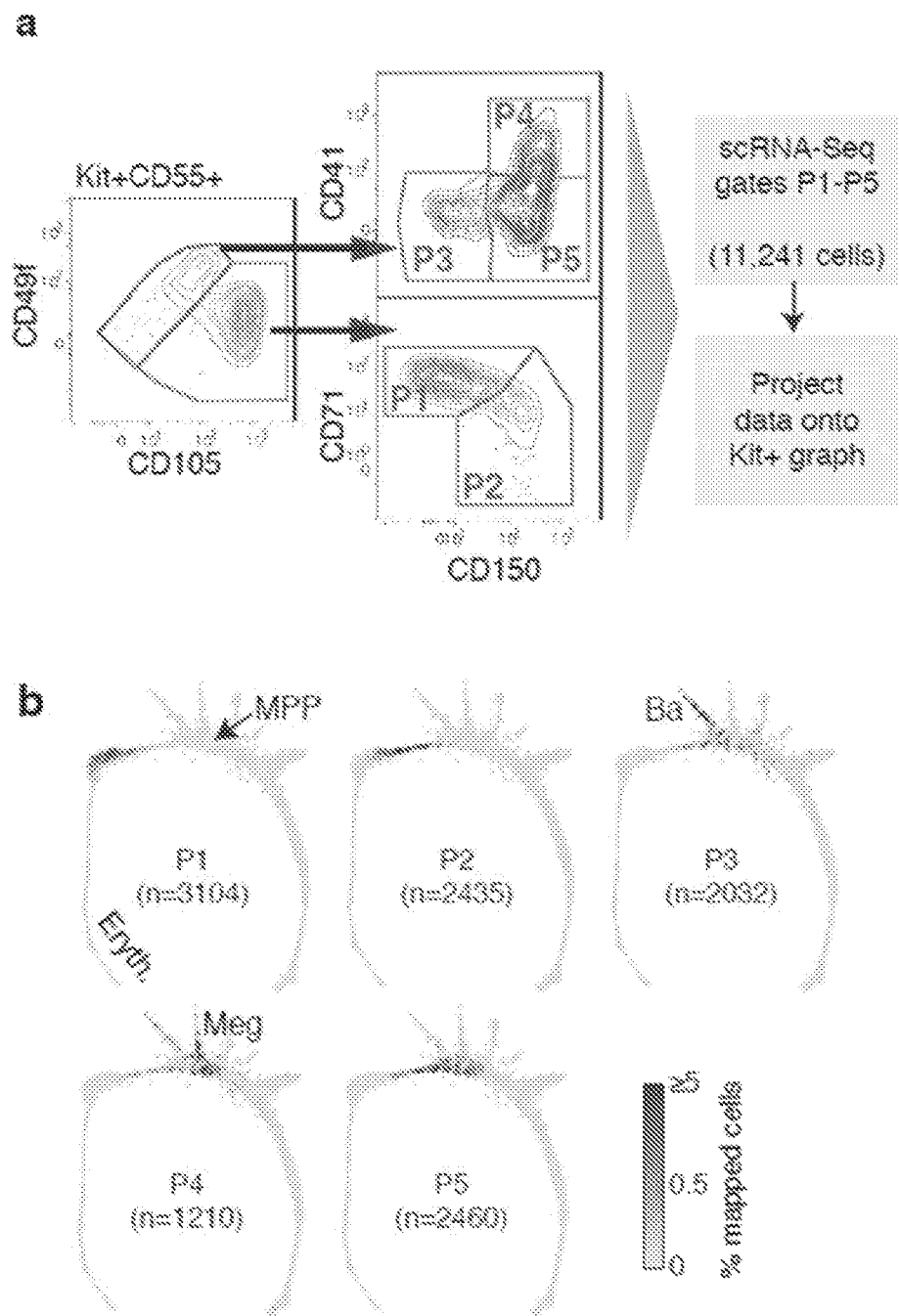
FIG. 14 includes 7 panels (Panels a-f). Panel a shows a flow-cytometric sorting strategy, dividing Kit⁺CD55⁺ BM cells into gates P1 to P5 based on expression of CD49f (Itga6), CD105 (Eng), CD41 (Itga2b), CD150 (Slamf1), and CD71 (Tfrc) Freshly sorted cells from each gate were profiled using scRNA-Seq. Panel h shows the sorted sub-populations P1-P5 localized on the Kit+ graph by assigning single cell transcriptomes from each sub-population to their most similar counterparts. The density of projected cells is represented using a heatmap. Panels c through e show colony formation assays in methylcellulose carried out on freshly sorted P1 to P5 subsets and on Kit⁺CD55⁻ cells. These assays show that P1 and P2 subsets completely define classic CFU-e and BFU-e progenitors. Erythroid colonies were classified as either unifocal (Panel c) or multifocal (Panel d). CFU-MK=Megakaryocytic colonies, CFU-GM=granulocytic and/or monocytic colonies; CFU-GEMM=mixed myeloid colonies. Results are mean±SE of two independent sorts. Colony assays were performed in triplicate. Images show erythroid colonies, stained with diaminobenzidine to highlight hemoglobin expression. The P1 population enriches 150-fold for CFU-e, compared with total bone marrow (BM); the P2 population enriches 50-fold, 80-fold and 45-fold for CFU-e, late and early BFU-e, respectively. Panel f is a summary of erythroid colony formation potential in FACS subsets.
Figure 14:
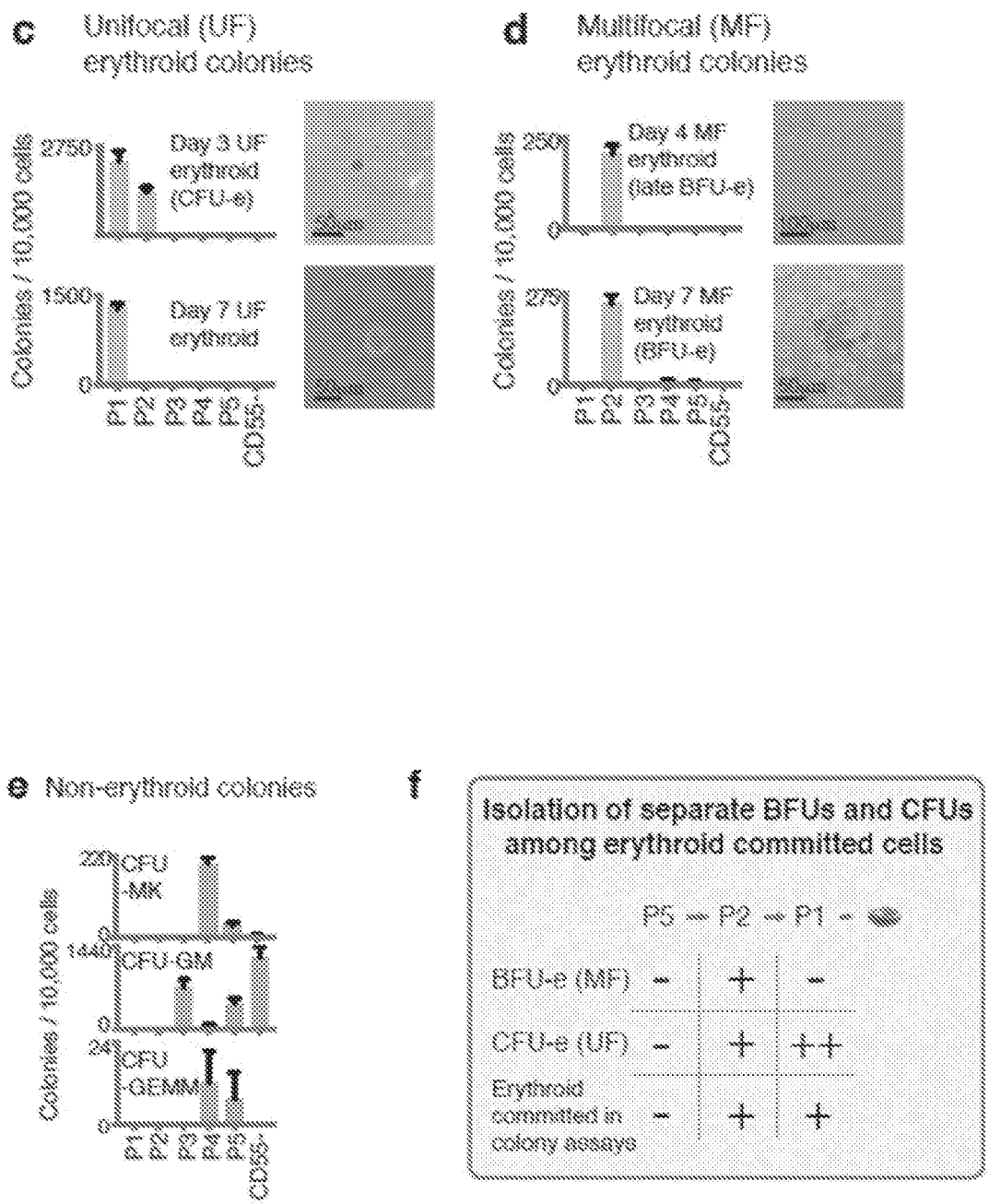

Following washes, cells were re-suspended in DAPI-containing buffer and sorting was performed on BD FACSAria II with a 100μ nozzle. Sorted populations were defined as in FIG. 14.

qRT-PCR on sorted populations: RNA was prepared from sorted cell subsets using the RNeasy Micro Kit (QIAGEN; CAT# 74004) or TRIzol reagent (Ambion; CAT# 15596026), and measured with RiboGreen RNA reagent kit (Thermo Scientific) the 3300 NanoDrop Fluorospectrorneter. cDNA was synthesized using the same amount of input RNA for all samples in a parallel reaction, using the Super Script III first-strand synthesis system for RT-PCR (Invitrogen) with random hexamer primers. The ABI 7300 sequence detection system, TaqMan reagents and TagMan MGB probes (Applied Biosystems, San Diego, Calif.) were used following the manufacturer's instructions, qPCR was carried on 4 serial dilutions of each cDNA sample, and the linear part of the template dilution/signal response curve was used to calculate relative mRNA concentrations following normalization to βactin, using the ΔCt method. The following TagMan MOB probes were used: Mst r (Mm00436382—m1), Ryk (Mm01238551_m1), IL17ra (Mm00434214_m1), Mt2 (Mm00809556_s1)

Western Blot Analysis: Bone marrow cells were sorted as above, except that the P1 population was further subdivided into CD71med and CD71hi subsets. For negative controls, 3T3-L1 cells were used. For positive controls, 3T3-L1 cells were transduced with the MICD4-GATA1 retrovirus. Cell pellets were snap-frozen in liquid nitrogen following the sort. Cell lysates were quantified by the BCA Protein Assay Kit (Pierce) and separated by SDS-PAGE gel electrophoresis, PVDF membranes were probed with antibodies against GATA I (N6, sc-265, Santa Cruz), β-actin (ab8227, abeam), MCM5 (Bethyl Laboratories, Inc., A300-195A-M), MCM6 (Bethyl Laboratories, Inc., A300-194A), MCM2 (Bethyl Laboratories, Inc., A300-191A), PCNA (PC10) (Santa Cruz, sc-56), IL-17RA/IL-17R (R&D Systems, AF448). Western blot membranes were quantified using the BIORAD Imaging system and Image Lab software.

Intracellular signaling by Stat3 and Stat5: Freshly harvested bone-marrow cells were enriched for Lin-Ter119- cells using magnetic beads. The enriched cells were incubated a cytokine-free, low serum medium (IMDM with 2% FCS) for 3 hours. EPO (0.5 U/ml) only, IL-17a (20 ng/ml) only, or EPO (0.5 U/ml) and IL-17a (20 ng/ml) were then added to the medium for either 30 or 60 minutes, Cells were harvested, washed with PhosphoWash Buffer 11, stained with LIVE/DEAD kit (Invitrogen), fixed and permeabilized with Cytofix/Cytoperm Buffer (BD 554722) supplemented with 1 mM Sodium Orthovanadate (Sigma 450243-10G), 1 mM β-glycerophosphate (Sigma G9422-10G) and 1 ug/ml Microcystin (EMD Millipore 475815-500UG), and Perm/ Wash Buffer I (BD 557885), and frozen in freezing medium (90% FCS, 10% DMSO, 1mM Sodium Orthovanadate, 1 mM β-glycerophosphate and lug/col Microcystin). When thawed, cells were re-fixed and permeabilized, incubated With 5% milk and 200 ug/ml Rabbit IgG (modified from Porpiglia et al., PLoS Biol. 2012), and stained with p-Stat3- AF488 (B-7) (Santa Cruz sc-8059 AF488), p-Stat5-AF647 (pY694) (BD Bioscience 612599), CD71-PE/Cy7 (Biolegend 113812), CD55-PE (Biolegend 131804), CD105-Pacific Blue (Biolegend 120412), CD150-BV650 (Biolegend 115931), CD49f (Itga6)-PE/Dazzle 594 (Biolegend 313626), CD41-BV605 (Biolegend 133921), CD117 (Kit)- APC/117 (BD Bioscence 560185), Strepavidin-AF700 (Invitrogen S21383) and DAPI. Analysis was on an LSRII FACS analyzer.

Incorporation by Reference

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method of stimulating erythropoiesis in a subject with anemia comprising administering to the subject an IL-17ra agonist, wherein the IL-17ra agonist comprises a protein that binds to IL-17ra protein or a heterodimeric IL-17a/f protein.

2. The method of claim 1, wherein the subject has congenital anemia, Diamond Blackfan Anemia, or cancer-associated anemia.

3. The method of claim 1, wherein the cancer is selected from breast, prostate, lung, skin, colorectal, cervical, pancreatic, ovarian, lymphoma, leukemia, liver, testicular, and brain cancer.

4. The method of claim 1, further comprising administering to the subject erythropoietin or an erythropoietin derivative.

5. The method of claim 4, wherein the erythropoietin or erythropoietin derivative is asialoerythropoietin, N-deglycosylated erythropoietin, 0-deglycosylated erythropoietin, erythropoietin with reduced carbohydrate content, erythropoietin with altered glycosylation patterns, erythropoietin with carbohydrates oxidized then reduced, arylglyoxal-modified erythropoietin, alkylglyoxal-modified erythropoietin, 2,3-butanedione-modified erythropoietin, cyclohexane-dione-modified erythropoietin, biotinylated erythropoietin, N-alkylated-lysyl-erythropoietin, glucitolyl lysine erythropoietin, alpha-deoxy-alpha-fructosyllysine-erythropoietin, carbamylated erythropoietin, acetylated erythropoietin, succinylated erythropoietin, alpha-carboxyalkyl erythropoietin, nitrated erythropoietin, iodinated erythropoietin.

6. The method of claim 1, wherein the IL-17ra agonist comprises an IL-17f protein.

7. The method of claim 1, wherein the IL-17ra agonist comprises a heterodimeric IL-17a/f protein.

* * * * *